US011591609B2

(12) United States Patent
Hilfiker et al.

(10) Patent No.: US 11,591,609 B2
(45) Date of Patent: Feb. 28, 2023

(54) MODULATING REDUCING SUGAR CONTENT IN A PLANT

(71) Applicant: PHILIP MORRIS PRODUCTS S.A., Neuchatel (CH)

(72) Inventors: Aurore Hilfiker, Lausanne (CH); Lucien Bovet, La Chaux-de-Fonds (CH)

(73) Assignee: Philip Morris Products S.A., Neuchatel (CH)

(*) Notice: Subject to any disclaimer, the term of this patent is extended or adjusted under 35 U.S.C. 154(b) by 0 days.

(21) Appl. No.: 17/041,115

(22) PCT Filed: Mar. 27, 2019

(86) PCT No.: PCT/EP2019/057703
§ 371 (c)(1),
(2) Date: Sep. 24, 2020

(87) PCT Pub. No.: WO2019/185699
PCT Pub. Date: Oct. 3, 2019

(65) Prior Publication Data

US 2021/0115459 A1 Apr. 22, 2021

(30) Foreign Application Priority Data

Mar. 28, 2018 (EP) .................................... 18164769

(51) Int. Cl.
*C12N 15/82* (2006.01)

(52) U.S. Cl.
CPC ..... *C12N 15/8245* (2013.01); *C12N 15/8202* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 6,682,918 | B1 * | 1/2004 | Haselkorn | C12N 9/1062 435/193 |
| 2008/0148432 | A1 | 6/2008 | Abad | |
| 2012/0227131 | A1 * | 9/2012 | Abad | C12N 15/8247 800/320.2 |
| 2016/0264980 | A1 | 9/2016 | Abad | |

FOREIGN PATENT DOCUMENTS

| | | |
|---|---|---|
| WO | WO 2016/009006 | 1/2016 |
| WO | WO 2017/042162 | 1/2016 |

OTHER PUBLICATIONS

Legg PD, Chaplin JF, Williamson RE (1997). Genetic diversity in Burley and flue-cured tobacco. Crop Sci 17:943-7. doi:10.2135/cropsci1977.0011183X001700060032x.

International Search Report and Written Opinion for PCT/EP2019/057703 dated Jun. 25, 2019 (9 pages0.

Extended European Search Report for Application No. 18164769.4 dated Nov. 21, 2018 (12 pages).

Cook et al., "Transcriptional Changes Related to Secondary Wall Formation in Xylem of Transgenic Lines of Tobacco Altered for Lignin or Xylan Content Which Show Improved Saccharification", Phytochemistry, vol. 74, Oct. 15, 2014, pp. 79-89.

Database NCBI Gen Pept [Online] Oct. 19, 2016, Predicted: Sucrose Synthase 4-like, partial [Nicotiana tomentosiformis], XP002792338, Database accession No. XP_009610442.2 sequence.

Database Uniport [online] Apr. 12, 2017, RecName: Full=Sucrose Synthase {ECO:0000256, RuleBase: RU280817]; EC=2.4.1.13; XP002783068, retrieved from EBI accession No. A0A1S4B3E6; database accession No. A0A1S4B3E6; & Nicolas Sierro et al., "The tobacco genome sequence and its comparison with those of tomato and potato", Nature Communications, vol. 5, May 8, 2014, XP055378379.

Database Uniport [online] Apr. 12, 2017, RecName: Full=Sucrose Synthase {ECO:0000256, RuleBase: RU280817]; EC=2.4.1.13; XP002792337, retrieved from EBI accession No. A0A1S4B3E6; database accession No. A0A1S4ACT4; & Nicolas Sierro et al., "The tobacco genome sequence and its comparison with those of tomato and potato", Nature Communications, vol. 5, May 8, 2014, XP055378379.

(Continued)

*Primary Examiner* — Brent T Page
(74) *Attorney, Agent, or Firm* — Mueting Raasch Group

(57) ABSTRACT

There is described herein a plant cell comprising: (i) a polynucleotide comprising, consisting or consisting essentially of a sequence having at least 95% sequence identity to SEQ ID NO: 1 or SEQ ID NO: 3 or SEQ ID NO: 9 or SEQ ID NO: 11 or SEQ ID NO: 17 or SEQ ID NO: 19 or SEQ ID NO: 21 or SEQ ID NO: 23; or a polynucleotide comprising, consisting or consisting essentially of a sequence having at least 80% sequence identity to SEQ ID NO: 5 or SEQ ID NO: 7 or SEQ ID NO: 13 or SEQ ID NO: 15; (ii) a polypeptide encoded by the polynucleotide set forth in (i); (iii) a polypeptide comprising, consisting or consisting essentially of a sequence having at least 94% sequence identity to SEQ ID NO: 2; or at least 93% sequence identity to SEQ ID NO: 4; or least 95% sequence identity to SEQ ID NO: 6; or at least 96% sequence identity to SEQ ID NO: 8; or at least 93% sequence identity to SEQ ID NO: 10 or SEQ ID NO: 12; or at least 95% sequence identity to SEQ ID NO: 14; or at least 96% sequence identity to SEQ ID NO: 16; or at least 89% sequence identity to SEQ ID NO: 18; or at least 92% sequence identity to SEQ ID NO: 20; or at least 93% sequence identity to SEQ ID NO: 22; or at least 94% sequence identity to SEQ ID NO: 24; or (iv) a construct, vector or expression vector comprising the isolated polynucleotide set forth in (i), wherein said plant cell comprises at least one modification which modulates the expression or activity of the polynucleotide or the polypeptide as compared to a control plant cell in which the expression or activity of the polynucleotide or polypeptide has not been modified.

15 Claims, 1 Drawing Sheet

Specification includes a Sequence Listing.

(56) References Cited

OTHER PUBLICATIONS

Database Uniport [online] Apr. 12, 2017, "RecName: Full=Sucrose Synthase {ECO:0000256, RuleBase: RU280817]; EC=2.4.1.13; [ECO:0000256 RuleBase: RU280817];", XP002792339, retrieved from EBI accession No. UNIPROT: Unreviewed Database Accession No. A0A1S3YFR7 sequence & Nicolas Sierro et al., "The tobacco genome sequence and its comparison with those of tomato and potato", Nature Communications, vol. 5, May 8, 2014, XP055378379.
Nguyen et al., "Pronounced Phenotypic Changes in Transgenic Tobacco Plants Overexpressing Sucrose Synthase May Reveal a Novel Sugar Signaling Pathway", *Frontiers in Plant Science*, vol. 6, Jan. 2016.
Wang et al., "Analysis of the Sucrose Synthase Gene Family in Tobacco: Structure, Phylogeny, and Expression Patterns", *Planta*, vol. 242, No. 1, Apr. 19, 2015, pp. 153-166.
Wei et al., "Overexpression of Poplar Xylem Sucrose Synthase in Tobacco Leads to a Thickened Cell Wall and Increased Height", PLOS ONE, vol. 10, No. 3, Mar. 2015.
Avila-Ospina L, Marmagne A, Talbotec T, Krupinska K, Masclaux-Daubresse C (2015) The identification of new cytosolic glutamine synthetase and asparagine synthetase genes in barley (*Hordeum vulgare* L.), and their expression during leaf senescence. J Exp Bot 66(7): 2013-2026. doi: 10.1093/jxb/erv003.
Baud S, Vaultier MN, Rochat C (2004) Structure and expression profile of the sucrose synthase multigene family in Arabidopsis. J Exp Bot 55(396)397-409 doi:10.1093/jxb/erh047.
Bieniawska Z, Barratt DHP, Garlick AP, Thole V, Kruger NJ, Martin C, Zrenner R, M. Smith AM (2007) Analysis of the sucrose synthase gene family in *Arabidopsis*. Plant J 49:810-828. doi:10.1111/j.1365-313X.2006.03011.x.
Chen D, Wang S, Xiong B, Cao B, Deng X (2015) Carbon/Nitrogen imbalance associated with drought-induced leaf senescence in sorghum bicolor, PLoS One 10(8):e0137026. doi: 10.1371/journal.pone.0137026.
Cheng M, Hu T, Layton J, Liu CN, Fry JE (2003) Desiccation of plant tissues post-Agrobacterium infection enhances T-DNA delivery and increases stable transformation efficiency in wheat. In Vitro Cellular & Developmental Biology—Plant 39:595-604.
Christ B, Egert A, Süssenbacher I, Kräutler B, Bartels D, Peters S, Hörtensteiner S (2014) Water deficit induces chlorophyll degradation via the 'PAO/phyllobilin' pathway in leaves of homoio-(*Craterostigma pumilum*) and poikilochlorophyllous (*Xerophyta viscosa*) resurrection plants. Plant Cell Environ 37(11): 2521-2531. doi: 10.1111/pce.12308.
De la Torre F, El-Azaz J, Ávila C, Cánovas FM (2014) Deciphering the role of aspartate and prephenate aminotransferase activities in plastid nitrogen metabolism Plant Physiol 164(1):92-104. doi: 10.1104/pp.113.232462.
Diaz-Mendoza M, Velasco-Arroyo B, Santamaria ME, González-Melendi P, Martinez M, Diaz I, (20169 Plant senescence and proteolysis: two processes with one destiny. Genet Mol Biol 39(3): 329-338. doi: 10.1590/1678-4685-GMB-2016-0015.
Edwards KD, Ferandez-Poro N, Drake-Stowe K, Humphry M, Evans AD, Bombarely A, Mueller LA (2017) A reference genome for Nicotiana tabacum enables map-based cloning of homeologous loci implicated in nitrogen utilization efficiency. BCM Genomics 18:448. doi: 10.1186/S12864-017-3791-6.
Gepstein S, Thimann KV (1980) Changes in the abscisic acid content of oat leaves during senescence. Proc Natl Acad Sci USA 77(4): 2050-2053.
Gaufichon L, Rothstein SJ, Suzuki A (2016) Asparagine metabolic pathways in *Arabidopsis*. Plant Cell Physiol 57(4): 675-689. doi: 10.1093/pcp/pcv184.
Jin Y, Ni D-A, Ruan Y-L (2009) Posttranslational elevation of cell wall invertase activity by silencing its inhibitor in tomato delays leaf senescence and increases seed weight and fruit hexose level. Plant Cell 21(7):2072-2089. doi:10.1105/tpc.108.063719.
Leffingwell JC (1999) Leaf chemistry. In: Tobacco: Production, Chemistry, and Technology. Davis DL, Nieslson MT (eds), Blackwell Science.
Legg PD, Chaplin JF, Williamson RE (1997). Genetic diversity in Burley and flue-cured tobacco. Crop Sci 17:943-7. doi: 10.2135/cropsci1977.0011183X001700060032x. Abstract provided.
Lewis RS, Bowen SW, Keogh MR and Dewey RE. (2010) Three nicotine demethylase genes mediate nornicotine biosynthesis in *Nicotiana tabacum* L.: functional characterization of the CYP82E10 gene. Phytochemistry 71:17-18.
Li L, Zhao J, Zhao Y,Lu X, Zhou Z, Zhao C, Xu G (2016) Comprehensive investigation of tobacco leaves during natural early senescence via multi-platform metabolomics analyses. Sci Rep 6: 37976. doi: 10.1038/srep37976.
Masclaux-Daubresse C, Carrayol E, Valadier MH (2005) The two nitrogen mobilisation- and senescence-associated GS1 and GDH genes are controlled by C and N metabolites. Planta 221(4): 580-588. doi: 10.1007/S00425-004-1468-2.
Masclaux-Daubresse C, Reisdorf-Cren M, Pageau K, Lelandais M, Grandjean O, Kronenberger J, Valadier MH, Feraud M, Jouglet T and Suzuki A. (2006) Glutamine synthetase-glutamate synthase pathway and glutamate dehydrogenase play distinct roles in the sink-source nitrogen cycle in tobacco. Plant Physiol. 140:444-56.
Olvera-Carrillo Y, Campos F, Reyes JL, Garciarrubio A, Covarrubias AA (2010) Functional analysis of the group 4 late embryogenesis abundant proteins reveals their relevance in the adaptive response during water deficit in *Arabidopsis*. Plant Physiol 154(1):373-390. doi:10.1104/pp.110.158964.
Patro L, Mohapatra PK, Biswal UC, Biswal B (2014) Dehydration induced loss of photosynthesis in *Arabidopsis* leaves during senescence is accompanied by the reversible enhancement in the activity of cell wall β-glucosidase. J Photochem Photobiol B 137:49-54. doi: 10.1016/j.jphotobiol.2014.03.018.
Pourtau N, Jennings R, Pelzer E, Pallas J, Wingler A (2006) Effect of sugar-induced senescence on gene expression and implications for the regulation of senescence in *Arabidopsis*. Planta 224(3):556-68. doi:10.1007/s00425-006-0243.
Shi H, Wang B, Yang P, Li Y, Miao F (2016) Differences in sugar accumulation and mobilization between sequential and non-sequential senescence wheat cultivars under natural and drought conditions. PLoS ONE 11(11):e0166155. doi:10.1371/journal.pone.0166155.
Sierro N, Battey JND, Ouadi S, Bakaher N, Bovet L, Willig A, Goepfert S, Peitsch MC, Ivanov NV (2014) The tobacco genome sequence and its comparison with those of tomato and potato. Nature Com 5, 3833. doi.org/10.1038/ncomms4833.
Sonnewald U, Brauer M, von Schaewen A, Stitt M, Willmitzer L (1991) Transgenic tobacco plants expressing yeast-derived invertase in either the cytosol, vacuole or apoplast: a powerful tool for studying sucrose metabolism and sink/source interactions. Plant J 1(1):95-106. doi: 10.1111/j.1365-313X.1991.00095.X.
Stitt M, Wilke I, Feil R, Heldt HW (1988) Coarse control of sucrose-phosphate synthase in leaves: Alterations of the kinetic properties in response to the rate of photosynthesis and the accumulation of sucrose. Planta 174(2):217-30. doi:10.1007/BF00394774.
Uzelac B, Janošević D, Simonović A, Motyka V, Dobrev PI, Budimir S (2016) Characterization of natural leaf senescence in tobacco (*Nicotiana tabacum*) plants grown in vitro. Protoplasma (2): 259-275. doi: 10.1007/S00709-015-0802-9.
Wang W, Hao Q, Tian F, Li Q and Wang W. (2016) Cytokinin-Regulated Sucrose Metabolism in Stay-Green Wheat Phenotype. PLoS One. 11: e0161351. doi: 10.1371/journal.pone.0161351. eCollection 2016.
Wingler A, Masclaux-Daubresse C, Fischer AM (2009) Sugars, senescence, and ageing in plants and heterotrophic organisms. J Exp Bot 60(4): 1063-1066. doi: 10.1093/jxb/erp067.
Yang J, Zhang J, Wang Z, Zhu Q, Liu L (2002) Abscisic acid and cytokinins in the root exudates and leaves and their relationship to senescence and remobilization of carbon reserves in rice subjected to water stress during grain filling. Planta 215(4):645-52. doi:10.1007/s00425-002-0789-2.

(56) References Cited

OTHER PUBLICATIONS

Zhang K, Xia X, Zhang Y, Gan S-S (2012) An ABA-regulated and Golgi-localized protein phosphatase controls water loss during leaf senescence in *Arabidopsis*. Plant J 69(4): 667-678. doi: 10.1111/j.1365-313X.2011.04821.

* cited by examiner

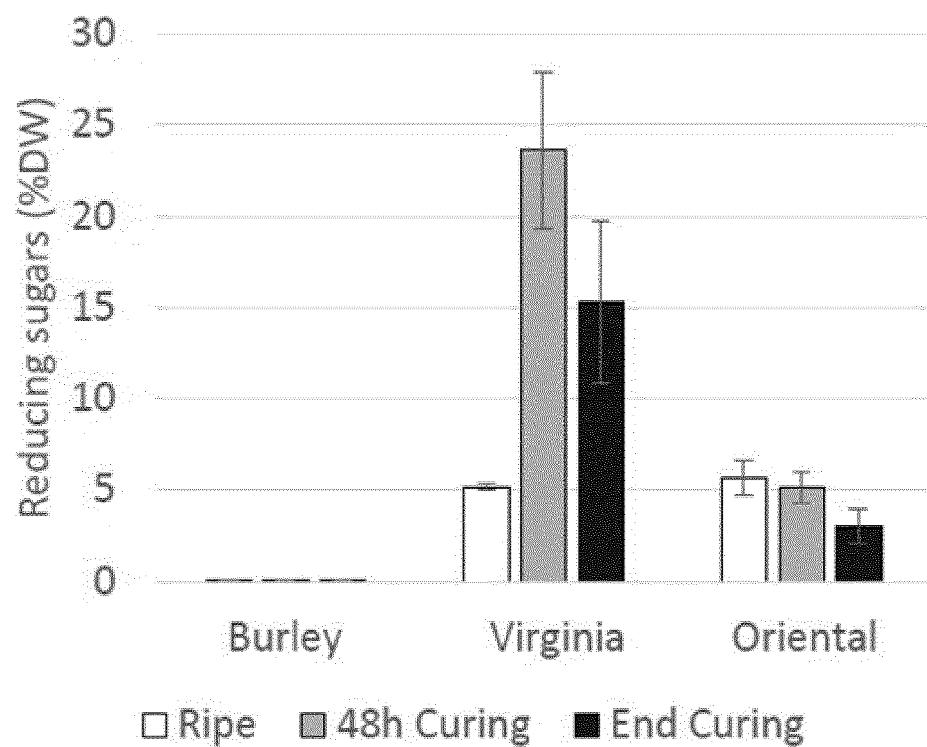
30
25
20
15
10
5
0
Reducing sugars (%DW)
Burley
Virginia
Oriental
Ripe
48h Curing
End Curing

SEQUENCE LISTING

<160> NUMBER OF SEQ ID NOS: 24

<210> SEQ ID NO 1
<211> LENGTH: 4384
<212> TYPE: DNA
<213> ORGANISM: Nicotiana tabacum
<220> FEATURE:
<221> NAME/KEY: misc_feature
<222> LOCATION: (1520)..(1520)
<223> OTHER INFORMATION: n is a, c, g, or t

<400> SEQUENCE: 1
atggcagcta gtggtcttag cattaagaaa agtttggagg aatccatttt ggctcatcca 60
gatgaaattt tggctctcaa gtcaaggtac attactacat ataatgatat taagaactag 120
aggcttatcc aaggttttgt tacatttttg aaattataag tttagaacct aatagtactt 180
ggtagcactt gtttccttat tatctagctg ttgttactgc ttgttgctac tgctttctgt 240
tcatctttcc ttgagcccgg tctatcggaa acaacctctc tattctcaaa gtataaggtt 300
tgcgtacata ctacctcccc agactctact tgtggaattt actgtttttg ttgtgttgtt 360
gtaatctaat atttattaga attttactga tttttcacat atatatatct atgtcccctg 420
tcgaaaattc tatagctcat gttagctaaa tacattagta ccattgtttt taattgtttt 480

```
ggttttggca caggattgaa actgaaggga aaggggtaat gaaaccactt gatctcttga    540
accatttggt ttctgttact agtaagacaa atggagtaaa tattgtacct agtgcacttg    600
tggaagttct cagttgcagc caagaagctg tgattgtacc accaaaacta gcactagctg    660
tacgtccgag gcccggtgta tgggagtact tgtcactgaa tcttaagaca aagaaagtgg    720
ctgaattaag cattcctgaa taccttcaat tgaaagagaa cactgttgat gaaaggtaaa    780
gtattagtct gcgatttcgc tttgtgaaat tgaagttttt gttttgattc ataatgtttt    840
gtgtatcaat tatgttacca gtggaaacat attggagttg gattttgagc catttacaac    900
agttacacca ccaaaaacac tttctgactc tattggcaat ggtttggagt ttcttaatcg    960
ccacattgct tcgaaaatgt ttcatgataa ggagatttcc agatgcctcc ttgacttcct   1020
cagaaaccat aactacaaag gaaaggtaat aaaaaaaagt gtttctttaa acaagttgta   1080
tgattatgtg tatatttcta agtatgttaa cttgaaaaca gtcattgatg gtgaaagaaa   1140
gcattcaaag cctagagagt ttccaacttg ttctgaaaaa agcagaggaa catttgtgca   1200
cattgaatcc agaaactcca tactccaatt ttgaatcaaa gtttgaagag attggcttgg   1260
aaagagggtg gggaaacacc gctgaacgcg tgcaagacac tatcagtcat cttttgcatc   1320
tccttgaggc tcctaacgcg tcttctttgg aaaatttcct tggtagaatc ccattggttt   1380
tcaatgttgt gattctaact ccacatggtt attttgctca agataatgtc ttgggctatc   1440
ctgacactgg tggccaggtt tgtgtccaat attttgcatt cttgatcaag ttctttatac   1500
catttgaacc aacaatcttn aacattcttt ttttggttgt gaaatgttga ataggttgtt   1560
tacattcttg atcaagttcc agctatggag cgtgagatgc ttcatcgtat gaagcttcaa   1620
ggactcgatg atatcatccc tcgcatcctt gttgtaagtg gccttaattt tcctagtttc   1680
atttacacct ctaaatgaaa ttgatctttt ttgttgtttt atatcaggta acaaggctgc   1740
tgcctgatgc agtaggaacc acctgtggcg agcggatgga gaaagtatat ggggcagaac   1800
attctcatat aattcgtgtt ccatttagaa ctgagaaggg aatgttgcgc aaatggatct   1860
cacgattcga agtctggcca tacatggaaa ctttcactga ggttggaaca taaaaacaaa   1920
taaaatccat tggaatgttc cttctgcaat tgaaaatgtc ttgctaactg aagacccatt   1980
tttaaattga tcatcaggat gttgcagaag aacttgtcaa agaattgcaa gctaaaccag   2040
acttgatcat tggaaactac agtgagggaa atcttgctgc ctctttgctt gcgaagaaat   2100
ttggggctac tcagtgtact attgctcatg ccttggaaaa aactaagtat ccaaactctg   2160
accttaattg gaagaagttt gatgacaagt atcatttctc aagtcagttc actgctgatc   2220
tctttgccat gaatcacact gatttcatca tcaccagcac tttccaagaa attgctggaa   2280
ggtaaaagca aatgcacacc atcatagtat ttcatatttt taccettgtt tatactattt   2340
ccattcaccg accccgactt gtttaggatt gagccatagt tgttgttgtt gtttgtttat   2400
actatttcca tttgccgacc acaacttgtt taggactgag gtatagttgt tgttgttggt   2460
ttgttcatat tattttcatt cgctaaccct aacttgtttg ggactgaggc atagtagtag   2520
tagtagttgt tgctattagt ttatactatt tccatttgcc aaccccaact tgtttggtac   2580
tgagacatag ttgttgttgt tgttgtttgt ttatactatt tccatttgcc gaccccaact   2640
tgtttaggac tgaggtatag ttgttgttgt tggtttgttc atattatttt cattcgctaa   2700
ccccaacttg tttgggactg aggcatagta gtagtagtag tagttgttgc tattagttta   2760
tactatttcc atttgccaac cccaacttgt ttggtactga gacatagttg ttgttgttgt   2820
```

```
ttgtttatac tatttcaatt tgtcgacccc aatttgtttg ggaccaaggc atggttgttg   2880
ttgttgtttg tttgttttta ctgtttccat tgatattgga acatttgtta tttgcagcaa   2940
aaacactgta ggacagtatg agagtcatac tgcttttacc atgcctggat tgtaccgagt   3000
agtccatgga atcgattcgt ttgatccaaa gttcaacatt gtctcccctg gggctgatat   3060
gtcaatctac ttcccttaca ctgagaagga gaaaaggcta accaacttcc acccggaaat   3120
tgaagaactc ctctacagtc ctgttgagaa taaggaccac ttgttagtct ccttaatttg   3180
cttttatttc atcccattta tgatcgcttt tatcccaaca gatcgattaa tcatttgtta   3240
tcaacataaa cagatgtgtg ttgaaggacc ggaacaagcc aattctcttt accatggcaa   3300
ggctagatcg cgtgaagaat ctaacagggc tcgtggaatg gtatgctaag aatgcaaggc   3360
tgagggagct tgttaacctt gtggttgtag gcggagacag aaggaaagaa tccaaagatt   3420
tagaagagca agcagagatg aagaagatgt atgatcttat cgaaacctat aacctgaacg   3480
gccaattcag gtggatttct tcccaaatga atcgtgtgag gaacggagaa ctctatcgtt   3540
acattgcaga cacgaggggt gctttcgttc aaccagcatt ctacgaggct tttggtttga   3600
cagttgtaga gtctatgact tgtggtttgc caacttttgc tacttgtaat ggtggaccat   3660
ttgagattat agtgaatgga aaatctggtt tccatattga tcctaatcaa ggtgacaagg   3720
ctgctgatat gttggtaaat ttctttgaaa aatctaaaga agatccaagt tattgggatg   3780
ctatttccaa gggaggtctg caacgtattc ttgaaaagta agcttttgca tttgattagc   3840
acaagtgcac aaccaagatt taacttttga acaaactaaa actaaccctt ttttgtattt   3900
tcttttgcta ggtatacatg gcaaatttat tcacagaaag tgatcacact atctgggatt   3960
tatggattct ggaagtatgc aaccaagaat gataaagttg ctagtgcaaa gaagcgctat   4020
cttgagatgt tttatgaact tggatttaag aaatcagtaa gtgtcaattt taaaggggaa   4080
ccttggatca acggttaagt tgtctttgtg caacctatag gtcaggggtt tgagccgtag   4140
aagtagccac taatatttac attagggtag actgtgtaca tatcacaccc cttggggtac   4200
ggccctttcc tggatcctgt atgaacgcgg gatgccttgt gcaccgggct gtattttttt   4260
ttttagtgtc acttctgtat tttgtttgag cttgtttata aagtttggaa atctgctgct   4320
aatttgtata tttgttggtt gtgtatttca ggctgagaaa gttccattgg ctattgatga   4380
atag                                                                4384
```

<210> SEQ ID NO 2
<211> LENGTH: 803
<212> TYPE: PRT
<213> ORGANISM: Nicotiana tabacum

<400> SEQUENCE: 2

```
Met Ala Ala Ser Gly Leu Ser Ile Lys Lys Ser Leu Glu Glu Ser Ile
1               5                   10                  15

Leu Ala His Pro Asp Glu Ile Leu Ala Leu Lys Ser Arg Ile Glu Thr
            20                  25                  30

Glu Gly Lys Gly Val Met Lys Pro Leu Asp Leu Leu Asn His Leu Val
        35                  40                  45

Ser Val Thr Ser Lys Thr Asn Gly Val Asn Ile Val Pro Ser Ala Leu
    50                  55                  60

Val Glu Val Leu Ser Cys Ser Gln Glu Ala Val Ile Val Pro Pro Lys
65                  70                  75                  80

Leu Ala Leu Ala Val Arg Pro Arg Pro Gly Val Trp Glu Tyr Leu Ser
                85                  90                  95
```

```
Leu Asn Leu Lys Thr Lys Lys Val Ala Glu Leu Ser Ile Pro Glu Tyr
            100                 105                 110

Leu Gln Leu Lys Glu Asn Thr Val Asp Glu Ser Gly Asn Ile Leu Glu
        115                 120                 125

Leu Asp Phe Glu Pro Phe Thr Thr Val Thr Pro Pro Lys Thr Leu Ser
    130                 135                 140

Asp Ser Ile Gly Asn Gly Leu Glu Phe Leu Asn Arg His Ile Ala Ser
145                 150                 155                 160

Lys Met Phe His Asp Lys Glu Ile Ser Arg Cys Leu Leu Asp Phe Leu
                165                 170                 175

Arg Asn His Asn Tyr Lys Gly Lys Ser Leu Met Val Lys Glu Ser Ile
            180                 185                 190

Gln Ser Leu Glu Ser Phe Gln Leu Val Leu Lys Lys Ala Glu Glu His
        195                 200                 205

Leu Cys Thr Leu Asn Pro Glu Thr Pro Tyr Ser Asn Phe Glu Ser Lys
    210                 215                 220

Phe Glu Glu Ile Gly Leu Glu Arg Gly Trp Gly Asn Thr Ala Glu Arg
225                 230                 235                 240

Val Gln Asp Thr Ile Ser His Leu Leu His Leu Leu Glu Ala Pro Asn
                245                 250                 255

Ala Ser Ser Leu Glu Asn Phe Leu Gly Arg Ile Pro Leu Val Phe Asn
            260                 265                 270

Val Val Ile Leu Thr Pro His Gly Tyr Phe Ala Gln Asp Asn Val Leu
        275                 280                 285

Gly Tyr Pro Asp Thr Gly Gly Gln Val Val Tyr Ile Leu Asp Gln Val
    290                 295                 300

Pro Ala Met Glu Arg Glu Met Leu His Arg Met Lys Leu Gln Gly Leu
305                 310                 315                 320

Asp Asp Ile Ile Pro Arg Ile Leu Val Val Thr Arg Leu Leu Pro Asp
                325                 330                 335

Ala Val Gly Thr Thr Cys Gly Glu Arg Met Glu Lys Val Tyr Gly Ala
            340                 345                 350

Glu His Ser His Ile Ile Arg Val Pro Phe Arg Thr Glu Lys Gly Met
        355                 360                 365

Leu Arg Lys Trp Ile Ser Arg Phe Glu Val Trp Pro Tyr Met Glu Thr
    370                 375                 380

Phe Thr Glu Asp Val Ala Glu Glu Leu Val Lys Glu Leu Gln Ala Lys
385                 390                 395                 400

Pro Asp Leu Ile Ile Gly Asn Tyr Ser Glu Gly Asn Leu Ala Ala Ser
                405                 410                 415

Leu Leu Ala Lys Lys Phe Gly Ala Thr Gln Cys Thr Ile Ala His Ala
            420                 425                 430

Leu Glu Lys Thr Lys Tyr Pro Asn Ser Asp Leu Asn Trp Lys Lys Phe
        435                 440                 445

Asp Asp Lys Tyr His Phe Ser Ser Gln Phe Thr Ala Asp Leu Phe Ala
    450                 455                 460

Met Asn His Thr Asp Phe Ile Ile Thr Ser Thr Phe Gln Glu Ile Ala
465                 470                 475                 480

Gly Ser Lys Asn Thr Val Gly Gln Tyr Glu Ser His Thr Ala Phe Thr
                485                 490                 495

Met Pro Gly Leu Tyr Arg Val Val His Gly Ile Asp Ser Phe Asp Pro
            500                 505                 510
```

```
Lys Phe Asn Ile Val Ser Pro Gly Ala Asp Met Ser Ile Tyr Phe Pro
        515                 520                 525

Tyr Thr Glu Lys Glu Lys Arg Leu Thr Asn Phe His Pro Glu Ile Glu
    530                 535                 540

Glu Leu Leu Tyr Ser Pro Val Glu Asn Lys Asp His Leu Cys Val Leu
545                 550                 555                 560

Lys Asp Arg Asn Lys Pro Ile Leu Phe Thr Met Ala Arg Leu Asp Arg
                565                 570                 575

Val Lys Asn Leu Thr Gly Leu Val Glu Trp Tyr Ala Lys Asn Ala Arg
            580                 585                 590

Leu Arg Glu Leu Val Asn Leu Val Val Val Gly Gly Asp Arg Arg Lys
        595                 600                 605

Glu Ser Lys Asp Leu Glu Glu Gln Ala Glu Met Lys Lys Met Tyr Asp
    610                 615                 620

Leu Ile Glu Thr Tyr Asn Leu Asn Gly Gln Phe Arg Trp Ile Ser Ser
625                 630                 635                 640

Gln Met Asn Arg Val Arg Asn Gly Glu Leu Tyr Arg Tyr Ile Ala Asp
                645                 650                 655

Thr Arg Gly Ala Phe Val Gln Pro Ala Phe Tyr Glu Ala Phe Gly Leu
            660                 665                 670

Thr Val Val Glu Ser Met Thr Cys Gly Leu Pro Thr Phe Ala Thr Cys
        675                 680                 685

Asn Gly Gly Pro Phe Glu Ile Ile Val Asn Gly Lys Ser Gly Phe His
    690                 695                 700

Ile Asp Pro Asn Gln Gly Asp Lys Ala Ala Asp Met Leu Val Asn Phe
705                 710                 715                 720

Phe Glu Lys Ser Lys Glu Asp Pro Ser Tyr Trp Asp Ala Ile Ser Lys
                725                 730                 735

Gly Gly Leu Gln Arg Ile Leu Glu Lys Tyr Thr Trp Gln Ile Tyr Ser
            740                 745                 750

Gln Lys Val Ile Thr Leu Ser Gly Ile Tyr Gly Phe Trp Lys Tyr Ala
        755                 760                 765

Thr Lys Asn Asp Lys Val Ala Ser Ala Lys Lys Arg Tyr Leu Glu Met
    770                 775                 780

Phe Tyr Glu Leu Gly Phe Lys Lys Ser Ala Glu Lys Val Pro Leu Ala
785                 790                 795                 800

Ile Asp Glu
```

<210> SEQ ID NO 3
<211> LENGTH: 3926
<212> TYPE: DNA
<213> ORGANISM: Nicotiana tabacum

<400> SEQUENCE: 3

```
atggcaggca gtggtcttag cattaaggaa agtttggagg aatccatttt ggctcatcca      60

gatgaaattt tggctctcaa gtcaaggtac attactgcat aatgatatta agacctagaa     120

gcggatccaa gattttgtta catttttgaa attataagtt tagaatctaa tatttgttat     180

cgcttgtttc cttattatct tgctgttgtt actgcctgtt gctactagtt tctgttcatc     240

cttccttgag ctgagtttct atcggaaaca acctctctac tctcaaagta ggaataagtt     300

atgcgtacac actaccctcc ccagactcca cttgtgtaat ttactgagtt tgttgttgtt     360

gttgttgtaa tctaatactt gttagaattt tactgatttt tcacatatat atctatgacc     420

catgtcgaaa atactatagc tcatgtgcta aatacattag taccattgtt ttgtaattgt     480
```

```
tttggttttg gaacaggatt gaaactgaag ggaaaggggt aatgaaacca gttgatctct    540
tgaaccattt ggtttctgtt actagtaaaa caaatggagt aaatgttgta cctagtgcac    600
ttgtggaagt tctcagttgc agccaagaag ctgtgattgt accaccaaaa ctagcactag    660
ctgtacgtcc gaggcccggt gtatgggagt acttgtcact gaatcttaag acaaagaaag    720
tggctgaatt gagcattcct gagtaccttc aattgaaaga gaatactgtt gatgaaaggt    780
aaagtaatag tctgcgattt cgctttgtga aattgaagtt ttttgtttga ttcttaatgt    840
tttgtgtatc aattatgtta ccagtggaaa catcttggag ttggattttg agccatttac    900
aactgttaca acaccaaaaa cactttctga ctctattggc aatggtttgg agtttcttaa    960
tcgccacatt gcttcgaaaa tgtttcttga taaggagatt gccaagtgcc tccttgactt   1020
tctcagaaac cataactaca aaggaaaggt agtaaaaaaa gtgtttcttt aaacaagttg   1080
tatgattatg tgtgtatttc taaatatgtc aatttgaaaa cagtcattga tggtgaaaga   1140
aagcattcaa agcctggaga gtttccaact tgttctgaaa aaagcagagg aatatttgca   1200
cacactgaat ccagaaactc catactccaa atttgaatcc aagtttgaag agattggctt   1260
ggaaagaggg tggggaaaca ccgctgaacg cgtgcaagac accattagtc atcttttgca   1320
tctccttgag gctcctaacg cgtcttcctt ggaaaatttc cttggtagaa tcccattggt   1380
tttcaatgtt gtgattctca ccccacatgg ttattttgct caagataatg tcttgggcta   1440
tcctgacact ggtggccagg tttgtgtccg atataacata tcaagaaatt ttgcattctt   1500
gatcatgttc tttataccat ttgaaccaac attctttttt tggttgtgaa atgttgaata   1560
ggttgtttac attcttgatc aagttccagc tatggagcgt gagatgcttc atcgtatgaa   1620
gcttcaagga ctcgacgata tcatccctcg catccttgtt gtaagtgccc ttaattttcc   1680
tggtttggtt tacctctaaa tgaaattgat tttctggctt tctaactttt ttggattgat   1740
ctttttgttg ttttatatca ggtaactagg ctgctgcctg atgctgtagg aaccacttgt   1800
ggcgagtgga tggagaaagt atatggggca gaacattctc atataattcg tgttccattt   1860
agaactgaga aaggaatgtt gcgcaaatgg atctcacgat tcgaagtctg gccatacatg   1920
gaaactttca ctgaggttgg aacataaaaa caaataaaaa tcattggaat gttcttctgc   1980
atttgaaaat gtcttgctaa ctaaagactc atttttaaat taatcatcag gatgttgcag   2040
aagaacttgt caaagaattg caagctaaac cagacttgat aattggaaac tacagtgagg   2100
gaaatcttgc tgcctcattg cttgctaaga aatttggggc tactcagtgt actattgctc   2160
atgccttgga aaaaactaag tatccaaact ctgaccttaa ttggaagaag tttgatgaca   2220
agtatcattt ctcaagtcag ttcactgctg atctttttgc catgaatcac actgatttca   2280
ttatcaccag cactttccaa gaaattgctg gaaggtaaaa gcaaatgcac accatcatag   2340
tatttcatat ttttacccta gtttatacta tttccatttg tcaactccaa cttgtttggg   2400
attgaaccat agttgttgtt tgtttatact atttccattc gccgaccccca acttatttgg   2460
gactgagaca taattgttgt tattattgtt tgtttgttta tactatttcc attctcagac   2520
cccaacttct ttgggactga gccgtagatt gttgttgttg ttgttgttgt tgtttgttta   2580
tgctatttcc gttcaccgac cccaacttat ttgggactga ggtgtagaag tagtcgttgt   2640
tgtttgttta tacgacttcc aattgatatt cgaatgtttt tatttttgca gcaagaacac   2700
tgtaggacag tatgagagtc atactgcttt taccatgcct ggattgtatc gagtagtcca   2760
tggaatcaat tcgtttgatc caaagttcaa cattgtctcc cctggggctg atatgtcaat   2820
```

```
ctacttccct tacactgaga aggagaaaag actaaccaac ttccacccgg aaattgaaga   2880

actcctctac agtcctgttg agaataagga ccacttgtta gtcttcttta tttcattcat   2940

ttttctacac cttttttttc aacagattga ttgattggtt cttatcaacg taaacagatg   3000

tgtgttgaag gaccagaaca agccaattct ctttaccatg gcaaggctag atcgcgtgaa   3060

gaatctaaca gggctcgtgg aatggtatgc aaagaatgca aggctaaggg agctcgttaa   3120

ccttgtggtt gtaggcggag acagaaggaa agaatccaaa gatttagaag agcaagcaga   3180

gatgaagaag atgtatgatc ttatcgaaac atacaacctg aatggccaat tcaggtggat   3240

ttcttcccaa atgaatcgtg tgaggaacgg agaactttat cgatacattg cagacacgag   3300

gggtgctttc gttcaaccag cattttatga ggcatttggt ttgacagttg ttgagtctat   3360

gacttgtggt ttgccaactt ttgctacttg taatggtgga ccatttgaga ttatagtgaa   3420

tggaaaatct ggtttccata ttgatcctaa tcaaggtgac aaggctgctg atatgttggt   3480

taatttcttc gaaaaatcta aagaagatcc aagttattgg gatactattt ccaagggtgg   3540

tctgcagcgt attcttgaaa agtaagcttt tgcatttgat tagcacaagt gtacaaccaa   3600

gatttaactt atgaacaaac taaaactaac ccttttttta ttttcttttg ctaggtatac   3660

atggcaaatt tattcacaga aagtgatcac attatctggg atttatggat tctggaaata   3720

tgcaaccaag aatgacaaag ttgctagtgc gaagaagcgc tatcttgaaa tgttttatga   3780

atttgggttt aagaaatcag taagtgtcac ttctgtattt tgtttgagct tgtttgtaaa   3840

gtttggcaat cttctgctaa tttgtactat atttgttgac ttgtgcattt caggctgaga   3900

aagttccatt ggctattgat gaatag                                        3926
```

```
<210> SEQ ID NO 4
<211> LENGTH: 803
<212> TYPE: PRT
<213> ORGANISM: Nicotiana tabacum

<400> SEQUENCE: 4

Met Ala Gly Ser Gly Leu Ser Ile Lys Glu Ser Leu Glu Glu Ser Ile
1               5                   10                  15

Leu Ala His Pro Asp Glu Ile Leu Ala Leu Lys Ser Arg Ile Glu Thr
            20                  25                  30

Glu Gly Lys Gly Val Met Lys Pro Val Asp Leu Leu Asn His Leu Val
        35                  40                  45

Ser Val Thr Ser Lys Thr Asn Gly Val Asn Val Val Pro Ser Ala Leu
    50                  55                  60

Val Glu Val Leu Ser Cys Ser Gln Glu Ala Val Ile Val Pro Pro Lys
65                  70                  75                  80

Leu Ala Leu Ala Val Arg Pro Arg Pro Gly Val Trp Glu Tyr Leu Ser
                85                  90                  95

Leu Asn Leu Lys Thr Lys Lys Val Ala Glu Leu Ser Ile Pro Glu Tyr
            100                 105                 110

Leu Gln Leu Lys Glu Asn Thr Val Asp Glu Ser Gly Asn Ile Leu Glu
        115                 120                 125

Leu Asp Phe Glu Pro Phe Thr Thr Val Thr Thr Pro Lys Thr Leu Ser
    130                 135                 140

Asp Ser Ile Gly Asn Gly Leu Glu Phe Leu Asn Arg His Ile Ala Ser
145                 150                 155                 160

Lys Met Phe Leu Asp Lys Glu Ile Ala Lys Cys Leu Leu Asp Phe Leu
                165                 170                 175
```

```
Arg Asn His Asn Tyr Lys Gly Lys Ser Leu Met Val Lys Glu Ser Ile
            180                 185                 190

Gln Ser Leu Glu Ser Phe Gln Leu Val Leu Lys Lys Ala Glu Glu Tyr
        195                 200                 205

Leu His Thr Leu Asn Pro Glu Thr Pro Tyr Ser Lys Phe Glu Ser Lys
    210                 215                 220

Phe Glu Glu Ile Gly Leu Glu Arg Gly Trp Gly Asn Thr Ala Glu Arg
225                 230                 235                 240

Val Gln Asp Thr Ile Ser His Leu Leu His Leu Leu Glu Ala Pro Asn
                245                 250                 255

Ala Ser Ser Leu Glu Asn Phe Leu Gly Arg Ile Pro Leu Val Phe Asn
            260                 265                 270

Val Val Ile Leu Thr Pro His Gly Tyr Phe Ala Gln Asp Asn Val Leu
        275                 280                 285

Gly Tyr Pro Asp Thr Gly Gly Gln Val Val Tyr Ile Leu Asp Gln Val
    290                 295                 300

Pro Ala Met Glu Arg Glu Met Leu His Arg Met Lys Leu Gln Gly Leu
305                 310                 315                 320

Asp Asp Ile Ile Pro Arg Ile Leu Val Val Thr Arg Leu Leu Pro Asp
                325                 330                 335

Ala Val Gly Thr Thr Cys Gly Glu Trp Met Glu Lys Val Tyr Gly Ala
            340                 345                 350

Glu His Ser His Ile Ile Arg Val Pro Phe Arg Thr Glu Lys Gly Met
        355                 360                 365

Leu Arg Lys Trp Ile Ser Arg Phe Glu Val Trp Pro Tyr Met Glu Thr
    370                 375                 380

Phe Thr Glu Asp Val Ala Glu Glu Leu Val Lys Glu Leu Gln Ala Lys
385                 390                 395                 400

Pro Asp Leu Ile Ile Gly Asn Tyr Ser Glu Gly Asn Leu Ala Ala Ser
                405                 410                 415

Leu Leu Ala Lys Lys Phe Gly Ala Thr Gln Cys Thr Ile Ala His Ala
            420                 425                 430

Leu Glu Lys Thr Lys Tyr Pro Asn Ser Asp Leu Asn Trp Lys Lys Phe
        435                 440                 445

Asp Asp Lys Tyr His Phe Ser Ser Gln Phe Thr Ala Asp Leu Phe Ala
    450                 455                 460

Met Asn His Thr Asp Phe Ile Ile Thr Ser Thr Phe Gln Glu Ile Ala
465                 470                 475                 480

Gly Ser Lys Asn Thr Val Gly Gln Tyr Glu Ser His Thr Ala Phe Thr
                485                 490                 495

Met Pro Gly Leu Tyr Arg Val Val His Gly Ile Asn Ser Phe Asp Pro
            500                 505                 510

Lys Phe Asn Ile Val Ser Pro Gly Ala Asp Met Ser Ile Tyr Phe Pro
        515                 520                 525

Tyr Thr Glu Lys Glu Lys Arg Leu Thr Asn Phe His Pro Glu Ile Glu
    530                 535                 540

Glu Leu Leu Tyr Ser Pro Val Glu Asn Lys Asp His Leu Cys Val Leu
545                 550                 555                 560

Lys Asp Gln Asn Lys Pro Ile Leu Phe Thr Met Ala Arg Leu Asp Arg
                565                 570                 575

Val Lys Asn Leu Thr Gly Leu Val Glu Trp Tyr Ala Lys Asn Ala Arg
            580                 585                 590

Leu Arg Glu Leu Val Asn Leu Val Val Val Gly Gly Asp Arg Arg Lys
```

```
        595                 600                 605

Glu Ser Lys Asp Leu Glu Glu Gln Ala Glu Met Lys Lys Met Tyr Asp
    610                 615                 620

Leu Ile Glu Thr Tyr Asn Leu Asn Gly Gln Phe Arg Trp Ile Ser Ser
625                 630                 635                 640

Gln Met Asn Arg Val Arg Asn Gly Glu Leu Tyr Arg Tyr Ile Ala Asp
                645                 650                 655

Thr Arg Gly Ala Phe Val Gln Pro Ala Phe Tyr Glu Ala Phe Gly Leu
            660                 665                 670

Thr Val Val Glu Ser Met Thr Cys Gly Leu Pro Thr Phe Ala Thr Cys
        675                 680                 685

Asn Gly Gly Pro Phe Glu Ile Ile Val Asn Gly Lys Ser Gly Phe His
    690                 695                 700

Ile Asp Pro Asn Gln Gly Asp Lys Ala Ala Asp Met Leu Val Asn Phe
705                 710                 715                 720

Phe Glu Lys Ser Lys Glu Asp Pro Ser Tyr Trp Asp Thr Ile Ser Lys
                725                 730                 735

Gly Gly Leu Gln Arg Ile Leu Glu Lys Tyr Thr Trp Gln Ile Tyr Ser
            740                 745                 750

Gln Lys Val Ile Thr Leu Ser Gly Ile Tyr Gly Phe Trp Lys Tyr Ala
        755                 760                 765

Thr Lys Asn Asp Lys Val Ala Ser Ala Lys Lys Arg Tyr Leu Glu Met
    770                 775                 780

Phe Tyr Glu Phe Gly Phe Lys Lys Ser Ala Glu Lys Val Pro Leu Ala
785                 790                 795                 800

Ile Asp Glu
```

<210> SEQ ID NO 5
<211> LENGTH: 4532
<212> TYPE: DNA
<213> ORGANISM: Nicotiana tabacum

<400> SEQUENCE: 5

```
atggctgaac gtgctctgac tcgtgttcac agccttcgtg aacgtcttga tgccactttg     60

gctgcacatc gcaatgagat attgctgttt ctttcaaggt attgcctaag tagtgttctt    120

gtttcctaca aaagattcag ttggtgttca aaaaacgata tgtgatttga tttatctgcc    180

taagtcttgg tagtcataat tatccggtac ctgtgctggt gcgagttagc tggttcggaa    240

actactctta tgaaaacgag agatttagtt ggtgttgtct gcaattctgt agtatggact    300

attaagcaga tagatcatgt ttgatatcga aaaggaatgt atatgtgatg ttacttgaac    360

tggttttggt tattacagga ttgaaagcca tggaaaaggg atcttgaaac ctcaccagct    420

attggctgag ttcgatgcaa ttcgccaaga tgacaaaaag aagctgaatg atcatgcatt    480

tgaagaactc ctgaaatcta ctcaggtaat tttgattttg gctaaatgtg ttaccaagct    540

gaatgatcat gcatttgagt ttgtgtccga ctactacaat gatatgttat accaggaagc    600

gattgttctg ccaccttggg ttgcacttgc cattcgtttg aggcctggtg tgtgggaata    660

tgtccgtgtg aatgttaatg ctctagtcgt tgaggagctg accgtccctg agtatttgca    720

ttttaaggaa gaacttgttg atggaacgta agttttagtc tcttatttga tactatgtta    780

gagaataggc agtggattca atttatcagt gttgtttttt acctaatgca gctccaatgg    840

aaatttcgtt ctcgagttgg attttgagcc cttcactgca tcctttccta aaccgaccct    900

caccaaatct attgggaatg gagttgaatt cctcaatagg cacctttctg cgaaaatgtt    960
```

```
ccatgacaag gaaagcatga ccccgcttct tgaatttctt cgggttcaca attataaggg   1020
caaggtaact ttgttattcc cattcatata tatgttcagt ttgtgcttat catgcgccca   1080
atgatgtatg aatatgtact aaaggataga tgtacgattt cgtttgcaga caatgatgct   1140
gaatgacaga atacagaatt taaccactct gcaaaatgtc ctaaggaagg cagaggaata   1200
ccttattatg cttccccctg aaactccatt ttccgaattc gaacacaagt tccaagaaat   1260
tggattggag aagggatggg gcgacactgc ggagcgcgtg ctagagatga tatgcatgct   1320
tcttgatcta cttgaggctc ccgactcctg tactcttgag aagttcctag ggagaattcc   1380
tatggtgttc aacgtggtta tcctttcccc ccatggatat ttcgcccagg aaaatgtctt   1440
gggttatccc gacactggtg gccaggtgca ttactttagt ctttgtccgt gagtctatgt   1500
tgctcagatc ctctacaatg ccactgtacc cgtgtaggat actccaaata taatgcattt   1560
ttggaggatc tgtcaccggt gcaatggcat tttggaggtc ggagcaacaa acaactgcta   1620
gtatgcttct aaagcttgct tccataaatg ctaaggtcct tcacccgtaa tgtgcaggtt   1680
gtctacatat tagatcaagt tccagccttg gagcgtgaaa tgcttaaacg cctaaaggag   1740
caaggacttg atataacacc gcgtattctt attgttagta tttcttgtac ttgtaattgc   1800
tgcggattac acaaaatttt ctctttattg gcaacttatc ttgatattat tcccaggtta   1860
ctcgtctgct gcctgatgca gttggaacaa cttgtggtca gcggcttgag aaggtgtatg   1920
gagccgagca ctcacatatt cttagggtcc cctttaggac cgagaagggc attgttcgca   1980
aatggatatc tcgctttgaa gtgtggccat acatggagac tttcactgag gtgacactaa   2040
gcttccttgt atttgtctat cttctaattg gtattaggaa caatttgcta attattaacg   2100
ctttggcttt tcgtacatca ggatgttgca aaagaacttg ctgcagaact gcaggccaag   2160
ccagatttga taattggcaa ctatagcgag ggaaatcttg tggcttcatt gctggctcac   2220
aagttaggcg taacgcaggt ctgtgttatt tttcacctct tataaatctg attgtatttc   2280
cattagtctg gaactaaaag tactaaaatt ttcttttctt cgctgtgtta tttgccttct   2340
gcagtgcacc attgcccatg cattggagaa aacaaagtat cctgattctg acatctactg   2400
gaaaaaattt gacgaaaaat accatttctc gtcccagttt accgctgatc ttattgcaat   2460
gaatcacacc gattttatca tcaccagcac tttccaggag atagcaggaa ggtataacat   2520
caattgctaa ttcggttgca gtaacatttt gttcgatttc ttccccttat gcttaaccta   2580
ataccctaat gaattttcca gcaaggacac tgtcggacag tacgagagtc accaggcatt   2640
cacaatgcct ggattgtaca gagtcgttca cggcattgat gtgttcgatc ccaaattcaa   2700
cattgtctca cctggagctg atataaacct gtatttccca tattccgaga aggaaaagag   2760
attgacagca cttcacccag aaattgagga gcttctgtac agtgatgttg agaacgagga   2820
acatctgtaa gtttctaact tactcgtacc gtcagtggca gagccagaat tttcattaaa   2880
atggggtcaa aatataaaga cataaattca caaagaagcc aaggggtgtc aatatgtagt   2940
ataaatatat taaaaaaatt acctagctac acaatgtaat tttccgacaa aggggtatcg   3000
gttgcacttc ttgaatacat gtggctctgc cactgggtac agttacaaag tcctgttacc   3060
tatgtagatg agcttgtgct gaacatgttg tgattttggt aggtgtgtgc taaaggacag   3120
gaataagcca atcttattca caatggcgag attggatcgt gtgaagaact taaccggact   3180
tgttgagtgg tacgccaaga acgcacggct aagggagttg gttaaccttg ttgtcgttgg   3240
tggagaccga aggaaggaat ccaaagattt ggaagagcaa gcagagatga agaagatgta   3300
```

```
tgagctaata aagactcaca acttaaatgg ccaattcaga tggatttctt cacagatgaa   3360
ccgagtaagg aacggcgaac tctaccgata cattgccgac actaggggag ctttcgtgca   3420
gcctgcattc tatgaggctt tcggtttgac tgttgttgag gccatgacct gtggtttgcc   3480
tacatttgca actaatcatg gcggtccagc tgagatcatc gttaacggaa aatccggctt   3540
ccatatcgat ccatatcacg gtgagcaagc tgctgatctg ctagctgatt tctttgagaa   3600
atgtaagacg gaaccttctc attgggaaac tatttcaacc ggtggcctga agcgcatcca   3660
agagaagtaa gcaactcttt cttgactcta gtcattcaaa ttaacttggg atttgaggca   3720
tagttgattg ataatttatc gcgtctctac tactatatac aggtacacgt ggcaaatcta   3780
ctcggagaga ttattgacgt tggctgctgt ttacggtttc tggaaacatg tttctaagct   3840
tgatcgtcta gaaatccgtc gatatctaga aatgttttat gctctcaaat accggaagat   3900
ggtgagttct tctgcttcct gctcttctca tagtgtttaa tatacacttg attgattgca   3960
ttcacttaga ctaagttgct cggacacggg tgtggatgtc cgacacgagt gcggatctag   4020
agttcagatc cttcaagatg taaattataa gattcgggga tatggatcct agtacggata   4080
cgggtgcgag aatccggcta aaaataattt taaaaaaaat tatctctaaa ttatgagata   4140
ttatgtggaa tacttacgta taacttgtaa agtgtagatt ttttttaatt ctcaagttgt   4200
agattagtaa atgattgatt tcctagataa gtatgctatt ttcttcaaat ttactcttct   4260
gatttcgaaa atcaaattgt atctcgtctc gaatttttcc gtccgttatg gtcaaagtac   4320
ccaaaatcgt ttgaccaaat cggtacggat cccataccca cacccacact agtgtcgtat   4380
tgacacgggt gccgcaccta aactgctatg tcggagcaac ttagcactta gagaatcatt   4440
gatgttaaat tttcttaatt cttgaatctg ctaatgaaga ttttatcttg gtttttgttt   4500
aggctgaagc tgttccattg gctgctgaat ga                                 4532
```

<210> SEQ ID NO 6
<211> LENGTH: 805
<212> TYPE: PRT
<213> ORGANISM: Nicotiana tabacum

<400> SEQUENCE: 6

```
Met Ala Glu Arg Ala Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Asp Ala Ile Arg Gln Asp Asp Lys Lys Lys Leu Asn Asp
    50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Thr Val
            100                 105                 110

Pro Glu Tyr Leu His Phe Lys Glu Glu Leu Val Asp Gly Thr Ser Asn
        115                 120                 125

Gly Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160
```

```
Asn Arg His Leu Ser Ala Lys Met Phe His Asp Lys Glu Ser Met Thr
                165                 170                 175

Pro Leu Leu Glu Phe Leu Arg Val His Asn Tyr Lys Gly Lys Thr Met
            180                 185                 190

Met Leu Asn Asp Arg Ile Gln Asn Leu Thr Thr Leu Gln Asn Val Leu
        195                 200                 205

Arg Lys Ala Glu Glu Tyr Leu Ile Met Leu Pro Pro Glu Thr Pro Phe
    210                 215                 220

Ser Glu Phe Glu His Lys Phe Gln Glu Ile Gly Leu Glu Lys Gly Trp
225                 230                 235                 240

Gly Asp Thr Ala Glu Arg Val Leu Glu Met Ile Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Leu Lys Glu Gln Gly Leu Asp Ile Thr Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Tyr Gly Ala Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Thr Glu Asp Val Ala Lys Glu Leu Ala Ala
385                 390                 395                 400

Glu Leu Gln Ala Lys Pro Asp Leu Ile Ile Gly Asn Tyr Ser Glu Gly
                405                 410                 415

Asn Leu Val Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Trp Lys Lys Phe Asp Glu Lys Tyr His Phe Ser Ser Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Gln Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Ile
        515                 520                 525

Asn Leu Tyr Phe Pro Tyr Ser Glu Lys Glu Lys Arg Leu Thr Ala Leu
    530                 535                 540

His Pro Glu Ile Glu Glu Leu Leu Tyr Ser Asp Val Glu Asn Glu Glu
545                 550                 555                 560

His Leu Cys Val Leu Lys Asp Arg Asn Lys Pro Ile Leu Phe Thr Met
                565                 570                 575
```

```
Ala Arg Leu Asp Arg Val Lys Asn Leu Thr Gly Leu Val Glu Trp Tyr
            580                 585                 590

Ala Lys Asn Ala Arg Leu Arg Glu Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val Asn Gly
    690                 695                 700

Lys Ser Gly Phe His Ile Asp Pro Tyr His Gly Glu Gln Ala Ala Asp
705                 710                 715                 720

Leu Leu Ala Asp Phe Phe Glu Lys Cys Lys Thr Glu Pro Ser His Trp
                725                 730                 735

Glu Thr Ile Ser Thr Gly Gly Leu Lys Arg Ile Gln Glu Lys Tyr Thr
            740                 745                 750

Trp Gln Ile Tyr Ser Glu Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Tyr Arg Lys Met Ala Glu Ala Val
785                 790                 795                 800

Pro Leu Ala Ala Glu
                805
```

<210> SEQ ID NO 7
<211> LENGTH: 5901
<212> TYPE: DNA
<213> ORGANISM: Nicotiana tabacum

<400> SEQUENCE: 7

```
atgcttttta tgggagtaaa ttttatggcc ggtcattcaa ctttgtgttc attacgcaaa      60

agtcattttt cttggtgttt attacgcaag tcatttttct ttttttttg ttacgtaaaa      120

atcattcaac tatgtgttta ttatctaaaa ttcaattttt tttttccttt tgttacacaa      180

aaatcatttt actttactct atttatcaca aaagtcacct tggccagatt ttataatagg      240

cttttatctt ttgttacaca aaaattattt tactttactc tatttatcac aaaagtcacc      300

ttggccagat tttataatag gcttttatct tttgttacac aaaaattatt ttactttact      360

ctatttatca caaaagtcac cttggccaga ttttacaata cttttacctt aaaagactat      420

tatgcccttg acattataaa tcctctcatt tatataatac cttctatatg atacactata      480

taatatattt ttacctaggt attttactta taattaaaat aatattaaat tattttattt      540

atctatttta taatatattc atacatttaa ttttttcatg gcaaatcact ttgtttaatc      600

atatttaaac atgaacaaat tttaaatatc aaaaaaataa aaaaataaaa aaaatattta      660

tttgaaataa taacaaacag atttgtttaa caaatgatag ttttttttta tagtcaataa      720

aatttttaaa aaaattcaaa gatatttgtt tttaatatta atatttttaa agctttatct      780
```

```
gttaatatta tttatttgaa agtattaatc tgatgtgtca ttgtgttaaa tgtgagtatt    840
ttatttattg gattaatgag tatggcttgg ctgataaaaa gctttgattt tataattttc    900
attaaaaata ttttattaag ctagtacctg acaaatttaa tatcttgaaa attaacgtta    960
agaaaaaatt aaatataaaa atatattata aaaataataa ataaataata tcaagttatt   1020
ttaattataa ataaaataca tggttaaaaa tatattatat agcatataat atagaaggta   1080
ttacataaat gagatgattt aaagggcata atagactttt caggtgaatg atttgtaaaa   1140
tatggttaaa gtgattattg tgataattag agcatagtaa aataattttt atgtaacaaa   1200
agaaaaaaaa aatgactttt gggtaatgaa cataaatttg aataactttt acgtaacaaa   1260
agaataaaat aaattttgga taataaacat aaaattgaat gaccacctat aaaatttatt   1320
atttttttgg gctcttcttg atttgatttt ttagtttagc ctttgcagta atcttggttg   1380
tcacgcgtag cgttgtgctt tcgccacata agtatttagt agacttaatt aatgtcatta   1440
tatcggttgg tgtggtttta attacttaac tgtactatta tattaggtgg aaggtttgaa   1500
aatttatagt agtaacattc tagatcattg aaaatattgg tgtttcagtg actttttagt   1560
atgtcatttt cattttctaa gtggttgtac taatatagta tattaaaatt ttgattggtt   1620
gagaaacaat ctctctcacc tacacggtac gggtaaggta tgcgtatacg cttatcctcc   1680
ctacactcca tttgtgggac tattgttgtt attttggata agctgaggta tccatcttct   1740
actaactgca ctagtttatt ttttttgctg tttacagttg aaacaattgt ctgaggattt   1800
ctcacctgct gaatcaactg caatggctga acgtgtgctg actcgtgttc acagccttcg   1860
tgaacgtctt gatgctactt tggctgctca tcgcaatgag atattactgt ttctttcaag   1920
gtatagccaa agatagtatt cttgttaact aaaaaagatt cagttggtgt tcaaaaaacg   1980
atacgtttat ctgcctaagt cttggtagtc agaattatcc ggtacctatg ctggtgtgag   2040
ttagctggct aggaaaccac tcttatgaaa acaagagatt tagttagagt tgtctgtaat   2100
tctgtagtat ggactatgta tgtgatgcta tttgaactgg ttttggttat tataggattg   2160
aaagccatgg aaaagggatc ttgaaaccgc atcagctatt ggctgagttt gatgcaattc   2220
gccaagatga caaaaagaaa ctgaatgatc atgcatttga agaactcctg aagtccactc   2280
aggtaatatg gttttggcta tatttgtcgc caacgccaag ctcatatttt tatattattt   2340
tgagcttgtg tctgaatacg acgatgatat gttatactag gaagcaattg ttctgccacc   2400
ttgggttgca cttgcgattc gtttgaggcc tggtgtgtgg gaatatgtcc gtgtgaatgt   2460
caatgcgcta gtcgttgagg agctgactgt ccctgagtat ttgcatttca aggaagaact   2520
tgtcgatgga acgtaagtgt tagtcttcaa tttgatgcta tgttagagaa taggctgtgg   2580
aatttattga tcaatgctgt gctttgtcct gatacagctc caatggaaat ttcgttctcg   2640
agttggattt tgagcccttc accgcatcct ttcctaaacc aaccctcacc aaatctatcg   2700
gaaatggagt tgaattcctc aataggcacc tctctgcgaa aatgttccat gacaaggaaa   2760
gcatgacccc gcttcttgaa tttcttcggg ttcacaatta taagggcaag gtgacttgct   2820
atttccattt atctataggt tcggtttgtg cttatcatgc gcccaatgac atatgaatat   2880
gcgctaaagg atagatatat gatttccttt gcagacaatg atgctgaacg acagaataca   2940
gaatttaacc acactgcaaa atgtcctaag gaaggcagag gaatacctca ttatgcttcc   3000
ccctgaaact ccattttccg aattcgaaca caagttccaa gaaattggat tggagaaggg   3060
atggggcgac actgcagagc gcgtgctgga gatgatatgc atgcttcttg atctcctcga   3120
ggctcccgat tcctgtactc ttgagaagtt cttggggaga attcctatgg tgttcaatgt   3180
```

```
ggttatcctt tccccccacg gatatttcgc ccaggaaaat gtcttgggtt atcccgacac   3240
tggtggccag gtgcattact ttaatcttta tccgtgagtc tatgtttgtt cgaatcctct   3300
agaaatgtca ctgtacctat gtaggatact ccaaatataa tgcattttgg ggggatctgt   3360
tatgggtgcg atggcatttt tggaggtcgg agcaacaaac aattgctatg tattcttcta   3420
aagcttgctt tcataaatgc taaggtcctt caccctttaat gtgcaggttg tctatatatt  3480
agatcaagtt ccagccttgg agcgtgaaat gcttaagcgc ctaaaggagc aaggacttga   3540
tatcacaccg cgtattctta ttgttagtat ttcctgtact tgtaattact gcggattaca   3600
caaaatttcc tttttatctt cttaacaact tatcttgatg gtattcccag gttactcgtc   3660
tgctacctga tgcagttgga acgacttgtg gtcagcggct tgagaaggtg tatggagccg   3720
agcactcaca tattctgagg gtcccctta ggactgagaa gggcattgtt cgtaaatgga    3780
tctctcgctt tgaagtgtgg ccatatatgg agactttcac tgaggtgaca ctaaaacttc   3840
cttatatttg tctatcttct aattggtatt aggaataatt tgttaattgt taactctttg   3900
tcttttcgta catcaggatg tcgcaaaaga acttgctgca gaattgcagg ccaagccaga   3960
tttgataata ggcaactata gcgagggaaa tcttgtggct tcattgctcg ctcataagtt   4020
aggcgtaaca caggtctgtg ttgtttttca ctctcttaaa gatctgattg catttccatt   4080
agtctggaac tagaagtact aaaaagttct tttcttcact gtgttatttg ccgtcggcag   4140
tgcaccatag ctcatgcatt ggagaaaaca aagtatcctg attctgacat ctactggaaa   4200
aaattcgatg aaaaatacca tttctcgtcc cagtttaccg ctgatcttat tgcaatgaat   4260
cacaccgatt ttatcatcac cagcactttc caggagatag caggaaggta taacatcaat   4320
ttgctacttc gactgcaaca gcattgtgtt cccatttctt tcccttatgc ttaacctaat   4380
accgtcatga attttccagc aaggacactg tcggacagta cgagagtcat caggcattca   4440
caatgcccgg attgtacaga gttgttcacg gcattgatgt gttcgacccc aaattcaaca   4500
ttgtctcacc tggagctgac ataaacctct atttcccata ttccgagaag gaaaagagac   4560
tgacagcact tcaccctgaa atcgaggagc tgctgtacag tgacattgag aacgaggaac   4620
atctgtaagt ttctacctta ctcgtacagt cagtggcgga gccagaattt tcactaaaat   4680
aaggtcaaaa tataaagaca taaatccaca aagaagccaa gggtgtcaat atatagtata   4740
aatacattaa aaaaattacc tatctacaca gtgtaatttt ccgacaaagg ggtgtcggtt   4800
gacactcctt gaatacatgt ggctctgcca ctgggtacag ttacaaagtt ctgttaccta   4860
tgtagatgag cttgtgctga acatgttgtg attttggcag gtgtgtgcta aaggacagga   4920
ataagccaat cttattcaca atggcgagat tggatcgtgt gaagaattta accggacttg   4980
ttgagtggta tgccaagaac gcacggctaa gggagttggt taaccttgtt gtggttggtg   5040
gagatcgaag gaaagaatcc aaagatttgg aagagcaaac agaaatgaaa aagatgtatg   5100
agctaataaa gactcacaat ttaaatggcc aattcagatg gatttcttca cagatgaacc   5160
gagtgaggaa cggtgaactc taccgataca ttgctgacac tagaggagct ttcgtgcagc   5220
ctgcattcta cgaggctttc ggtttgactg ttgttgaggc catgacctgt ggtttgccta   5280
catttgcaac taatcatggc ggtccagctg agatcatcgt taacggaaaa tctggcttcc   5340
acatcgatcc atatcacggt gagcaagctg ctgatctgct agctgatttc tttgagaaat   5400
gtaagacaga accttctcat tgggaaacca tttcaacggg tggcctgaag cgcatccaag   5460
agaagtaagc aactctttct tgactctagt cattgaaatt aactttcttg actctagtca   5520
```

```
ttgaaattaa ctcgggattt gaggcgtagt tgattgatat tttatcgcgt ctctactact   5580

gatatataca ggtacacgtg gcaaatctac tcggagaggc tattgacatt ggctgctgtt   5640

tacgggttct ggaaacatgt ttctaagctt gatcgtctag aaatccgtcg atatcttgaa   5700

atgttttatg ctctcaaata ccgcaagatg gtgagttcct cttcttcctt gcccttctcc   5760

tagtgtttaa gatacaatat aattgattgc attatcttag agaatcatta atgttaaatt   5820

ttcttaattc ttgaatctgt taatgaagtt tttctcttgg tttttgttta ggctgaagct   5880

gttccattgg ctgctgagtg a                                             5901
```

<210> SEQ ID NO 8
<211> LENGTH: 825
<212> TYPE: PRT
<213> ORGANISM: Nicotiana tabacum

<400> SEQUENCE: 8

```
Met Leu Phe Met Gly Leu Lys Gln Leu Ser Glu Asp Phe Ser Pro Ala
1               5                   10                  15

Glu Ser Thr Ala Met Ala Glu Arg Val Leu Thr Arg Val His Ser Leu
            20                  25                  30

Arg Glu Arg Leu Asp Ala Thr Leu Ala Ala His Arg Asn Glu Ile Leu
        35                  40                  45

Leu Phe Leu Ser Arg Ile Glu Ser His Gly Lys Gly Ile Leu Lys Pro
    50                  55                  60

His Gln Leu Leu Ala Glu Phe Asp Ala Ile Arg Gln Asp Asp Lys Lys
65                  70                  75                  80

Lys Leu Asn Asp His Ala Phe Glu Glu Leu Leu Lys Ser Thr Gln Glu
                85                  90                  95

Ala Ile Val Leu Pro Pro Trp Val Ala Leu Ala Ile Arg Leu Arg Pro
            100                 105                 110

Gly Val Trp Glu Tyr Val Arg Val Asn Val Asn Ala Leu Val Val Glu
        115                 120                 125

Glu Leu Thr Val Pro Glu Tyr Leu His Phe Lys Glu Glu Leu Val Asp
    130                 135                 140

Gly Thr Ser Asn Gly Asn Phe Val Leu Glu Leu Asp Phe Glu Pro Phe
145                 150                 155                 160

Thr Ala Ser Phe Pro Lys Pro Thr Leu Thr Lys Ser Ile Gly Asn Gly
                165                 170                 175

Val Glu Phe Leu Asn Arg His Leu Ser Ala Lys Met Phe His Asp Lys
            180                 185                 190

Glu Ser Met Thr Pro Leu Leu Glu Phe Leu Arg Val His Asn Tyr Lys
        195                 200                 205

Gly Lys Thr Met Met Leu Asn Asp Arg Ile Gln Asn Leu Thr Thr Leu
    210                 215                 220

Gln Asn Val Leu Arg Lys Ala Glu Glu Tyr Leu Ile Met Leu Pro Pro
225                 230                 235                 240

Glu Thr Pro Phe Ser Glu Phe Glu His Lys Phe Gln Glu Ile Gly Leu
                245                 250                 255

Glu Lys Gly Trp Gly Asp Thr Ala Glu Arg Val Leu Glu Met Ile Cys
            260                 265                 270

Met Leu Leu Asp Leu Leu Glu Ala Pro Asp Ser Cys Thr Leu Glu Lys
        275                 280                 285

Phe Leu Gly Arg Ile Pro Met Val Phe Asn Val Val Ile Leu Ser Pro
    290                 295                 300
```

```
His Gly Tyr Phe Ala Gln Glu Asn Val Leu Gly Tyr Pro Asp Thr Gly
305                 310                 315                 320

Gly Gln Val Val Tyr Ile Leu Asp Gln Val Pro Ala Leu Glu Arg Glu
                325                 330                 335

Met Leu Lys Arg Leu Lys Glu Gln Gly Leu Asp Ile Thr Pro Arg Ile
            340                 345                 350

Leu Ile Val Thr Arg Leu Leu Pro Asp Ala Val Gly Thr Thr Cys Gly
        355                 360                 365

Gln Arg Leu Glu Lys Val Tyr Gly Ala Glu His Ser His Ile Leu Arg
    370                 375                 380

Val Pro Phe Arg Thr Glu Lys Gly Ile Val Arg Lys Trp Ile Ser Arg
385                 390                 395                 400

Phe Glu Val Trp Pro Tyr Met Glu Thr Phe Thr Glu Asp Val Ala Lys
                405                 410                 415

Glu Leu Ala Ala Glu Leu Gln Ala Lys Pro Asp Leu Ile Ile Gly Asn
            420                 425                 430

Tyr Ser Glu Gly Asn Leu Val Ala Ser Leu Leu Ala His Lys Leu Gly
        435                 440                 445

Val Thr Gln Cys Thr Ile Ala His Ala Leu Glu Lys Thr Lys Tyr Pro
    450                 455                 460

Asp Ser Asp Ile Tyr Trp Lys Lys Phe Asp Glu Lys Tyr His Phe Ser
465                 470                 475                 480

Ser Gln Phe Thr Ala Asp Leu Ile Ala Met Asn His Thr Asp Phe Ile
                485                 490                 495

Ile Thr Ser Thr Phe Gln Glu Ile Ala Gly Ser Lys Asp Thr Val Gly
            500                 505                 510

Gln Tyr Glu Ser His Gln Ala Phe Thr Met Pro Gly Leu Tyr Arg Val
        515                 520                 525

Val His Gly Ile Asp Val Phe Asp Pro Lys Phe Asn Ile Val Ser Pro
    530                 535                 540

Gly Ala Asp Ile Asn Leu Tyr Phe Pro Tyr Ser Glu Lys Glu Lys Arg
545                 550                 555                 560

Leu Thr Ala Leu His Pro Glu Ile Glu Glu Leu Leu Tyr Ser Asp Ile
                565                 570                 575

Glu Asn Glu Glu His Leu Cys Val Leu Lys Asp Arg Asn Lys Pro Ile
            580                 585                 590

Leu Phe Thr Met Ala Arg Leu Asp Arg Val Lys Asn Leu Thr Gly Leu
        595                 600                 605

Val Glu Trp Tyr Ala Lys Asn Ala Arg Leu Arg Glu Leu Val Asn Leu
    610                 615                 620

Val Val Val Gly Gly Asp Arg Arg Lys Glu Ser Lys Asp Leu Glu Glu
625                 630                 635                 640

Gln Thr Glu Met Lys Lys Met Tyr Glu Leu Ile Lys Thr His Asn Leu
                645                 650                 655

Asn Gly Gln Phe Arg Trp Ile Ser Ser Gln Met Asn Arg Val Arg Asn
            660                 665                 670

Gly Glu Leu Tyr Arg Tyr Ile Ala Asp Thr Arg Gly Ala Phe Val Gln
        675                 680                 685

Pro Ala Phe Tyr Glu Ala Phe Gly Leu Thr Val Val Glu Ala Met Thr
    690                 695                 700

Cys Gly Leu Pro Thr Phe Ala Thr Asn His Gly Gly Pro Ala Glu Ile
705                 710                 715                 720

Ile Val Asn Gly Lys Ser Gly Phe His Ile Asp Pro Tyr His Gly Glu
```

```
                725                 730                 735

Gln Ala Ala Asp Leu Leu Ala Asp Phe Phe Glu Lys Cys Lys Thr Glu
            740                 745                 750

Pro Ser His Trp Glu Thr Ile Ser Thr Gly Gly Leu Lys Arg Ile Gln
        755                 760                 765

Glu Lys Tyr Thr Trp Gln Ile Tyr Ser Glu Arg Leu Leu Thr Leu Ala
    770                 775                 780

Ala Val Tyr Gly Phe Trp Lys His Val Ser Lys Leu Asp Arg Leu Glu
785                 790                 795                 800

Ile Arg Arg Tyr Leu Glu Met Phe Tyr Ala Leu Lys Tyr Arg Lys Met
                805                 810                 815

Ala Glu Ala Val Pro Leu Ala Ala Glu
            820                 825


<210> SEQ ID NO 9
<211> LENGTH: 8323
<212> TYPE: DNA
<213> ORGANISM: Nicotiana tabacum

<400> SEQUENCE: 9

atggcgaatc caaagttcac aagagtacct agcatgaggg agagagttga ggatactctc     60

tctgctcacc gtaaccagct tgttgctctc ctctccaggt atattaataa actctatata    120

cttgttattt tctttatttt tttgtcttta ctgataaatt taactgtttt cttctttaaa    180

tcttgctttc gatgcatgat ttctgttgtg ttaaattgcg taaccatttt atctaaaagt    240

ttatgctgat aaacactttt aaattttaat atgtaaatta tattatgtct caacatcaac    300

atgtggatgg ccaaaaatat aaagcttaat tttcgttatt ttgaatgatt tttctctgcg    360

agtgttacgg tttgcgtaca cattacctaa acctcctccc tagtccccac ttgtgggaat    420

ttaatttttt ttttctttgt ttttttttgt tgttgttgtt gtctgagttc aattcctacc    480

atgttagctt ggcaaaaata agttggtaaa gcttgacccc aactagtttt agttgatcga    540

tttatttggt gatttatagt tcaataataa taattactat tagagaaagt tccagcagct    600

tttctgtttg tttttccagt tttagtgatt gatatatgtg tatatatatt ctttgtttct    660

tttaagatac gtggcgcagg ggaaggggat attgcaacct caccacttga tcgatgagtt    720

caacaacgct gtatgtgatg acactgcttg tgagaagctc aaagatggtc cctttagtga    780

agtcttgaaa gctactcagg tatattcact aatccatggg aatcaagatg atactgtata    840

tctttattat ggtgtctttc agaaatttga cgatgatgaa atgcaacttt tctctgtttg    900

tcaccttatc cagactgttt ttttattttt tatttttcat tttttaactt gaaatgctct    960

taatttcctt tgtttatcga taagaccgga tttacaatgt atgaacggag catcttaaga   1020

accttctgga atgaagatat aagatataaa acatggtgtc cgttttctcc tttgtggaat   1080

cagtgtacat atagactgtt attttggtcc cactttctgg atcttctgat cacaccttct   1140

catgcagagg cgagcttgat ggtttcaacc tttaaattct tactattgaa tccatttcac   1200

tttcgaaatt atgagttcga aatctaatat ttgttgaaat ttttgcaaat gttcacatat   1260

aagtttaagc tttgtgtcaa gaatactggg ctcaatggat tccaatagac caggctgtat   1320

ccgcctctgt ctccactctc cctgcatcca cttctttcgt gtgactaata atgcttaatg   1380

agctagaact cgttttaatg tttgaataag ttgcttatat cagagcagct tttgatgttt   1440

caatctttaa cgggttatgc agtaccagca ttctgcggct gaaaaacagg aatctgagat   1500

ttacttgtct ctggctgaat ttcttgttca ttttgctaac aagtactttg gagttaatgc   1560
```

```
ttgctctctg ttgtcaaaat aggaagccat tgtgctgcca ccatttgttg ccatagcagt   1620
tcgtccaagg ccaggtgttt gggagtatgt tcgtgttaat gtatatgatt tgagcgttga   1680
acaattgact gttcctgaat atcttcattt caaggaagaa cttgtggatg gagagtaagc   1740
tctttcttat ttcaatacga aacataaaaa tttacagaag ttgaataatt aacaaatttg   1800
ttgattttta atgtatgcca ggggtaataa tcactttgtg cttgagctgg attttgagcc   1860
atttaatgca tcagttcctc gtccatctcg atcgtcatcc attggcaatg gagtccaatt   1920
cctcaatcgt catctttcct caattatgtt tcgcagcaaa gactctctgg acccccttact   1980
tgatttcctt agaggacact gtcataaagg gaatgtaagt accaaaagca gttttccctt   2040
tgtaaatgtc tgcttgtccc tgattatcta ctaaatcttt caacacgcgc aaccattata   2100
agaaatgtac aatacttcta gttagaattt catcatcgac aaactatctg ctttactttt   2160
tatttttccc atttgatgga tgatagttta gtttatataa cagatgatat tttggttgaa   2220
gggtaccatg aactttttca caaccactta atggatacat agttgtaata gttgacattt   2280
tggaataata ttgtctcact tggaaatgtt taagaagtat tactacttct atttgtaaga   2340
tggattgttt atctatgcag gtcttgatgt tgaatgatcg tatacagcga atctccaggc   2400
tggagtctgc tctttctaaa gcagaggatt atctctccaa gctatcacca gatacatcct   2460
ataatgagtt cgaatacgcg tgagcttgta cacatttgtt ttgttttctt tcaagcatat   2520
gtaatttctc aagaaaaggg aaatctatag gagttgaaac attctttatg gaaccatgtg   2580
catgcagatt gcaagaaatg ggctttgaga gaggttgggg tgatactgcc agacgtgttt   2640
tggagacgat gcatcttctt tctgacattc ttcaggctcc ggatccatca accttggaga   2700
catttcttgg tagactacct atggtgttca atgtcgtcat attatcccct catggatatt   2760
ttggccaagc aaatgtcttg ggtttgcccg acactggtgg ccaggtaata acaaggagaa   2820
tgaggtcttg tattatgtac tccctccgtt ccaatctata tgaacctatt tgactgggta   2880
tggaaagaaa tgaagacttg taaaacttgt ggttctttag aaattccaaa cattacattt   2940
ggtttttttcc ctcttcctgg aaattatact actgaatcat ctctagatgt tccagtttaa   3000
cttgagacgt aagggtaaat aacggaccat tactctgtcc tttcttgcag taggcttggt   3060
acaatgaata tagttcgcat agttgccgga agctagagct gtgttagaaa actcaggaac   3120
attaatttgg cgatgctaat cactgctaat gttactgaag catccatggt tttccttgat   3180
gttattctcc ttttggttgc ttcacaggtt gtctatatac tggatcaagt gcgtgccttg   3240
gaggccgaaa tgcttcttag aataaagcaa caaggactta acttcaagcc tagaatcctt   3300
gtcgtgagta catatatatt atgcaagctc ttatttggtt tgtgggattg cagttgacat   3360
caatttgctt actctgatta ctaaaggtca cacggctgat acctgatgct aaaggaacca   3420
tgtgcaacca gaggttggag aggattagtg gaactgaata ctcgcatatt ttacgtgtcc   3480
cttttaggac agagaaggga atccttcata aatggatatc taggtttgat gtatggcctt   3540
acctggagaa gttcactgag gtaacctctt tgtcccttgg aaattgcctt ttgttgctga   3600
tgtttctgct agtgtgctta aatgacggat gttaactagt cacttgctag cgtttgcaat   3660
agcaacggga aaagaaagga tttttgctag tttgaagtct gcctccaaga aaaattatat   3720
taaaagttta tggctagtgg aaacatcagt cattcatgta ccttatttct atgcccaagt   3780
tgtttaagtt gaaagtaatt tggccaacta tgcaaattgg gagaacgtgt agccaactat   3840
tgtgtttgcc gacatgttga tatacttttt ggtcctgatt tatatttgtt ggtttgtcat   3900
```

```
actggatgaa gcaattctca tgtttttctg cttatatata ttggaagaag agatacttgt   3960
cgtttcatca tttttctcga cctctctatt accaacactt tgccaattta atgtttggaa   4020
atgtcttctt gaccaggatg tggcaagtga aatgaccgct gagctccagg gaaagccaga   4080
tctgattatt ggcaactaca gtgatggaaa tttagttgcc tcccttttgg catataaaat   4140
gggtgtcaca caggtaggaa atacatgatt ctttatcttg ctagcactaa gtcttgaggt   4200
tatgtatctg caatagaaat tttacgcttt gccttcattt ctttttaatt atttttccag   4260
tgtaccattg ctcatgcctt ggaaaaaaca aagtatcctg attctgacat ctactggaaa   4320
aagtttgagg agaaatatca tttttcatgt cagtttactg ctgatctact ggcaatgaat   4380
aattcagatt tcattatcac cagtacttat caagagattg caggaacgta agtcatttta   4440
atctggtcgt ttaaatctga tatttcttcc ctagtagtct attcaatccg aatttcagtt   4500
cagtatatga tgtcatcggt tgaggaactg tgattggtaa ccttatcaaa tccgtagctg   4560
ctctataatt ttatttcgta attggagaaa caatttttta ttattgagct tgtagtctga   4620
gctagaattt ggttctttat ctatcaagta gcataatact acaactattt tttatgtgtg   4680
gcaatttgca atttcaattt tctatttcta taagttgcag cttttcttcc tgttctgatc   4740
atatttacat ggctgaaact caatagaaaa ctaggctagt tgatcaaaag tagttggatg   4800
ctttaaaatt agtagacgtt ttgctaaatg agtgaccaat gttattaaaa aaacgttcat   4860
gttttcaacc cttttggcat acatttgacc actgcccaag attttggata agtacatgca   4920
gtgcttataa ttataaagca ttttatccca ccttgttttt cattatgaaa attaagtaat   4980
ttacgagtat ttgtataagt tacttcataa attagaagta aatctggatt gtgtaaagtt   5040
attcgccccg tatatactga aagctacttg aacaagcaaa aaaacagaca aacgtaacat   5100
tctccatgga ttaatgagac ttgtatatat atatatatat atatgtaaag agagagagag   5160
agagatttgg cttgtaacca catgtatatt atgccatatg gatgtgacat tgatgtgact   5220
agacctaaat gttttgtttc aatgtccacg ggagttttac gtagagttaa gaggagaaga   5280
gagtgaggaa tactaatgtt tgatggtacc ccttggcttc ttgacctgga tactcagtgt   5340
tcttattcat gcctatactt tggtccttga tttcattctc ccttttctag cttgagctgc   5400
atcaaagaaa ttccactgta aaaaaaataa tgctcaccat attggtgcaa catggcaaac   5460
atgtatccta tttgatgatc aatcaacttt atttttctcc tgttaattga cctcagtgtg   5520
taactctcta tgtatgatag cattgtaact tgtgtcatga ttcataaata gggtactaga   5580
attggatggt tgacatagta aatggtcaat tgatgatcca caaaatatgc acctactgat   5640
taaaatgtga tagggcaggt ttatttttgt ttgtggttaa cacagtactt aaccctatat   5700
ttaatacaat ttggcttatc tacaatcttt tcttcagtgt ttatgcgaat tccttattgc   5760
acaacaatat tgtctttctg agttctattc tgttgttgct tacactttta ttattccagt   5820
aacatagatg tgaagacatt agattggttg cttgcaaatt gatagccact tgtttcagga   5880
agaatactgt tggtcagtac gagagccata ctgcattcac cctcccggga ctatatcgcg   5940
tcgttcatgg cattgatgtt ttcgatccca aattcaatat agtgtctcct ggagctgaca   6000
tgacaattta tttcccatat tctgacaagg aaaaaagact aacgtctttg catggctcga   6060
ttgaaaagtt gttatttgat cctgcgcaga atgaagagca tatgtaagtg gcatccgttt   6120
gtacttaatt tttttggaat agatgacata ttatttgcat gaatatgaaa aggagggtct   6180
gatatgattt tctatagata aactaccaat gatattattt aaaaactcct ggatactgta   6240
ttaggagaag aagagaacca ggggtagatg gcattagaat cccttaaatc ttgaagagtc   6300
```

```
gtcactaacg ctcccaacac ttctgcctca gaccctcaac taaatactat tattgttgat   6360
ttctttggag aagctataag aatctctctc tccttatggt gaaaatttta cttggcttta   6420
tacttaactt ccaaggctcc ctcttataaa atgcaaaaac tgtctgtatt cactctcttg   6480
gttaacaatt gatccaatca aatgcatatg gaacatcttt ctttacgttt cttctaaagt   6540
tcgtttgagg ataaggagta gaatctgaga agatagacta gtaggtaacc ttagggacgg   6600
atgtggaaat taacatatgg gctcagcttt tctgccgagt gcagaccatg tatatgcgtt   6660
aaaaaattca ctaaacaagt aaatgtttga ttttgaaccc agtaaatcaa atgagttgtg   6720
gtagaatctc gaactcgaac cgataaagtt caaatccagg atccgctttt aggtaaactc   6780
taccttggga agtgttatat atatgtccct gattatttct ttttccgttt cctttctatt   6840
ttaattttta aagttatttt tagatggttt tattttttga taagtggtaa gttgttaata   6900
ttccaaatta aatgccattg tcataactat atacatttat aaagaatgat tgatcctagt   6960
ttctcattcc taagatccaa ataaggcaat aaacaatgtc ttagtaattg gacctgcttc   7020
tggtgatcaa cgcttgatcg cgtagttagt tatagatgac tgtaaaaact ttaaccattt   7080
taatggtttt gtcaaagaac aaatatcgga catattatag agaatggact attgtacttt   7140
gcttctgatt ggtcatttta ttgtgatccg taaattggct gtgactgatg tcatatcttt   7200
gcttacagag gtaatctgaa tgataaatca aaacccataa ttttttcaat ggcaaggcta   7260
gaccatgtta agaacattac gggactagtt gagtgctatg ctaaaaatgc cacattgagg   7320
gaattggcga accttgttgt agtagctgga tacaacgatg taaagaaatc cagtgataga   7380
gaagaaataa cagaaattga gaagatgcat gctcttatta aggagcataa attggatggg   7440
caattcagat gggtatcagc ccaaacaaac cgggcacgta atggtgagct ctatcgctat   7500
atagctgacc agagaggtat atttgttcag gtatgctatt tgtattgtat tagtccaatt   7560
tcattttttg caccaaaaga aaggttgtta ttgtgacgta tatgtttgtt ttagcctgca   7620
ttttatgaag catttggact aacggtggtt gaagctatga cttgtggtct tccaacattt   7680
gcaacttgcc atggtggtcc taatgagatc attgaacccg gtgtatctgg gttccatatt   7740
gatccttatc atcccgataa agctgctgaa ctcatgtcag aattctttca acgctgcaaa   7800
caagatccta ctcactggga aaaaatatct gcatctggtc tccgaaggat tcttgagagg   7860
tctgtagttg tgtacatgta tagaagatta aagaatgcta ccttgatatt tatttgaatc   7920
aaaaataaca ggaacatctc ttttttgaac atcactcaag ttcttatatt aaataatttt   7980
taggtatacg tggaagattt actccgagag gctgatgact ttatctggcg tatatggttt   8040
ctggaagctt gtttcaaaac ttgagaggcg tgaaactaga cgataccttg agatgttcta   8100
cattctcaaa ttccgcgagt tggtgagtgc cttttagctc cttttcagtt ccaataaact   8160
atatatgtgg tttaagtaag tattaagcat aaacatgtcc gtgcttgggg ctgtcgaaaa   8220
tgctatggac atatcctgag ctaaggattt ttcaagaaaa ttgatgttag ctttactcta   8280
tttacaggca aaatctgtac ctctagcaat tgatgacaag tga                     8323
```

<210> SEQ ID NO 10
<211> LENGTH: 810
<212> TYPE: PRT
<213> ORGANISM: Nicotiana tabacum

<400> SEQUENCE: 10

```
Met Ala Asn Pro Lys Phe Thr Arg Val Pro Ser Met Arg Glu Arg Val
1               5                   10                  15
```

```
Glu Asp Thr Leu Ser Ala His Arg Asn Gln Leu Val Ala Leu Leu Ser
            20                  25                  30

Arg Tyr Val Ala Gln Gly Lys Gly Ile Leu Gln Pro His His Leu Ile
        35                  40                  45

Asp Glu Phe Asn Asn Ala Val Cys Asp Asp Thr Ala Cys Glu Lys Leu
    50                  55                  60

Lys Asp Gly Pro Phe Ser Glu Val Leu Lys Ala Thr Gln Glu Ala Ile
65                  70                  75                  80

Val Leu Pro Pro Phe Val Ala Ile Ala Val Arg Pro Arg Pro Gly Val
                85                  90                  95

Trp Glu Tyr Val Arg Val Asn Val Tyr Asp Leu Ser Val Glu Gln Leu
            100                 105                 110

Thr Val Pro Glu Tyr Leu His Phe Lys Glu Glu Leu Val Asp Gly Glu
        115                 120                 125

Gly Asn Asn His Phe Val Leu Glu Leu Asp Phe Glu Pro Phe Asn Ala
    130                 135                 140

Ser Val Pro Arg Pro Ser Arg Ser Ser Ser Ile Gly Asn Gly Val Gln
145                 150                 155                 160

Phe Leu Asn Arg His Leu Ser Ser Ile Met Phe Arg Ser Lys Asp Ser
                165                 170                 175

Leu Asp Pro Leu Leu Asp Phe Leu Arg Gly His Cys His Lys Gly Asn
            180                 185                 190

Val Leu Met Leu Asn Asp Arg Ile Gln Arg Ile Ser Arg Leu Glu Ser
        195                 200                 205

Ala Leu Ser Lys Ala Glu Asp Tyr Leu Ser Lys Leu Ser Pro Asp Thr
    210                 215                 220

Ser Tyr Asn Glu Phe Glu Tyr Ala Leu Gln Glu Met Gly Phe Glu Arg
225                 230                 235                 240

Gly Trp Gly Asp Thr Ala Arg Arg Val Leu Glu Thr Met His Leu Leu
                245                 250                 255

Ser Asp Ile Leu Gln Ala Pro Asp Pro Ser Thr Leu Glu Thr Phe Leu
            260                 265                 270

Gly Arg Leu Pro Met Val Phe Asn Val Val Ile Leu Ser Pro His Gly
        275                 280                 285

Tyr Phe Gly Gln Ala Asn Val Leu Gly Leu Pro Asp Thr Gly Gly Gln
    290                 295                 300

Val Val Tyr Ile Leu Asp Gln Val Arg Ala Leu Glu Ala Glu Met Leu
305                 310                 315                 320

Leu Arg Ile Lys Gln Gln Gly Leu Asn Phe Lys Pro Arg Ile Leu Val
                325                 330                 335

Val Thr Arg Leu Ile Pro Asp Ala Lys Gly Thr Met Cys Asn Gln Arg
            340                 345                 350

Leu Glu Arg Ile Ser Gly Thr Glu Tyr Ser His Ile Leu Arg Val Pro
        355                 360                 365

Phe Arg Thr Glu Lys Gly Ile Leu His Lys Trp Ile Ser Arg Phe Asp
    370                 375                 380

Val Trp Pro Tyr Leu Glu Lys Phe Thr Glu Asp Val Ala Ser Glu Met
385                 390                 395                 400

Thr Ala Glu Leu Gln Gly Lys Pro Asp Leu Ile Ile Gly Asn Tyr Ser
                405                 410                 415

Asp Gly Asn Leu Val Ala Ser Leu Leu Ala Tyr Lys Met Gly Val Thr
            420                 425                 430
```

```
Gln Cys Thr Ile Ala His Ala Leu Glu Lys Thr Lys Tyr Pro Asp Ser
        435                 440                 445

Asp Ile Tyr Trp Lys Lys Phe Glu Glu Lys Tyr His Phe Ser Cys Gln
    450                 455                 460

Phe Thr Ala Asp Leu Leu Ala Met Asn Asn Ser Asp Phe Ile Ile Thr
465                 470                 475                 480

Ser Thr Tyr Gln Glu Ile Ala Gly Thr Lys Asn Thr Val Gly Gln Tyr
                485                 490                 495

Glu Ser His Thr Ala Phe Thr Leu Pro Gly Leu Tyr Arg Val Val His
            500                 505                 510

Gly Ile Asp Val Phe Asp Pro Lys Phe Asn Ile Val Ser Pro Gly Ala
        515                 520                 525

Asp Met Thr Ile Tyr Phe Pro Tyr Ser Asp Lys Glu Lys Arg Leu Thr
    530                 535                 540

Ser Leu His Gly Ser Ile Glu Lys Leu Leu Phe Asp Pro Ala Gln Asn
545                 550                 555                 560

Glu Glu His Ile Gly Asn Leu Asn Asp Lys Ser Lys Pro Ile Ile Phe
                565                 570                 575

Ser Met Ala Arg Leu Asp His Val Lys Asn Ile Thr Gly Leu Val Glu
            580                 585                 590

Cys Tyr Ala Lys Asn Ala Thr Leu Arg Glu Leu Ala Asn Leu Val Val
        595                 600                 605

Val Ala Gly Tyr Asn Asp Val Lys Lys Ser Ser Asp Arg Glu Glu Ile
    610                 615                 620

Thr Glu Ile Glu Lys Met His Ala Leu Ile Lys Glu His Lys Leu Asp
625                 630                 635                 640

Gly Gln Phe Arg Trp Val Ser Ala Gln Thr Asn Arg Ala Arg Asn Gly
                645                 650                 655

Glu Leu Tyr Arg Tyr Ile Ala Asp Gln Arg Gly Ile Phe Val Gln Pro
            660                 665                 670

Ala Phe Tyr Glu Ala Phe Gly Leu Thr Val Val Glu Ala Met Thr Cys
        675                 680                 685

Gly Leu Pro Thr Phe Ala Thr Cys His Gly Gly Pro Asn Glu Ile Ile
    690                 695                 700

Glu Pro Gly Val Ser Gly Phe His Ile Asp Pro Tyr His Pro Asp Lys
705                 710                 715                 720

Ala Ala Glu Leu Met Ser Glu Phe Phe Gln Arg Cys Lys Gln Asp Pro
                725                 730                 735

Thr His Trp Glu Lys Ile Ser Ala Ser Gly Leu Arg Arg Ile Leu Glu
            740                 745                 750

Arg Tyr Thr Trp Lys Ile Tyr Ser Glu Arg Leu Met Thr Leu Ser Gly
        755                 760                 765

Val Tyr Gly Phe Trp Lys Leu Val Ser Lys Leu Glu Arg Arg Glu Thr
    770                 775                 780

Arg Arg Tyr Leu Glu Met Phe Tyr Ile Leu Lys Phe Arg Glu Leu Ala
785                 790                 795                 800

Lys Ser Val Pro Leu Ala Ile Asp Asp Lys
                805                 810
```

<210> SEQ ID NO 11
<211> LENGTH: 3604
<212> TYPE: DNA
<213> ORGANISM: Nicotiana tabacum

<400> SEQUENCE: 11

```
atgtttacat ggctgaaact caatataaaa aacaagggta ggtgatcaaa aatcgttgga     60
tgcttaaaat cagtagacgt tttgctaaat gagcgaccaa tgttattgaa aacgttcatg    120
ttttcaaccc ttttggcata catttgagca ttgcccaaga ttttggataa gtagatgcag    180
tgcttataat tttaaagcat tgtatcctgc cttgtttttc attgtcaaaa ttaattaact    240
tacaagtatt tctataagtt gcttcataaa ttagaagtaa atctggattg tgtaatgtta    300
ttcgcctcgt aaatactgaa agctgcttga acaagtgaaa aaacacagac aaacgtaaca    360
ttctccatgg attgatgaga cttgtaaaat acatatatag aaatttggct tgtaaccaca    420
tgtatattat gccatatgga tgtgacattg atgtgactag acctaaatgt tttgtttcca    480
tgtccactgg agttttacgt atagttaaga ggagaaaaga ctgaggaata ctaatgtatg    540
atggtacccc tttgcttctt gacctggata cccagtgttc ctattcatgc ctatactttg    600
gtccttgatt tcactctccc ttttctaact tgagctgcat caaagaaatt tccactgtaa    660
aaaaataaat aatgctcacc atatctctgc aacattgcaa acatgtatcc catatgattg    720
atattggtgc gacatggcaa acatgtatcc tatttgatga tcaatcaaat ttatttttcc    780
cctgtcaaaa tgacctcagt gtgtaattcc ctatgtattt gatagcattg taactcgtgt    840
catgattcat gaataggta ctagaattgc atggttgaca aatattaact ggtcgattga     900
tgatccacaa aacatgcact tactgactaa aatgtgatgg gacagattta tttttgtttg    960
tgattaacac agtacttaac cctatactta atacaattg gcctagctac aatcttttct    1020
tcagtgcaaa ttccttgtta cacgaccaat attgtctttc tgagttctat tctgttgtta   1080
cttacacttt tattattcga ataagacatt agattgcttg catgcaaatt gatagccact   1140
tgtttcagga agaatactgt tggtcagtac gagagccata ctgcattcac cctcccagga   1200
ctatatcgcg tcgttcatgg cattgatgtt ttcgatccca aattcaatat agtgtctcct   1260
ggagctgaca tgacaattta cttcccatat tctgacaagg aaaaaagact aacgtctttg   1320
catggctcga ttgagaagtt gttatttgat cctgcgcaga atgaagagca tatgtaagtg   1380
acatccattt gtacttattt taatttggaa tagatgacat acttatttgc atgaatataa   1440
actgacaacc cagagatttc ctacattaga aaaggagggt ctgatatgat tttctacaaa   1500
taaattccca gtgatattgt tcaaaaagtc ctggatactt tattatgaga gaaccaggga   1560
tagatggcac tagaatccct taatcttgag aagtcgccac ttatcgctcc caacactttc   1620
tgagaccctc aagtaactac tattattgtt tgatatcttg gagaagctat aagaatcttt   1680
ttctccttat tgtaattttt tttacgtgac tttaaactta acttccaagc tccttctgat   1740
aaaatgcaaa aactgtctgt attcactgtc ttggtttatt aacaattgat ccaatcaaat   1800
gcatatggaa catctttctt tttgtttctt caaaagttcg tttgaggata aggagtagaa   1860
tctgagaaga tagactagta ggtaacctta ggggcggatg tagaaatcaa cgtatgggtt   1920
cagctttgtt gcagaccctg tatatgcatt aaaaaaatca ctaaataagt aaataattga   1980
ttttgaaccc agtaaatcaa aatgagttgt agtagaatcc tgaactcgaa ccgataaagt   2040
tggatccact accgggtaaa ctctaccttg agaagtgttt atatatgtcc ctaattattt   2100
cttttctgtt tcctttctat tttaattttt taagttcctt tttagatggt tttatttttt   2160
gacaagtggt aagttgttag tattccaaat taaatgccat tgccataact atatacattt   2220
ataaagattg attgacccta gtttctcatt cctaagatcc aaataaggca ataaacaata   2280
tgtcttagta cttgaacctg cttctggtgg tcaacacttg atcgcgtagt tagttataga   2340
```

```
tgactgtaaa aaccttaatc attttaatgg ttttgtcaaa gaacaaatat cggacatatt   2400
atagcgaatg gactattgta cttttcttct gattggtcat tttattgtga tccgtaagtt   2460
ggctgagact gatgtcatat ctttgcttac agaggtaatc tgaatgataa atcaaaaccc   2520
ataatttttt caatggcaag gctagaccat gttaagaaca ttacgggact agttgagtgc   2580
tatgctaaaa atgccacatt gagggaattg gctaaccttg ttgttgtagc tggatacaac   2640
gatgtaaaga aatccagtga tagagaagaa atagcagaaa ttgagaagat gcatgctctt   2700
attaaggagc ataaattgga tgggcaattc agatggatag cagcccaaac aaaccgggca   2760
cgtaatggtg agctctatcg ctatatagct gacaagagag gtatatttgt tcaggtacgc   2820
tgtttgtatt gtatttgtcc acattccttt ttttgcaccg aaagaaaggt tgttattgtg   2880
acaaatatgt ttgttttagc ctgcatttta tgaagcattt ggactcacgg tggttgaagc   2940
tatgacttgt ggtcttccaa catttgcaac ttgccatggt ggtccgaacg agatcattga   3000
acacggtgta tctgggttcc atattgatcc ttatcatccc gataaagctg ctgaactcat   3060
ggcagaattc tttcaacgct gcaaacaaga tcctactcac tgggaaaaaa tatctgcatc   3120
tggtctccga aggattcttg agaggtttgt agttgtgtac atatatagaa gattaaagat   3180
tgttcccttg atattatttg aatgaaaaat aacagtaaca tctctttttg aacatcgctc   3240
aagttcttgt gttaaataat tgttaggtat acgtggaaaa tttactccga gaggctgatg   3300
actttgtctg gtgtatatgg tttctggaag cttgtttcaa aacttgagag gcgcgaaact   3360
agacgatacc ttgagatgtt ctacattctc aaattccgcg agttggtgag tgcctttttg   3420
ctcattttca gttacaatca actatatatg tggtttaaat acgtattaag cataaacatg   3480
tccgtgattg cggctgtcga aaatgctatg gacatatcct gagctaagga gttttcaaga   3540
gaattgattt ggcttactct gtttacaggc aaaatctgtt cctctggcaa ttgatgacaa   3600
gtga                                                                3604
```

<210> SEQ ID NO 12
<211> LENGTH: 335
<212> TYPE: PRT
<213> ORGANISM: Nicotiana tabacum

<400> SEQUENCE: 12

```
Met Phe Thr Trp Leu Lys Leu Asn Ile Lys Asn Lys Gly Arg Lys Asn
1               5                   10                  15

Thr Val Gly Gln Tyr Glu Ser His Thr Ala Phe Thr Leu Pro Gly Leu
            20                  25                  30

Tyr Arg Val Val His Gly Ile Asp Val Phe Asp Pro Lys Phe Asn Ile
        35                  40                  45

Val Ser Pro Gly Ala Asp Met Thr Ile Tyr Phe Pro Tyr Ser Asp Lys
    50                  55                  60

Glu Lys Arg Leu Thr Ser Leu His Gly Ser Ile Glu Lys Leu Leu Phe
65                  70                  75                  80

Asp Pro Ala Gln Asn Glu Glu His Ile Gly Asn Leu Asn Asp Lys Ser
                85                  90                  95

Lys Pro Ile Ile Phe Ser Met Ala Arg Leu Asp His Val Lys Asn Ile
            100                 105                 110

Thr Gly Leu Val Glu Cys Tyr Ala Lys Asn Ala Thr Leu Arg Glu Leu
        115                 120                 125

Ala Asn Leu Val Val Val Ala Gly Tyr Asn Asp Val Lys Lys Ser Ser
    130                 135                 140
```

```
Asp Arg Glu Glu Ile Ala Glu Ile Glu Lys Met His Ala Leu Ile Lys
145                 150                 155                 160

Glu His Lys Leu Asp Gly Gln Phe Arg Trp Ile Ala Ala Gln Thr Asn
                165                 170                 175

Arg Ala Arg Asn Gly Glu Leu Tyr Arg Tyr Ile Ala Asp Lys Arg Gly
            180                 185                 190

Ile Phe Val Gln Pro Ala Phe Tyr Glu Ala Phe Gly Leu Thr Val Val
        195                 200                 205

Glu Ala Met Thr Cys Gly Leu Pro Thr Phe Ala Thr Cys His Gly Gly
    210                 215                 220

Pro Asn Glu Ile Ile Glu His Gly Val Ser Gly Phe His Ile Asp Pro
225                 230                 235                 240

Tyr His Pro Asp Lys Ala Ala Glu Leu Met Ala Glu Phe Phe Gln Arg
                245                 250                 255

Cys Lys Gln Asp Pro Thr His Trp Glu Lys Ile Ser Ala Ser Gly Leu
            260                 265                 270

Arg Arg Ile Leu Glu Arg Tyr Thr Trp Lys Ile Tyr Ser Glu Arg Leu
        275                 280                 285

Met Thr Leu Ser Gly Val Tyr Gly Phe Trp Lys Leu Val Ser Lys Leu
    290                 295                 300

Glu Arg Arg Glu Thr Arg Arg Tyr Leu Glu Met Phe Tyr Ile Leu Lys
305                 310                 315                 320

Phe Arg Glu Leu Ala Lys Ser Val Pro Leu Ala Ile Asp Asp Lys
                325                 330                 335


<210> SEQ ID NO 13
<211> LENGTH: 4030
<212> TYPE: DNA
<213> ORGANISM: Nicotiana tabacum

<400> SEQUENCE: 13

atggcggaac gtgtgctgac tcgtgttcat agccttcgtg aacgtcttga tgctactttg      60

gctgctcatc gcaatgagat tttgctgttt ctttcaaggt atagtcttag cagattgttc     120

tttgatttag ttgttattgc cagttctaat gtatgggctt atatataaac aaagtgttga     180

agtatgcaac catataaact gacagcttaa aatgcttgag agaacacact tttatttatt     240

taattatgcc ttcagcacaa gaagtggaac ttgacgcaat ggaaccatag gtcacgggtt     300

caagtcttgg aacagcctgc aatctaaggc tgcgtgtagt agaccctagt ggtccggccc     360

ttccacatat ctcgcttagt gtaccgggcc cattgagtac gggttcggcc gaacccagtc     420

gctttggtcc aatccatata tttgtcttaa aaatatattg aatatataca aattgttaat     480

ttagtttaaa tatgtgtatc atgggttatt catgctggtt ttggctgttg caggattgaa     540

agccatggaa aagggatact gaaacctcac cagttgctgg ctgaatttga ttcaattcac     600

aaagaagaca aaaacaaact gaatgatcat gcttttgaag aagtcctgaa atccactcag     660

gtatttgtgg ttttagtgtt aggtgatgga tagcatttat tgttttacta agatcacata     720

tgtgtcagtt tgtggctagt atttaaaatc tggtgtattt tgtcatacta ggaagcaatt     780

gttttgtccc cttgggttgc gcttgccatt cgtctgaggc ctggtgtgtg ggaatacgtt     840

cgtgtgaatg tcaacgctct tgttgttgag gagcttaccg tgcctgagta tttgcaattc     900

aaggaagaac ttgttaatgg aacgtaagtt ttaggttcga atttgttgat ttgttagata     960

acatgttctg aactttttga ttaaagttgt gtttttgact gatgcagctc gcacgataac    1020

tttgttcttg agttggattt tgagcccttc actgcatcat ttccaaaacc aaccctcacc    1080
```

```
aaatcaattg gaaatggagt tgaattcctt aaccgacacc tctctgccaa aatgttccat   1140
gacaaggaaa gcatgacccc tcttctcgag tttcttcgag ttcaccacta caagggcaag   1200
gtaaacttgt ttttcctgtt tgtctatgaa tttagtttag ttgttttgct ccgcgaaaat   1260
ttcagtggaa actgatttat gcaaccactg agtgattaat atgttcaaac ttaccgactt   1320
ctggttttct gtgtagacaa tgatgctgaa tgacagaatt caggacttaa atactctcca   1380
aaatgtccta aggaaagctg aggaatacct cactaccctt tcccctgaaa cttcatactc   1440
ggcatttgag cacaagttcc aagaaattgg cttggagagg ggttggggtg acactgcgga   1500
gcgtgttcta gagatgatct gcatgctcct ggatctcctc gaggctcctg actcgtgcac   1560
gcttgagaag ttccttggta gaattccaat ggtttttaat gtggtcatac tttcacccca   1620
tggttatttc gcccaggaaa atgtcttggg ttaccccgac actggtggcc aggtgcactg   1680
cttatctgtg ttcggtctta ttatctcttt aaaccctact gccacaagtg ctgagatgaa   1740
cctcctttaa tttgcaggtt gtctatattt tggatcaagt tcctgctttg gagcgtgaga   1800
tgctcaagcg cataaaggag caaggacttg acatcaaacc gcgtattctt attgttcgta   1860
ttcccagtaa ttgtgtttaa acttatgatt atgcaggatt ttatctgttc taatacagca   1920
ctcttgctta aattctcagg ttactcggct gctgcctgat gcggttggta ccacttgtgg   1980
tcagaggctt gagaaagtgt ttggaacaga gcactcacac attcttaggg tcccctttag   2040
gaccgagaag ggcattgttc gcaaatggat ctctcgcttt gaagtctggc catacatgga   2100
gacattcact gaggtgaagc aagctttctc tattcatttt tcaatcttcc aattggtttt   2160
ggcagcaatt ttctgcttgc tttgacttcc gctaaaactt cggattttat tgcattagga   2220
tgtggcgaaa gaaattgctg cagaattgca ggctaagcca gatcttatca ttggcaatta   2280
tagtgagggc aaccttgctg cctccttgtt ggctcacaaa ttaggtgtaa cacaggtcgg   2340
caatgtttgt gacatgtaat ttcatctttg catttccttt cgtttgcaac taaaagattt   2400
aagagttctc tctctctttt ttttttccgt ctactttgcc ttatgcagtg cacgatagct   2460
catgctttgg agaaaacaaa atatcctgat tctgatatct acttgaagaa atttgatgaa   2520
aaataccatt tctcagccca gtttactgcc gatcttattg caatgaatca caccgatttc   2580
atcatcacca gcactttcca ggagatagcg ggaaggtatt tttacatcag tttcccactc   2640
tgattaaatt acaatgtatt tccctatatg attaaatact gtgtttgatc ctaaatcatt   2700
tctaaatttt ccagcaagga cactgttgga cagtacgaga gccacatggc gttcacaatg   2760
cctggactgt atagagttgt tcacggcatt gatgtgtttg accccaaatt taacattgtg   2820
tcaccaggag ctgatatgaa tctctatttc ccatactacg agaaggaaaa gagattgaca   2880
gcatatcacc ctgaaattga ggagctgctg tttagtgatg ttgagaatga cgaacacatg   2940
tatgttacta aactagcaat cctgctgcaa aattatggct aattatgtaa acaagtttgt   3000
actgaataga tttgttattc gatcaggtgt gtgctgaaga acaggaataa gcctatcata   3060
ttcactatgg ctagattgga tcgagtgaag aacttaactg gacttgtcga gctgtacgcc   3120
aagaacccac ggctaaggga gttggttaac cttgtcgtgg ttggaggaga ccgaaggaaa   3180
gaatccaaag acttggaaga acaggcagag atgaagaaga tgtacgaact tataaagact   3240
cacaatttga acggccaatt ccgatggatt tcttcccaga tgaaccgcgt gaggaatggc   3300
gaactctaca ggtacattgc cgatactagg ggagctttcg tgcagcctgc attttacgag   3360
gcttttggtt tgactgttgt tgaggccatg acctgtggtt tgcctacatt tgcaactaat   3420
```

```
cacggtggtc cagctgagat catcgttcac gggaaatctg gtttccacat tgatccatac   3480

cacggggatc aggcagctga acttctcgct gatttctttg agaaatgtaa gaaagaacct   3540

tcgcactggg aagccatttc cgagggcggc cttaagcgta tacaggagaa gtaagcaaac   3600

tgctactctt ttcatttttg caaaacctac tatgatcatt attaagctca tttttgcaaa   3660

acctacttgc tgttgttatt gtttgttgct tccttttcac tgttctttga gctgaaggtc   3720

tatcagaaac agtctctcta ccttcacaag gtaggggtaa gatctgcgtg cacgttaccc   3780

tcctcaaact ctacttaatt gtgagattac actaggtttg ttgttgttga ttctttgcta   3840

attaattaaa aggtacacat ggcaaatata ctcggatcgg ttgttgacac tggctgctgt   3900

atatggattc tggaagcatg tttccaagct tgatcgtctt gaaattcgcc gttatcttga   3960

aatgttctat gctctcaaat tccgcaagct ggtgagtttc attgctttct gcactcctgc   4020

aattgtatag                                                          4030
```

```
<210> SEQ ID NO 14
<211> LENGTH: 808
<212> TYPE: PRT
<213> ORGANISM: Nicotiana tabacum

<400> SEQUENCE: 14

Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Asp Ser Ile His Lys Glu Asp Lys Asn Lys Leu Asn Asp
    50                  55                  60

His Ala Phe Glu Glu Val Leu Lys Ser Thr Gln Glu Ala Ile Val Leu
65                  70                  75                  80

Ser Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Thr Val
            100                 105                 110

Pro Glu Tyr Leu Gln Phe Lys Glu Glu Leu Val Asn Gly Thr Ser His
        115                 120                 125

Asp Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Lys Gly Lys Thr Met
            180                 185                 190

Met Leu Asn Asp Arg Ile Gln Asp Leu Asn Thr Leu Gln Asn Val Leu
        195                 200                 205

Arg Lys Ala Glu Glu Tyr Leu Thr Thr Leu Ser Pro Glu Thr Ser Tyr
    210                 215                 220

Ser Ala Phe Glu His Lys Phe Gln Glu Ile Gly Leu Glu Arg Gly Trp
225                 230                 235                 240

Gly Asp Thr Ala Glu Arg Val Leu Glu Met Ile Cys Met Leu Leu Asp
                245                 250                 255

Leu Leu Glu Ala Pro Asp Ser Cys Thr Leu Glu Lys Phe Leu Gly Arg
```

```
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Phe Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Thr Glu Asp Val Ala Lys Glu Ile Ala Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Leu Lys Lys Phe Asp Glu Lys Tyr His Phe Ser Ala Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Asn Leu Tyr Phe Pro Tyr Tyr Glu Lys Glu Lys Arg Leu Thr Ala Tyr
    530                 535                 540

His Pro Glu Ile Glu Glu Leu Leu Phe Ser Asp Val Glu Asn Asp Glu
545                 550                 555                 560

His Met Cys Val Leu Lys Asn Arg Asn Lys Pro Ile Ile Phe Thr Met
                565                 570                 575

Ala Arg Leu Asp Arg Val Lys Asn Leu Thr Gly Leu Val Glu Leu Tyr
            580                 585                 590

Ala Lys Asn Pro Arg Leu Arg Glu Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685
```

```
Thr Phe Ala Thr Asn His Gly Gly Pro Ala Glu Ile Ile Val His Gly
    690                 695                 700

Lys Ser Gly Phe His Ile Asp Pro Tyr His Gly Asp Gln Ala Ala Glu
705                 710                 715                 720

Leu Leu Ala Asp Phe Phe Glu Lys Cys Lys Lys Glu Pro Ser His Trp
                725                 730                 735

Glu Ala Ile Ser Glu Gly Gly Leu Lys Arg Ile Gln Glu Lys Tyr Thr
            740                 745                 750

Trp Gln Ile Tyr Ser Asp Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Phe Arg Lys Leu Val Ser Phe Ile
785                 790                 795                 800

Ala Phe Cys Thr Pro Ala Ile Val
                805
```

```
<210> SEQ ID NO 15
<211> LENGTH: 4054
<212> TYPE: DNA
<213> ORGANISM: Nicotiana tabacum

<400> SEQUENCE: 15

atggccgaac gtgtgctaac tcgtgttcac agccttcgcg aacgtcttga tgctactttg      60

gctgctcatc gcaatgagat tttgctgttt ctttcaaggt atagtcttag cagattgttc     120

tttgatttag ttggtgttat ttgccagttc taatgtatgg actaatatat gaacaaagtg     180

cgaccatttc aactgacaac ttaaaatgtt tgagagaata cacgtttatt tacttaatta     240

tggcttgagc ataggaagtg tatcttggcg taactcgtaa agttgacctc atgtgacaag     300

gaggtcacgg tttcgagccg tggaaacagc ctcttgcaga aatgcaggta aggctgcgtg     360

caatagatcg cccttccacg gacccgcgca tagcgggaac ttagtgcacc ggttgggctg     420

tcctttttta tgtcttcagc acaaaaattt agtttaaaca tgtgtatcat ggattattca     480

tgctggtttt gccggttgca ggattgaaag ccacggaaaa gggatattga aacctcacca     540

gttgctggct gagtttgaat caattcacaa agaagacaaa aacaaactga atgatcatgc     600

ttttgaagaa gtcctgaaat ctactcaggt aatttgtggt tttagtgtta ggtgatggat     660

agcatttatt gtcttactaa gatcatatat gtgtcagttt gtggctagta tttgaaaagt     720

ctggtgtggt ttgtcatact aggaagcaat tgtcttgtcc ccttgggttg cgcttgccat     780

tcgtctgcgg cctggtgtgt gggaatatgt tcgtgtgaat gtcaatgcac ttattgtcga     840

ggagctgact gtgcctgaat atttgcaatt caaggaagaa cttgttaatg gaacgtaagt     900

tttaggttcg aaatgatgat ttgttaaata atatgttctg aactttttga ttaatgttgt     960

gttttcccct gatgcagctc gaacgataac tttgttcttg agctggattt tgagcccttc    1020

actgcatcat ttcccaaacc aaccctcacc aaatcaattg gaaatggagt tgaattcctc    1080

aaccgacacc tctctgccaa aatgttccat gacaaggaaa gcatgacccc tcttctcgag    1140

tttcttcgag ttcatcacta caagggcaag gtaaacttgt tttcctgtt tgtctatgaa     1200

tttagtttct gaaagttgct ttgcttcgtg aattttttag tggcaactga tttatgattt    1260

tctgtgcaga caatgatgct gaatgacaga gttcaggact taaacactct ccaaaatgtc    1320

ctaaggaagg ctgaggaata tctcactacc ctttcccctg aaacttcata ctcggtattt    1380
```

```
gagcacaagt tccaagaaat tggcctagag aggggctggg gtgacaatgc tgagcgtgtt   1440
ctagagatga tctgcatgct cctggatctc ctcgaggctc cagactcatg cactcttgag   1500
aagttccttg gtagaattcc tatggttttt aatgtggtca ttctttcacc tcacggatat   1560
ttcgcccagg aaaatgtctt gggttacccc gatactggtg gccaggtgca ctgcttattt   1620
gtaacacctt acgcttttcc ctctgaaact tatttgcggc aagttctaag gtcctccttc   1680
cttaatttgc aggttgtcta tattttggat caagttccgg ccttggagcg tgagatgctc   1740
aagcgcataa aggagcaagg acttgatatc aaaccgcgta ttcttattgt tcgtatctcc   1800
aataattgcg tttaaactta tgattgtgca ggatttgatc tgttcaaatc taatgactga   1860
ttttcttttt tttttttttt tccctcaggt tactcggctg ctgcctgatg cggttggtac   1920
cacttgtggt cagcggcttg agaaagtgtt tggaacagag cattcacata ttcttagggt   1980
ccccttttagg accgagaagg gcatcgttcg caaatggatc tctcgctttg aagtctggcc   2040
ttacatggag acattcactg aggtgaagca agctttctct attcattttt caatcttcca   2100
atctgttttg gcagcaattt ttcacttact aacactttgg ctttcgctaa aacttcggat   2160
tttattacat taggatgtgg caaaagaaat tgctgcagaa ctgcaggcaa agccagatct   2220
tataatcggc aactacagcg agggcaacct tgctgcctcc ttgttggctc acaagttagg   2280
tgtaactcag gtctgtaatg tttgtcacct gttatttcaa ctttgcattt cctttcattt   2340
gcaactagaa gttaagagtt ctctctcttt tatcttttcc gtctattttg ccttctgcag   2400
tgcaccatag ctcatgcgtt ggagaaaaca aaatatcctg attctgatat ctacttgaag   2460
aaatttgatg aaaaatacca tttctcagcc cagtttactg ccgatcttat tgcaatgaat   2520
cacaccgatt tcataatcac cagcactttc caggagatag cgggaaggta ttacatcaca   2580
atggatttcc gatatgatta aattagttaa tttaatccta cttcattgtg tttgatccta   2640
aaacttttct aaatttccca gcaaggacac tgttggacag tacgagagcc acatggcttt   2700
cacgatgcct ggattgtata gagttgttca cggcattgat gtgttcgatc ccaaattcaa   2760
cattgtgtca ccaggagctg atatgaatct ctatttcccc tacttcgaga aggaaaagcg   2820
attgacagca tatcaccctg aaattgagga gctgctgttt agcgatgttg agaatgacga   2880
acacatgtat gttactaaac tagcaatcct gctgcaaaat tgtggctaat tatgtaaaaa   2940
agtttttact gaatagattt gtgcttctat caggtgtgtg ctgaaggaca ggaataagcc   3000
aattatattc accatggcta gattggatcg agtgaagaac ttaactggac ttgtggagtt   3060
gtacgccaag aacccacggc taagggagtt ggttaacctt gtcgtggttg gtggagaccg   3120
aaggaaggaa tccaaagatt tggaagaaca ggcagagatg aagaagatgt atgaacttat   3180
aaagacgcac aatttaaacg gccaattccg atggatttct tcccagatga accgcgtgag   3240
gaatggcgaa ctctacaggt acattgccga tactagggga gcttttgtgc agcctgcatt   3300
ttacgaggct tttggtttga ctgttgttga ggccatgacc tgtggtttgc ctacgtttgc   3360
aactaatcac ggtggtccag ctgagatcat cgttcacggg aagtctggtt ttcacattga   3420
tccataccac ggcgagcagg cagctgaact tctagctgat ttctttgaga gatgtaagaa   3480
agaaccttca cactgggaag ccatttccga gggcggcctt aagcgtatac aggagaagta   3540
agcaagctgc tactcttttc atttttgcaa aacctaccat gatcattatt aagctcattt   3600
ttgcaaaacc tacttgttat tctttgttgc ttccttttcc ctgttttttg agccgaggtt   3660
ttatcgaaaa catgctttct accttcacaa ggtaggggta aggtctgcgt ttgttattat   3720
tgttgttgtt gattctctgc gaattaatta aaaggtacac atggcaaatc tactcggatc   3780
```

```
ggttgttgac actggctgct gtttatggat tctggaagca tgtttccaaa cttgatcgtc   3840

ttgaaattcg tcgttatctt gaaatgttct atgctctaaa attccgcaaa ctggtgagtt   3900

tcactgcttt ctgcactctt ccaattgtta gttgagtgca ctcatttaaa ctgtagctaa   3960

agctgttgta aatcttcagt taagcagctg ctaatgaagt ttttatcttt tgtttttggt   4020

tcaggctgaa gctgtcccgt tggctgttga gtaa                               4054
```

<210> SEQ ID NO 16
<211> LENGTH: 805
<212> TYPE: PRT
<213> ORGANISM: Nicotiana tabacum

<400> SEQUENCE: 16

```
Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Glu Ser Ile His Lys Glu Asp Lys Asn Lys Leu Asn Asp
    50                  55                  60

His Ala Phe Glu Glu Val Leu Lys Ser Thr Gln Glu Ala Ile Val Leu
65                  70                  75                  80

Ser Pro Trp Val Ala Leu Ala Ile Arg Leu Arg Pro Gly Val Trp Glu
                85                  90                  95

Tyr Val Arg Val Asn Val Asn Ala Leu Ile Val Glu Glu Leu Thr Val
            100                 105                 110

Pro Glu Tyr Leu Gln Phe Lys Glu Glu Leu Val Asn Gly Thr Ser Asn
        115                 120                 125

Asp Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Lys Gly Lys Thr Met
            180                 185                 190

Met Leu Asn Asp Arg Val Gln Asp Leu Asn Thr Leu Gln Asn Val Leu
        195                 200                 205

Arg Lys Ala Glu Glu Tyr Leu Thr Thr Leu Ser Pro Glu Thr Ser Tyr
    210                 215                 220

Ser Val Phe Glu His Lys Phe Gln Glu Ile Gly Leu Glu Arg Gly Trp
225                 230                 235                 240

Gly Asp Asn Ala Glu Arg Val Leu Glu Met Ile Cys Met Leu Leu Asp
                245                 250                 255

Leu Leu Glu Ala Pro Asp Ser Cys Thr Leu Glu Lys Phe Leu Gly Arg
            260                 265                 270

Ile Pro Met Val Phe Asn Val Val Ile Leu Ser Pro His Gly Tyr Phe
        275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320
```

```
Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Phe Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
    370                 375                 380

Pro Tyr Met Glu Thr Phe Thr Glu Asp Val Ala Lys Glu Ile Ala Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Leu Lys Lys Phe Asp Glu Lys Tyr His Phe Ser Ala Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Asn Leu Tyr Phe Pro Tyr Phe Glu Lys Glu Lys Arg Leu Thr Ala Tyr
    530                 535                 540

His Pro Glu Ile Glu Glu Leu Leu Phe Ser Asp Val Glu Asn Asp Glu
545                 550                 555                 560

His Met Cys Val Leu Lys Asp Arg Asn Lys Pro Ile Ile Phe Thr Met
                565                 570                 575

Ala Arg Leu Asp Arg Val Lys Asn Leu Thr Gly Leu Val Glu Leu Tyr
            580                 585                 590

Ala Lys Asn Pro Arg Leu Arg Glu Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val His Gly
    690                 695                 700

Lys Ser Gly Phe His Ile Asp Pro Tyr His Gly Glu Gln Ala Ala Glu
705                 710                 715                 720

Leu Leu Ala Asp Phe Phe Glu Arg Cys Lys Lys Glu Pro Ser His Trp
                725                 730                 735

Glu Ala Ile Ser Glu Gly Gly Leu Lys Arg Ile Gln Glu Lys Tyr Thr
```

```
        740                 745                 750

Trp Gln Ile Tyr Ser Asp Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Phe Arg Lys Leu Ala Glu Ala Val
785                 790                 795                 800

Pro Leu Ala Val Glu
                805


<210> SEQ ID NO 17
<211> LENGTH: 3752
<212> TYPE: DNA
<213> ORGANISM: Nicotiana tabacum

<400> SEQUENCE: 17

atggcctcaa cagttgctga tagcatgcct gatgctttga aacaaagccg gtatcatatg     60

aagagatgct tcgctaggtg aacacccttc ttttatgttt tttcccctct acgtgtttat    120

gtcaaatttc catgcataat gctaactact tttcttcttt ttgacttcaa aattggatgt    180

gaaaggttca ttgcaatggg aaggaggcta atgaagttga aacatttaac agaagaaata    240

gaagaaacta ttgaagacaa ggcagaaaga accaggattt tggagggttc acttggaaaa    300

attatgagtt ccacacaggt cagcaccatt taaccaactt agttgaacag gaaaaaaaga    360

aaaagcaaaa gagttattgc aaggcgtaac gattttcttt gaaattttca ggaggcagct    420

gttgttccac cttatgttgc ttttgcagta aggcacaatc ctggcttctg ggattatgtc    480

aaagttaacg ctgaaactct ctctgtggaa gctatttcag ccagggaata tctcaaattc    540

aaagagatga tctttgacga agactggtaa gtggaaaatt gtatcatttt aaagagaaac    600

aattttgtaa catacaagaa tagttttgat ggttgaatgt gcaagcaggg caaaggatga    660

taatgcactg gaagtagatt ttggtgcttt tgactactct aatcctcggt tagccctttc    720

ctcttctgtc ggaaatgggc tcaactttat ctcaaaagtt ctgtcttcaa agtttggtgg    780

aaagccagag gacgcccagc ctttgcttga ttacttacta gctcttaatc atcaaggaga    840

ggtatgaaaa tggactacct ttgtttctta aaggtattat ataatgatgc gcgttataaa    900

gttccttttt aaattgaaac tttgcagaat ctaatgatca atgagaatct gaatggtgtt    960

gctaagcttc aagcagcatt gatagtagct gaagtttttg tatcttcctt tcccaaagac   1020

acaccttata aagactttga gcataagtaa gcttctcata tgcttccatt gtcatatgca   1080

gtataccaat gacatgctac cgaaaagttg tttatgtttg tgacttgatt atgaaaactc   1140

taggctcaaa gaatggggct ttgataaagg gtggggtcac aatgcaggaa gagtaagaga   1200

gacaatgaga ctgctttccg agataatcca agcaccagat cccataaata tggagtcctt   1260

tttcagcaag cttcctacta cattcaacat tgttatcttc tccattcatg gttactttgg   1320

ccaagcagat gtccttggtc tgcccgatac tggaggccag gtctacatat acagcaattt   1380

atctcctttt gcctcatatt gcttattagc gacacttgca tcattgaaat cagactttta   1440

cttcacaggt tgtttatatt ctggatcaag taagggcttt agaggaggaa atgttacaaa   1500

gaatcaagca gcaagggcta aacgtgaagc ccaagattct tgtggtgagt tttgcaaaaa   1560

tatgcttaga caggttttga gattgatcgg agaagggatt aagatgatca agatctttgt   1620

ttcctgcttt catgatgtaa acaggtatct cgtctcatac cagatgctcg agggacaaca   1680

tgcaatcagg agatggaacc tattcttaac tcatcccatt ctcacatcct gagaattcca   1740
```

```
ttcaggactg agaaaggagt tcttcgccaa tgggtttctc ggtttgatat ctatccttac   1800

ttggagaact atgccaaggc aagtcttcta acaaaattac cacctattca tacactttat   1860

ttactttctt gaactaatcg tttggtttgt gacgtatatc attaggatgc ttctgctaag   1920

atacttgagc tcatggaagg taaaccagac ctcataattg ggaactacac tgatggaaat   1980

ttagtggcat ctctattggc caacaaactt ggagttactc aggttccgta gctgatcata   2040

tgatcatatt ttctacattg tttcttgata attaaatgga aatcttattg gatgataaca   2100

ttttagggaa ccattgctca tgcattagag aaaactaagt atgaagattc tgatgtgaag   2160

tggaagcagt ttgatcccaa gtaccacttt tcttgccaat ttactgccga tttattggca   2220

atgaatgctg ctgattttat cattaccagc acatatcaag aaatcgctgg aaggttagca   2280

ctgactctct cagtatattt ggcaacttaa tgaatttact gcagtggcca acactaaaag   2340

ctatcattcg tccttcagcg aaactaggcc tggacaatat gaaagtcaca cagcatttac   2400

catgccgggg ctttatagag ctgtttcagg catcaatgta tttgatccaa agttcaacat   2460

tgctgctcct ggggctgaac agtctaccta tttccctttc actgagaaac agaaacgatt   2520

cagcacattt cgtcctgcta ttaacgaatt actttacagt aatgaggaaa acaatgagca   2580

catgtaagtc taattgccca ttttcctaat ctaaccattg cttaaatcgt tctgttttta   2640

ccggatgtgt ggtacttatc agtaacattt ttttttggat cagtggattt cttgcagacc   2700

ggaaaaaacc aattatattt tcaatggcga gatttgatac agtgaagaac ctgtcaggct   2760

tgactgagtg gtatgggaag aataagaagt tgcggaactt ggtaaacctt gttattgttg   2820

ggggattctt cgatccatca aaatcaaaag accgggagga agcagctgaa atcaagaaga   2880

tgcatgaatt gattgagaaa taccagctca agggacaaat gagatggata gcagctcaaa   2940

ctgataaata tcgaaatagt gagctatacc gaactattgc tgacactaag ggagcttttg   3000

tccaaccggc tttatatgaa gcttttggac taaccgttat tgaagcaatg gattgtggat   3060

tgcctacgtt tgcaactaat caaggtggac ctgcagaaat cattgttgat ggggtttcag   3120

gtttccatat tgatccttac aatggggacg aatcaagcaa gaaaatagct gatttctttg   3180

agaagtgtaa ggttgattct aaatattgga acaggatatc tgagggaggt ctcaagcgca   3240

ttgaagaatg gtaacaaact agttccaagt ttaaaaaatg gaaaaaatgc ttatcatgtt   3300

atattttcgt ggttttaagt tctgcttcga tgcagttata cgtggaagat ttatgcaaac   3360

aaagtgttga atatgggatc aatctatgga ttttggagac aattcaatgt ggggcaaaag   3420

caggctaagc aaagatactt tgagatgttt tacaatcctc tcttcaggaa attggtaggt   3480

tgtatatgtt gaatacaatt tactaagatc ctcaaaatga ccaagaaata tacattgact   3540

atgctacttt tgtaatttca caggccaaaa gcgtgccgat cccacatgaa gagccattgc   3600

cacttgcaac atcagactct actcaatccc aagaattaaa actaccacta ccagttccag   3660

cagcagtagc taaagttctg ccattaacaa ggcatgcttt taacttaatt acttctctac   3720

ctagagtaac tggtaaagtg gatgtcaagt ga                                 3752
```

<210> SEQ ID NO 18
<211> LENGTH: 840
<212> TYPE: PRT
<213> ORGANISM: Nicotiana tabacum

<400> SEQUENCE: 18

```
Met Ala Ser Thr Val Ala Asp Ser Met Pro Asp Ala Leu Lys Gln Ser
1               5                   10                  15
```

```
Arg Tyr His Met Lys Arg Cys Phe Ala Arg Phe Ile Ala Met Gly Arg
            20                  25                  30

Arg Leu Met Lys Leu Lys His Leu Thr Glu Glu Ile Glu Glu Thr Ile
        35                  40                  45

Glu Asp Lys Ala Glu Arg Thr Arg Ile Leu Glu Gly Ser Leu Gly Lys
    50                  55                  60

Ile Met Ser Ser Thr Gln Glu Ala Ala Val Val Pro Pro Tyr Val Ala
65                  70                  75                  80

Phe Ala Val Arg His Asn Pro Gly Phe Trp Asp Tyr Val Lys Val Asn
                85                  90                  95

Ala Glu Thr Leu Ser Val Glu Ala Ile Ser Ala Arg Glu Tyr Leu Lys
            100                 105                 110

Phe Lys Glu Met Ile Phe Asp Glu Asp Trp Ala Lys Asp Asp Asn Ala
        115                 120                 125

Leu Glu Val Asp Phe Gly Ala Phe Asp Tyr Ser Asn Pro Arg Leu Ala
    130                 135                 140

Leu Ser Ser Ser Val Gly Asn Gly Leu Asn Phe Ile Ser Lys Val Leu
145                 150                 155                 160

Ser Ser Lys Phe Gly Gly Lys Pro Glu Asp Ala Gln Pro Leu Leu Asp
                165                 170                 175

Tyr Leu Leu Ala Leu Asn His Gln Gly Glu Asn Leu Met Ile Asn Glu
            180                 185                 190

Asn Leu Asn Gly Val Ala Lys Leu Gln Ala Ala Leu Ile Val Ala Glu
        195                 200                 205

Val Phe Val Ser Ser Phe Pro Lys Asp Thr Pro Tyr Lys Asp Phe Glu
    210                 215                 220

His Lys Leu Lys Glu Trp Gly Phe Asp Lys Gly Trp Gly His Asn Ala
225                 230                 235                 240

Gly Arg Val Arg Glu Thr Met Arg Leu Leu Ser Glu Ile Ile Gln Ala
                245                 250                 255

Pro Asp Pro Ile Asn Met Glu Ser Phe Phe Ser Lys Leu Pro Thr Thr
            260                 265                 270

Phe Asn Ile Val Ile Phe Ser Ile His Gly Tyr Phe Gly Gln Ala Asp
        275                 280                 285

Val Leu Gly Leu Pro Asp Thr Gly Gly Gln Val Val Tyr Ile Leu Asp
    290                 295                 300

Gln Val Arg Ala Leu Glu Glu Glu Met Leu Gln Arg Ile Lys Gln Gln
305                 310                 315                 320

Gly Leu Asn Val Lys Pro Lys Ile Leu Val Val Ser Arg Leu Ile Pro
                325                 330                 335

Asp Ala Arg Gly Thr Thr Cys Asn Gln Glu Met Glu Pro Ile Leu Asn
            340                 345                 350

Ser Ser His Ser His Ile Leu Arg Ile Pro Phe Arg Thr Glu Lys Gly
        355                 360                 365

Val Leu Arg Gln Trp Asp Ala Ser Ala Lys Ile Leu Glu Leu Met Glu
    370                 375                 380

Gly Lys Pro Asp Leu Ile Ile Gly Asn Tyr Thr Asp Gly Asn Leu Val
385                 390                 395                 400

Ala Ser Leu Leu Ala Asn Lys Leu Gly Val Thr Gln Gly Thr Ile Ala
                405                 410                 415

His Ala Leu Glu Lys Thr Lys Tyr Glu Asp Ser Asp Val Lys Trp Lys
            420                 425                 430
```

```
Gln Phe Asp Pro Lys Tyr His Phe Ser Cys Gln Phe Thr Ala Asp Leu
        435                 440                 445

Leu Ala Met Asn Ala Ala Asp Phe Ile Ile Thr Ser Thr Tyr Gln Glu
    450                 455                 460

Ile Ala Gly Ser Glu Thr Arg Pro Gly Gln Tyr Glu Ser His Thr Ala
465                 470                 475                 480

Phe Thr Met Pro Gly Leu Tyr Arg Ala Val Ser Gly Ile Asn Val Phe
                485                 490                 495

Asp Pro Lys Phe Asn Ile Ala Ala Pro Gly Ala Glu Gln Ser Thr Tyr
            500                 505                 510

Phe Pro Phe Thr Glu Lys Gln Lys Arg Phe Ser Thr Phe Arg Pro Ala
        515                 520                 525

Ile Asn Glu Leu Leu Tyr Ser Asn Glu Glu Asn Asn Glu His Ile Gly
    530                 535                 540

Phe Leu Ala Asp Arg Lys Lys Pro Ile Ile Phe Ser Met Ala Arg Phe
545                 550                 555                 560

Asp Thr Val Lys Asn Leu Ser Gly Leu Thr Glu Trp Tyr Gly Lys Asn
                565                 570                 575

Lys Lys Leu Arg Asn Leu Val Asn Leu Val Ile Val Gly Gly Phe Phe
            580                 585                 590

Asp Pro Ser Lys Ser Lys Asp Arg Glu Glu Ala Ala Glu Ile Lys Lys
        595                 600                 605

Met His Glu Leu Ile Glu Lys Tyr Gln Leu Lys Gly Gln Met Arg Trp
    610                 615                 620

Ile Ala Ala Gln Thr Asp Lys Tyr Arg Asn Ser Glu Leu Tyr Arg Thr
625                 630                 635                 640

Ile Ala Asp Thr Lys Gly Ala Phe Val Gln Pro Ala Leu Tyr Glu Ala
                645                 650                 655

Phe Gly Leu Thr Val Ile Glu Ala Met Asp Cys Gly Leu Pro Thr Phe
            660                 665                 670

Ala Thr Asn Gln Gly Gly Pro Ala Glu Ile Ile Val Asp Gly Val Ser
        675                 680                 685

Gly Phe His Ile Asp Pro Tyr Asn Gly Asp Glu Ser Ser Lys Lys Ile
    690                 695                 700

Ala Asp Phe Phe Glu Lys Cys Lys Val Asp Ser Lys Tyr Trp Asn Arg
705                 710                 715                 720

Ile Ser Glu Gly Gly Leu Lys Arg Ile Glu Glu Cys Tyr Thr Trp Lys
                725                 730                 735

Ile Tyr Ala Asn Lys Val Leu Asn Met Gly Ser Ile Tyr Gly Phe Trp
            740                 745                 750

Arg Gln Phe Asn Val Gly Gln Lys Gln Ala Lys Gln Arg Tyr Phe Glu
        755                 760                 765

Met Phe Tyr Asn Pro Leu Phe Arg Lys Leu Ala Lys Ser Val Pro Ile
    770                 775                 780

Pro His Glu Glu Pro Leu Pro Leu Ala Thr Ser Asp Ser Thr Gln Ser
785                 790                 795                 800

Gln Glu Leu Lys Leu Pro Leu Pro Val Pro Ala Ala Val Ala Lys Val
                805                 810                 815

Leu Pro Leu Thr Arg His Ala Phe Asn Leu Ile Thr Ser Leu Pro Arg
            820                 825                 830

Val Thr Gly Lys Val Asp Val Lys
        835                 840
```

<210> SEQ ID NO 19
<211> LENGTH: 3268
<212> TYPE: DNA
<213> ORGANISM: Nicotiana tabacum

<400> SEQUENCE: 19

```
atggcctcaa ctgttgctgg tagcatgcct gatgctttga aacaaagccg atatcatatg      60
aagagatgct tcgctaggtg aacacccttc ttgttctttt tgttttttcc ctctaccatt     120
tatgtcaaat ttcaatgcat aatgctaact actttttttc tttttgactt caaaattgga     180
cgtgaaaggt tcattgcaat gggaaggagg ttgatgaagc tgaaacattt aacagaagaa     240
atagaaaaaa ctattgaaga caaggcagaa agaaccaaga ttttggaggg ttcacttgga     300
aaaattatga gttccacaca ggtcagcacc atttaaccaa cttaattgaa taggaagaaa     360
aaaaaaagca aaagagttat tgcaaggcgt aacgatttcc tttgaaattt tcaggaggca     420
gctgttgtcc caccttatgt tgcttttgca gtaaggcaca atcctggctt ctgggattat     480
gtcaaagttg acgctgaaac tctctctgtg gaagctattt cagccaggga ctatctcaaa     540
ttcaaagaga tgatctttga tgaagattgg taactggaag attgtatcat tttaaagaaa     600
caatttttta atattcaaga ttagttttga tggttgaatg tgcaagcagg gcaaaggatg     660
aaaatgcact cgaagtagat tttggtgctt ttgactactc taatcatcgg ttagcccttt     720
cctcttctgt cggaaatggg ctaaacttca tctcgaaagt tttgtcttca aagtttggtg     780
gaaaggcaga agatgcccag cctttgcttg attacttact agctcttaat catcaaggag     840
aggtatggaa atggactacc ttcctttctt aaggaattat ataatgatgt atgttataaa     900
gatccttttt aaacattgac actttgcaga atctaatgat caatgagaat ctgaatggcg     960
tctctaagct tcaagcagca ttgatagtag ctgaagtttt tgtatcttcc tttcccaaag    1020
acacacctta taaagacttt gagcataagt aagcttttca aacgcttctg ttatcatatg    1080
caatatacca agaatatgtt gccttttgaa aagttgttta tgtttatgac ttgataatga    1140
aaatactagg ctcaaagaat ggggctttga gaaagggtgg ggtcacaatg caggaagagt    1200
aagagagaca atgagactgc tttccgagat aatccaagcg ccagatccca taaatatgga    1260
gtcctttttc agcaggcttc ctactacatt caacattgtt atcttctcca ttcatggtta    1320
ctttggccaa gcagatgtcc ttggtttgcc cgatactgga ggccaggttt acatacacag    1380
caatttatct ccttttgcct catatttact tattagcgac acttgcatta ttgaaatcac    1440
atttgtattt aacaggttgt ttatattctg gatcaagtaa gagccttaga ggaggaaatg    1500
ttacaaagaa tcaagcagca agggttaaat gtgaagccca agattcttgt ggtgagttat    1560
gcaaaaatat gcgtagccaa ggttttgaaa ttgttcagag gggattaaga tgatcgagat    1620
atttgtttcc ttcttccatt gatgtgtaca ggtcactcgt ctcattccag atgctcgagg    1680
gactacatgc aatcaggaga tggaacctat acttaactcg tcccattctc acatcctgag    1740
aattccattc aggacagaga aaggagttct tcgccaatgg gtttctcggt ttgatatcta    1800
tccttacttg gagaactatg ccaaggcaag tctcctacca aaattaccac ctattcatac    1860
actttattca gtttttttgag ctaatcattc tcatttgtca cgtatgtgat taggatgctt    1920
ctgctaagat acttgagctc atggaaggta aaccagacct cattattggg aactacactg    1980
atggaaattt agtggcatct ctattggcca acaaacttgg agttactcag gttctacagc    2040
tgatcattta tctgatcaga ttttctacat tgttttcttg ataattaaac ggaaatctta    2100
tgagattgta acattttagg gaaccattgc tcatgcatta gagaaaacca agtatgaaga    2160
```

```
ttctgatgtc aagtggaagc agtttgattc caagtaccac ttttcttgcc aattcactgc   2220

cgatttattg gcaatgaatg ctgctgattt tatcattacc agcacatatc aagaaatcgc   2280

aggaaggtta gcactgactc tctcagtata tttggcaact taatgaatgt actgcttgtg   2340

gccaacacta aaagctatta ctcgtccttc agcgaaacta ggcctggaca atatgaaagt   2400

cacacagcat ttaccatgcc ggggctttat agagctgttt caggcatcaa tgtatttgat   2460

ccaaagttca acattgctgc tcctggggct gaacagtctg cctatttccc cttcactgag   2520

aaacagaaac gattcagcgc gtttcgtcct gctattgagg aactacttta cagtaatgag   2580

caaaacaacg agcacatgta agtctaattg ccccattttc ctaatctaac cattgcttaa   2640

atgttctgtt tttacttgat atgtggtact tatcagtgat attttttatt ggaacagtgg   2700

atttcttgca gaccgtaaaa aaccaattat attttcaatg gcaagatttg atacggtgaa   2760

gaacttgtca ggcttgactg agtggtatgg gaagaataag aagttgcgga acttggttaa   2820

cctcgttatc gttgggggat tcttcgatcc atcaaaatca aaagaccggg aggaagcagc   2880

tgaaatcaag aagatgcatg aattgattga gaaatacaag ctcaagggac aaatgagatg   2940

gatagcagct caaactgata aatatcaaaa cagtgagcta tatcgaacta ttgctgacac   3000

taaaggagct ttcgtccaac cggctttata tgaagctttt ggactaactg ttattgaagc   3060

aatgaattgt ggactgccta catttgctac taatcaaggc ggacctgcag aaatcattgt   3120

tgatggggtt tcaggcttcc atattgatcc ttacaatggg gatgaatcga gcaagaaaat   3180

agctgatttc tttgagaagt gtaaggttga ttctaaatat tggaacaaga tatgtggagg   3240

aggtctcaag cgcattgaag aatggtaa                                      3268
```

<210> SEQ ID NO 20
<211> LENGTH: 732
<212> TYPE: PRT
<213> ORGANISM: Nicotiana tabacum

<400> SEQUENCE: 20

```
Met Ala Ser Thr Val Ala Gly Ser Met Pro Asp Ala Leu Lys Gln Ser
1               5                   10                  15

Arg Tyr His Met Lys Arg Cys Phe Ala Arg Phe Ile Ala Met Gly Arg
            20                  25                  30

Arg Leu Met Lys Leu Lys His Leu Thr Glu Glu Ile Glu Lys Thr Ile
        35                  40                  45

Glu Asp Lys Ala Glu Arg Thr Lys Ile Leu Glu Gly Ser Leu Gly Lys
    50                  55                  60

Ile Met Ser Ser Thr Gln Glu Ala Ala Val Val Pro Pro Tyr Val Ala
65                  70                  75                  80

Phe Ala Val Arg His Asn Pro Gly Phe Trp Asp Tyr Val Lys Val Asp
                85                  90                  95

Ala Glu Thr Leu Ser Val Glu Ala Ile Ser Ala Arg Asp Tyr Leu Lys
            100                 105                 110

Phe Lys Glu Met Ile Phe Asp Glu Asp Trp Ala Lys Asp Glu Asn Ala
        115                 120                 125

Leu Glu Val Asp Phe Gly Ala Phe Asp Tyr Ser Asn His Arg Leu Ala
    130                 135                 140

Leu Ser Ser Ser Val Gly Asn Gly Leu Asn Phe Ile Ser Lys Val Leu
145                 150                 155                 160

Ser Ser Lys Phe Gly Gly Lys Ala Glu Asp Ala Gln Pro Leu Leu Asp
                165                 170                 175
```

-continued

Tyr Leu Leu Ala Leu Asn His Gln Gly Glu Asn Leu Met Ile Asn Glu
180 185 190

Asn Leu Asn Gly Val Ser Lys Leu Gln Ala Ala Leu Ile Val Ala Glu
195 200 205

Val Phe Val Ser Ser Phe Pro Lys Asp Thr Pro Tyr Lys Asp Phe Glu
210 215 220

His Lys Leu Lys Glu Trp Gly Phe Glu Lys Gly Trp Gly His Asn Ala
225 230 235 240

Gly Arg Val Arg Glu Thr Met Arg Leu Leu Ser Glu Ile Ile Gln Ala
245 250 255

Pro Asp Pro Ile Asn Met Glu Ser Phe Phe Ser Arg Leu Pro Thr Thr
260 265 270

Phe Asn Ile Val Ile Phe Ser Ile His Gly Tyr Phe Gly Gln Ala Asp
275 280 285

Val Leu Gly Leu Pro Asp Thr Gly Gly Gln Val Val Tyr Ile Leu Asp
290 295 300

Gln Val Arg Ala Leu Glu Glu Glu Met Leu Gln Arg Ile Lys Gln Gln
305 310 315 320

Gly Leu Asn Val Lys Pro Lys Ile Leu Val Val Thr Arg Leu Ile Pro
325 330 335

Asp Ala Arg Gly Thr Thr Cys Asn Gln Glu Met Glu Pro Ile Leu Asn
340 345 350

Ser Ser His Ser His Ile Leu Arg Ile Pro Phe Arg Thr Glu Lys Gly
355 360 365

Val Leu Arg Gln Trp Asp Ala Ser Ala Lys Ile Leu Glu Leu Met Glu
370 375 380

Gly Lys Pro Asp Leu Ile Ile Gly Asn Tyr Thr Asp Gly Asn Leu Val
385 390 395 400

Ala Ser Leu Leu Ala Asn Lys Leu Gly Val Thr Gln Gly Thr Ile Ala
405 410 415

His Ala Leu Glu Lys Thr Lys Tyr Glu Asp Ser Asp Val Lys Trp Lys
420 425 430

Gln Phe Asp Ser Lys Tyr His Phe Ser Cys Gln Phe Thr Ala Asp Leu
435 440 445

Leu Ala Met Asn Ala Ala Asp Phe Ile Ile Thr Ser Thr Tyr Gln Glu
450 455 460

Ile Ala Gly Ser Glu Thr Arg Pro Gly Gln Tyr Glu Ser His Thr Ala
465 470 475 480

Phe Thr Met Pro Gly Leu Tyr Arg Ala Val Ser Gly Ile Asn Val Phe
485 490 495

Asp Pro Lys Phe Asn Ile Ala Ala Pro Gly Ala Glu Gln Ser Ala Tyr
500 505 510

Phe Pro Phe Thr Glu Lys Gln Lys Arg Phe Ser Ala Phe Arg Pro Ala
515 520 525

Ile Glu Glu Leu Leu Tyr Ser Asn Glu Gln Asn Asn Glu His Ile Gly
530 535 540

Phe Leu Ala Asp Arg Lys Lys Pro Ile Ile Phe Ser Met Ala Arg Phe
545 550 555 560

Asp Thr Val Lys Asn Leu Ser Gly Leu Thr Glu Trp Tyr Gly Lys Asn
565 570 575

Lys Lys Leu Arg Asn Leu Val Asn Leu Val Ile Val Gly Gly Phe Phe
580 585 590

Asp Pro Ser Lys Ser Lys Asp Arg Glu Glu Ala Ala Glu Ile Lys Lys

```
        595                 600                 605

Met His Glu Leu Ile Glu Lys Tyr Lys Leu Lys Gly Gln Met Arg Trp
    610                 615                 620

Ile Ala Ala Gln Thr Asp Lys Tyr Gln Asn Ser Glu Leu Tyr Arg Thr
625                 630                 635                 640

Ile Ala Asp Thr Lys Gly Ala Phe Val Gln Pro Ala Leu Tyr Glu Ala
                645                 650                 655

Phe Gly Leu Thr Val Ile Glu Ala Met Asn Cys Gly Leu Pro Thr Phe
            660                 665                 670

Ala Thr Asn Gln Gly Gly Pro Ala Glu Ile Ile Val Asp Gly Val Ser
        675                 680                 685

Gly Phe His Ile Asp Pro Tyr Asn Gly Asp Glu Ser Ser Lys Lys Ile
    690                 695                 700

Ala Asp Phe Phe Glu Lys Cys Lys Val Asp Ser Lys Tyr Trp Asn Lys
705                 710                 715                 720

Ile Cys Gly Gly Gly Leu Lys Arg Ile Glu Glu Trp
                725                 730


<210> SEQ ID NO 21
<211> LENGTH: 3937
<212> TYPE: DNA
<213> ORGANISM: Nicotiana tabacum

<400> SEQUENCE: 21

atggctactg caccagccct aaatagatca gagtccatag ctgatagcat gccagaggcc     60

ttaaggcaaa gccggtacca catgaagaaa tgttttgcca agtacataga gcaaggaaag    120

aggatgatga aacttcataa cttgatggat gagttggaga aagtaattga tgatcctgct    180

gaaaggaacc atgttttgga aggcttactt ggctacatat tatgcactac aatggtatag    240

ctagattcat atgtacttat gatgccctta tattgtttcc tgatgtatta ctcttaaaac    300

cttctttgat caaatttaca ggaggctgca gttgttcctc cctacattgc ctttgccacg    360

agacagaatc ctggattctg ggaatatgtg aaagtgaatg ctaatgatct ttctgttgag    420

ggtattacag ctacagaata cttgaaattc aaggaaatga tagttgatga atgctggtat    480

agtatacgtt gcagcttatc atacctttg tggttttata acttcaatca gaaaactcat    540

cagagttacc tttgtgtgaa catgaaatgc agggcaaaag atgaatatgc actggaaatt    600

gattttggag cagtagactt ctcaacgcct cgactgaccc tatcctcttc aattggcaat    660

ggtctcagtt atgtttccaa gtttctaact tcaaagctaa atgctacctc cgcgagtgca    720

cagtgtctgg ttgactactt gctcactttg aatcatcaag gagatgtacg tcaacaaaaa    780

tcaaactcca taagtaaact tgtcaactct aagaagaaaa aataggaaaa gaagattcac    840

gtaacaaatt ttctttatgt tcaactgcag aaactgatga tcaatgagac actcagcact    900

gtctcaaagc ttcaggctgc actggttgta gcagaagcat ctatttcctc tttaccaaca    960

gatacaccat atgagagctt tgagctaagg tgatttgttt tttcctctac ttccctccac   1020

ttgtgccatg ctacgtagta ctaagtaact tcaattcttg taaagattca aacagtgggg   1080

ttttgagaaa ggatggggtg atacagctga aagggtcagc gacaccatga gaacactgtc   1140

tgaggtgctt caggcaccag atccattgaa cattcagaag ttctttggaa gggttccaac   1200

tgttttcaat attgtattgt tctctgtcca tggatacttt ggccaagcag atgttcttgg   1260

cttgccagac actggtggtc aggtaagcat ttaatagctt ttacatttaa cttctatgca   1320

ttgacaataa aataattttt aacagtttga ccacttctgc tcttgttcaa caggtagttt   1380
```

```
atgttttgga tcaagttgta gcttttgaag aagaaatgct acaaagaatt aaacagcagg   1440
ggctcaatat taagcctcaa attcttgtgg tgagttccta gacaatcgac gtgactatgc   1500
aattatgtag aggctgttta gaaaagttaa tatcatatgt tgattgcaca gttaacccga   1560
ctgattccgg atgcaaaagg aacaaagtgc aaccaggaac tagaaccaat caagaataca   1620
aaacattcac acatcctcag agttccattt aggacagaaa aaggagtgct taatcaatgg   1680
gtttcacgat ttgatatcta tccatatctg gagagatata ctcaggtatg tatttttata   1740
tcaaccttgc tcatcaaaga tgtgttgttt cctcaattcc atttttcccc ttggcaaaag   1800
gatgctgctg acaaaatcgt cgagctaatg gaaggcaaac ctgatctaat cattggtaac   1860
tacactgatg ggaatctagt ggcttcacta atggctagaa aacttgggat aactctggta   1920
acttttctta atcatatttg atgttgcttc ttctccaagt tagttcttaa tctccactga   1980
cctagaccat ctttgcaaca gggaactatt gctcatgctt tggagaagac aaaatatgaa   2040
gactctgaca taaaattgaa ggaactcgat ccgaagtacc acttctcttg ccaattcaca   2100
gctgatttga ttgcaatgaa ttcagcagat ttcattatca ctagcacata ccaagaaata   2160
gctggaaggt aagaattaga gctaataagt aatgcattca tatgtatttc agcatcgctc   2220
tttcaccatc atcgaataca caccactact cagtaaatgt atttgctcaa aagtttgcaa   2280
cttaatggat ctcattcttg aatgcttcaa catatgcagc aaagataaac caggacagta   2340
tgagagccat agtgcattta cccttccagg gctttacaga gttgcttcag gtatcaatgt   2400
ctttgatcca aaatttaata ttgctgcacc tggggcagac cagtcggtgt atttccctta   2460
cacagaaaag cagaagcgtt tgactgcttt ccgccctgcc attgaggaac tgctttttag   2520
taaagtggac aatgacgagc acgtgtaagt ctaagtgtta aacttcagct tagtgcctag   2580
aacatcccac tgctctatgt attgatgttt cacttgtttc aaacagtgga tatttagaag   2640
acagaaagaa acctatcctg tttaccatgg caaggctgga cacagtgaag aacacatctg   2700
gactaacaga atggtatggc aagaacaaga ggctcagaag cttagttaac cttgttgtgg   2760
ttggtggttc ctttgatcct acaaaatcca aggataggga agaagcagct gaaataaaaa   2820
agatgcacat gctgatagag aaataccagc ttaagggtca gattagatgg atagcagctc   2880
agactgacag atacagaaat agtgaactct accgcacaat agcagattcc aaaggagctt   2940
ttgtgcagcc tgcattgtat gaagcatttg gtctaacagt cattgaggca atgaactgtg   3000
gattaccaac ctttgctacc aaccaaggtg gccctgctga gattattgtt gatggggtct   3060
caggctttca tattgatcca aataatgggg atgaatcaag caacaaaatt gccaactttt   3120
tccaaaaatg cagggaggat cctgagtatt ggaacaggat ttcagtccag ggtctaaacc   3180
gtatatatga atggtaactc acagataagc cattcaaatt gcaaagaggc acatatcttg   3240
cagaaaattt cttaatcctt aaatcctaat tttttgcagt tacacatgga agatctatgc   3300
aaacaaggta ttgaatatgg ggtccatcta tactttttgg aggacattgt acagagatca   3360
gaaacaagca aagcaaagat acatcgagac tttctacaat cttgagttta ggaacttggt   3420
atagtgctgc atgacattga cagtatacca caaacatctt tatgagatga attactttta   3480
ataaaattgt ttttaacctt tgcttcctta atggcactta ttgcaggtaa aaaatgtgcc   3540
tatcagaaag gacgaaacac cacaaggacc aaaggagagg gagaaagtta agccacagat   3600
atcacaaagg catgctctaa agcttttgcc tacagttttt caagagaccc tagtatattc   3660
tagtactaaa ttagaattat acagcatgca gcttttgctg ttcacctttc taaatcacca   3720
```

```
gttgtgtcaa tcaagttgac aaaatcaata aattgggatt ttccctttcc tatgcttgat   3780

tgttattact cctactttgt ttatggtagt cttccttcat tgttttctcc tgtacttctt   3840

ttactacaac tgtactgaca tactaattat ttctgtgtac caggcgctca caatcaaggt   3900

tgcagaagta agattagata aaattgctac tgcatga                            3937


<210> SEQ ID NO 22
<211> LENGTH: 860
<212> TYPE: PRT
<213> ORGANISM: Nicotiana tabacum

<400> SEQUENCE: 22

Met Ala Thr Ala Pro Ala Leu Asn Arg Ser Glu Ser Ile Ala Asp Ser
1               5                   10                  15

Met Pro Glu Ala Leu Arg Gln Ser Arg Tyr His Met Lys Lys Cys Phe
            20                  25                  30

Ala Lys Tyr Ile Glu Gln Gly Lys Arg Met Met Lys Leu His Asn Leu
        35                  40                  45

Met Asp Glu Leu Glu Lys Val Ile Asp Asp Pro Ala Glu Arg Asn His
    50                  55                  60

Val Leu Glu Gly Leu Leu Gly Tyr Ile Leu Cys Thr Thr Met Glu Ala
65                  70                  75                  80

Ala Val Val Pro Pro Tyr Ile Ala Phe Ala Thr Arg Gln Asn Pro Gly
                85                  90                  95

Phe Trp Glu Tyr Val Lys Val Asn Ala Asn Asp Leu Ser Val Glu Gly
            100                 105                 110

Ile Thr Ala Thr Glu Tyr Leu Lys Phe Lys Glu Met Ile Val Asp Glu
        115                 120                 125

Cys Trp Ala Lys Asp Glu Tyr Ala Leu Glu Ile Asp Phe Gly Ala Val
    130                 135                 140

Asp Phe Ser Thr Pro Arg Leu Thr Leu Ser Ser Ser Ile Gly Asn Gly
145                 150                 155                 160

Leu Ser Tyr Val Ser Lys Phe Leu Thr Ser Lys Leu Asn Ala Thr Ser
                165                 170                 175

Ala Ser Ala Gln Cys Leu Val Asp Tyr Leu Leu Thr Leu Asn His Gln
            180                 185                 190

Gly Asp Lys Leu Met Ile Asn Glu Thr Leu Ser Thr Val Ser Lys Leu
        195                 200                 205

Gln Ala Ala Leu Val Val Ala Glu Ala Ser Ile Ser Ser Leu Pro Thr
    210                 215                 220

Asp Thr Pro Tyr Glu Ser Phe Glu Leu Arg Phe Lys Gln Trp Gly Phe
225                 230                 235                 240

Glu Lys Gly Trp Gly Asp Thr Ala Glu Arg Val Ser Asp Thr Met Arg
                245                 250                 255

Thr Leu Ser Glu Val Leu Gln Ala Pro Asp Pro Leu Asn Ile Gln Lys
            260                 265                 270

Phe Phe Gly Arg Val Pro Thr Val Phe Asn Ile Val Leu Phe Ser Val
        275                 280                 285

His Gly Tyr Phe Gly Gln Ala Asp Val Leu Gly Leu Pro Asp Thr Gly
    290                 295                 300

Gly Gln Val Val Tyr Val Leu Asp Gln Val Val Ala Phe Glu Glu Glu
305                 310                 315                 320

Met Leu Gln Arg Ile Lys Gln Gln Gly Leu Asn Ile Lys Pro Gln Ile
                325                 330                 335
```

```
Leu Val Leu Thr Arg Leu Ile Pro Asp Ala Lys Gly Thr Lys Cys Asn
            340                 345                 350

Gln Glu Leu Glu Pro Ile Lys Asn Thr Lys His Ser His Ile Leu Arg
        355                 360                 365

Val Pro Phe Arg Thr Glu Lys Gly Val Leu Asn Gln Trp Val Ser Arg
    370                 375                 380

Phe Asp Ile Tyr Pro Tyr Leu Glu Arg Tyr Thr Gln Asp Ala Ala Asp
385                 390                 395                 400

Lys Ile Val Glu Leu Met Glu Gly Lys Pro Asp Leu Ile Ile Gly Asn
                405                 410                 415

Tyr Thr Asp Gly Asn Leu Val Ala Ser Leu Met Ala Arg Lys Leu Gly
            420                 425                 430

Ile Thr Leu Gly Thr Ile Ala His Ala Leu Glu Lys Thr Lys Tyr Glu
        435                 440                 445

Asp Ser Asp Ile Lys Leu Lys Glu Leu Asp Pro Lys Tyr His Phe Ser
    450                 455                 460

Cys Gln Phe Thr Ala Asp Leu Ile Ala Met Asn Ser Ala Asp Phe Ile
465                 470                 475                 480

Ile Thr Ser Thr Tyr Gln Glu Ile Ala Gly Ser Lys Asp Lys Pro Gly
                485                 490                 495

Gln Tyr Glu Ser His Ser Ala Phe Thr Leu Pro Gly Leu Tyr Arg Val
            500                 505                 510

Ala Ser Gly Ile Asn Val Phe Asp Pro Lys Phe Asn Ile Ala Ala Pro
        515                 520                 525

Gly Ala Asp Gln Ser Val Tyr Phe Pro Tyr Thr Glu Lys Gln Lys Arg
    530                 535                 540

Leu Thr Ala Phe Arg Pro Ala Ile Glu Glu Leu Leu Phe Ser Lys Val
545                 550                 555                 560

Asp Asn Asp Glu His Val Gly Tyr Leu Glu Asp Arg Lys Lys Pro Ile
                565                 570                 575

Leu Phe Thr Met Ala Arg Leu Asp Thr Val Lys Asn Thr Ser Gly Leu
            580                 585                 590

Thr Glu Trp Tyr Gly Lys Asn Lys Arg Leu Arg Ser Leu Val Asn Leu
        595                 600                 605

Val Val Val Gly Gly Ser Phe Asp Pro Thr Lys Ser Lys Asp Arg Glu
    610                 615                 620

Glu Ala Ala Glu Ile Lys Lys Met His Met Leu Ile Glu Lys Tyr Gln
625                 630                 635                 640

Leu Lys Gly Gln Ile Arg Trp Ile Ala Ala Gln Thr Asp Arg Tyr Arg
                645                 650                 655

Asn Ser Glu Leu Tyr Arg Thr Ile Ala Asp Ser Lys Gly Ala Phe Val
            660                 665                 670

Gln Pro Ala Leu Tyr Glu Ala Phe Gly Leu Thr Val Ile Glu Ala Met
        675                 680                 685

Asn Cys Gly Leu Pro Thr Phe Ala Thr Asn Gln Gly Gly Pro Ala Glu
    690                 695                 700

Ile Ile Val Asp Gly Val Ser Gly Phe His Ile Asp Pro Asn Asn Gly
705                 710                 715                 720

Asp Glu Ser Ser Asn Lys Ile Ala Asn Phe Phe Gln Lys Cys Arg Glu
                725                 730                 735

Asp Pro Glu Tyr Trp Asn Arg Ile Ser Val Gln Gly Leu Asn Arg Ile
            740                 745                 750

Tyr Glu Cys Tyr Thr Trp Lys Ile Tyr Ala Asn Lys Val Leu Asn Met
```

```
        755                 760                 765

Gly Ser Ile Tyr Thr Phe Trp Arg Thr Leu Tyr Arg Asp Gln Lys Gln
    770                 775                 780

Ala Lys Gln Arg Tyr Ile Glu Thr Phe Tyr Asn Leu Glu Phe Arg Asn
785                 790                 795                 800

Leu Val Lys Asn Val Pro Ile Arg Lys Asp Glu Thr Pro Gln Gly Pro
                805                 810                 815

Lys Glu Arg Glu Lys Val Lys Pro Gln Ile Ser Gln Arg His Ala Leu
            820                 825                 830

Lys Leu Leu Pro Thr Val Phe Gln Glu Thr Leu Ala Leu Thr Ile Lys
        835                 840                 845

Val Ala Glu Val Arg Leu Asp Lys Ile Ala Thr Ala
    850                 855                 860


<210> SEQ ID NO 23
<211> LENGTH: 3905
<212> TYPE: DNA
<213> ORGANISM: Nicotiana tabacum

<400> SEQUENCE: 23

atggctactg caccagccct gaaaagatca gagtccatag ctgatagcat gccagaggcc      60

ttaaggcaaa gccggtacca catgaagaaa tgttttgcca agtacataga gcaaggcaag     120

aggatgatga aacttcataa cttgatggat gaattggaga aagtaattga tgatcctgct     180

gaaaggaacc atgttttgga aggcttactt ggctacatat tatgtactac aatggtatag     240

ctagattcat atgtacttat gatgtcctta tattgtttcc ggaggcatta ttcttaaatc     300

cttctttgat caaatttgta ggaggctgca gttgttcctc cctatattgc cttcgccacg     360

agacagaatc ctggattctg ggaatatgtg aaagtcaatg ctaatgatct ttctgttgag     420

ggtattacag ctacagatta cttgaaattc aaggaaatga tagttgatga aagctggtat     480

agaatacttt gcagcttatc atacctttg tggttttata atttcaatca gaaaactcat      540

cagagttacc tttgtgtgaa catgacatgc agggcaaaag atgaatatgc actggaaatt     600

gattttggag cagtagactt ctcaacgcct cgactgaccc tatcctcttc aattggaaat     660

ggtctcagtt atgtttccaa gtttctaact tcaaagctaa atgctacctc agcgagtgca     720

cagtgtctgg ttgactactt gctcactttg aatcaccaag gagatgtacg tcaacaaaaa     780

tcaaactcca taagtaaact tgtcaactct aagaagtaaa aataggaaaa gaagattcat     840

gtaacaaatt ttctttatgt tcaactgtag aaactgatga tcaatgagac actcggcact     900

gtctcaaagc ttcaggctgc actggttgta gcagaagcat ctatttcctc cttaccaaca     960

gatacaccat accagagctt tgagctaagg tgatttgttt tttcctctac ttccttccac    1020

ttttggtgtg ctacatagta ctaagtaact tcaattcttg taaagattca aacagtgggg    1080

ttttgagaaa ggatggggtg atacagctga aagggtccgc gacaccatga gaacactttc    1140

tgaggtactt caggcgccag atccattgaa cattgagaag ttctttggga gggttccaac    1200

tgttttcaat attgtattgt tctctgttca tggatacttt ggccaagcaa atgttcttgg    1260

cttgccagac acaggtggtc aggtaagcat ctaatagctt ttacatttaa cttctatgca    1320

ttgacaataa aataacttct acactaccaa ataattttg aaagtttgac cacttcggct     1380

cttgttcaac aggtggttta tgttttggat caagttgtag cttttgaaga agaaatgctc    1440

caaagaatta aacagcaggg gctcaatatt aagcctcaaa ttcttgtggt gagctcctag    1500

acaatgacgt gactatgcaa ttaagtagag gctgtttaga aaagttaata tcatatgttg    1560
```

```
attgcacagt taacccgact gattccggac gccaaaggaa caaagtgcaa ccaggaacta   1620
gaaccaatca agaatacaaa acattcacac atcctcagag ttccatttag gacagaaaaa   1680
ggagtgctta atcaatgggt ttcacgattt gatatctatc catatctgga gagatatact   1740
caggtgtgta tttttatatc aaccctgctc atcaaagatg tgttgtttcc tcaattccat   1800
ttttcgcctt gacaaaagga cgctgctgac aaaatcatcg agctaatgga aggcaaacct   1860
gatctaatca ttggtaacta cactgatggg aatctagtgg cttctctaat ggctagaaag   1920
cttgggataa ctctggtaac ttttcttatc atatttgatg ttgtttcttc tccaagttgg   1980
ttcttaatgt caactaaccc agaccatctt tgtaacaggg aactattgct catgctctgg   2040
agaagacaaa atatgaagac tctgacatca aattgaagga actcgatccg aagtaccact   2100
tttcttgcca attcacagct gatttgattg caatgaattc agcagatttc attatcacaa   2160
gcacatatca agaaatagcc ggaaggtaag aattggaact acggaagcag agagctaata   2220
agtagtgcac tcatatattt cagcatcgct ctttcgcata atcgaataca caccactact   2280
cagtaaatgt acttgctcaa aagtttacaa gtttatggat cttattcttg aatgcttcaa   2340
catatgcagc aaagataggc caggacagta tgagagccat agtgcattta cccttccagg   2400
gctttacaga gttgcttcag gcatcaatgt ctttgatcct aaatttaata ttgctgcacc   2460
tggggcagac caatcggtgt atttccctta cacagaaaag cagacgcgtt tgactgcttt   2520
ccgccctgcc attgaggaac tgctttttag taaagtggac aatgacgagc acatgtaagt   2580
cttagtgtta aacttcagct ttcagcttag tgcctagaac attccactgg ctctatgtat   2640
taatgtttca cttgtttcaa acacagtgga tatttagaag acagaaagaa acctatcctg   2700
tttaccatgg caaggctgga cacagtgaag aacacatctg gactaacaga atggtatggc   2760
aagaacaaga ggctcagaag cttagttaac cttgttgtgg ttggtggttc ctttgatcct   2820
acaaaatcca aggatagaga agaagcagct gaaataaaaa agatgcacat gctgatagag   2880
aaataccagc ttaagggtca gatcagatgg atagcagctc agactgacag atatagaaac   2940
agtgaactct accgcacaat agcagattcc aaaggagctt ttgtgcagcc tgcattatat   3000
gaagcatttg gtctaacagt cattgaggca atgaactgtg gattaccaac ctttgctacc   3060
aaccaaggtg gccctgctga gattattgtt gatggggtct caggctttca tattgatcca   3120
aataatgggg atgaatcaag caacaaagtt gccaactttt tccaaaaatg cagggaggat   3180
cctgagtatt ggaacaggat ttcagtccag ggtctaaacc gtatatatga atggtaactc   3240
acagataagc cattcaaatt gcaaagaggc acatatcttg ctgaaaattt cttaatcctt   3300
taatcctaaa attttgcagt tacacatgga agatctatgc aaacaaggta ttgaatatgg   3360
ggtccatcta tactttttgg aggacattgt acagagatca gaaacaagca aagcaaagat   3420
acatcgagac tttctacaat cttgagttta ggaacttggt atagtgctgc atgacattga   3480
cagtatacca caaacatctt tatgagatga attactttta ataaaattgt ttttaacctt   3540
tgcctcctta atgacactta ttgcaggtaa aaaatgtgcc tatcagacag gacgaaacac   3600
cacaaggacc aaaggagagg agggagaaag ttaagccaca gatatcacaa aggcatgctc   3660
taaagctttt gcctatagtt tttcaggaga ccctagtata ttctagtact aaattagaat   3720
tatacagcat gcagcttgct tctgctgttc acctttctaa atcaccagtt atgtcaatca   3780
agttgacaaa atcaataaat tcggcttttc cctttcctat gcttgattgt tattactcct   3840
acttcgttta tggtagtctt ccttcattgt tttctcctgt acttctttta ctacaactgt   3900
```

```
actga                                                                 3905


<210> SEQ ID NO 24
<211> LENGTH: 913
<212> TYPE: PRT
<213> ORGANISM: Nicotiana tabacum

<400> SEQUENCE: 24

Met Ala Thr Ala Pro Ala Leu Lys Arg Ser Glu Ser Ile Ala Asp Ser
1               5                   10                  15

Met Pro Glu Ala Leu Arg Gln Ser Arg Tyr His Met Lys Lys Cys Phe
            20                  25                  30

Ala Lys Tyr Ile Glu Gln Gly Lys Arg Met Met Lys Leu His Asn Leu
        35                  40                  45

Met Asp Glu Leu Glu Lys Val Ile Asp Asp Pro Ala Glu Arg Asn His
    50                  55                  60

Val Leu Glu Gly Leu Leu Gly Tyr Ile Leu Cys Thr Thr Met Glu Ala
65                  70                  75                  80

Ala Val Val Pro Pro Tyr Ile Ala Phe Ala Thr Arg Gln Asn Pro Gly
                85                  90                  95

Phe Trp Glu Tyr Val Lys Val Asn Ala Asn Asp Leu Ser Val Glu Gly
            100                 105                 110

Ile Thr Ala Thr Asp Tyr Leu Lys Phe Lys Glu Met Ile Val Asp Glu
        115                 120                 125

Ser Trp Ala Lys Asp Glu Tyr Ala Leu Glu Ile Asp Phe Gly Ala Val
    130                 135                 140

Asp Phe Ser Thr Pro Arg Leu Thr Leu Ser Ser Ser Ile Gly Asn Gly
145                 150                 155                 160

Leu Ser Tyr Val Ser Lys Phe Leu Thr Ser Lys Leu Asn Ala Thr Ser
                165                 170                 175

Ala Ser Ala Gln Cys Leu Val Asp Tyr Leu Leu Thr Leu Asn His Gln
            180                 185                 190

Gly Asp Lys Leu Met Ile Asn Glu Thr Leu Gly Thr Val Ser Lys Leu
        195                 200                 205

Gln Ala Ala Leu Val Val Ala Glu Ala Ser Ile Ser Ser Leu Pro Thr
    210                 215                 220

Asp Thr Pro Tyr Gln Ser Phe Glu Leu Arg Phe Lys Gln Trp Gly Phe
225                 230                 235                 240

Glu Lys Gly Trp Gly Asp Thr Ala Glu Arg Val Arg Asp Thr Met Arg
                245                 250                 255

Thr Leu Ser Glu Val Leu Gln Ala Pro Asp Pro Leu Asn Ile Glu Lys
            260                 265                 270

Phe Phe Gly Arg Val Pro Thr Val Phe Asn Ile Val Leu Phe Ser Val
        275                 280                 285

His Gly Tyr Phe Gly Gln Ala Asn Val Leu Gly Leu Pro Asp Thr Gly
    290                 295                 300

Gly Gln Val Val Tyr Val Leu Asp Gln Val Val Ala Phe Glu Glu Glu
305                 310                 315                 320

Met Leu Gln Arg Ile Lys Gln Gln Gly Leu Asn Ile Lys Pro Gln Ile
                325                 330                 335

Leu Val Leu Thr Arg Leu Ile Pro Asp Ala Lys Gly Thr Lys Cys Asn
            340                 345                 350

Gln Glu Leu Glu Pro Ile Lys Asn Thr Lys His Ser His Ile Leu Arg
        355                 360                 365
```

```
Val Pro Phe Arg Thr Glu Lys Gly Val Leu Asn Gln Trp Val Ser Arg
    370                 375                 380

Phe Asp Ile Tyr Pro Tyr Leu Glu Arg Tyr Thr Gln Asp Ala Ala Asp
385                 390                 395                 400

Lys Ile Ile Glu Leu Met Glu Gly Lys Pro Asp Leu Ile Ile Gly Asn
                405                 410                 415

Tyr Thr Asp Gly Asn Leu Val Ala Ser Leu Met Ala Arg Lys Leu Gly
            420                 425                 430

Ile Thr Leu Gly Thr Ile Ala His Ala Leu Glu Lys Thr Lys Tyr Glu
        435                 440                 445

Asp Ser Asp Ile Lys Leu Lys Glu Leu Asp Pro Lys Tyr His Phe Ser
    450                 455                 460

Cys Gln Phe Thr Ala Asp Leu Ile Ala Met Asn Ser Ala Asp Phe Ile
465                 470                 475                 480

Ile Thr Ser Thr Tyr Gln Glu Ile Ala Gly Ser Lys Asp Arg Pro Gly
                485                 490                 495

Gln Tyr Glu Ser His Ser Ala Phe Thr Leu Pro Gly Leu Tyr Arg Val
            500                 505                 510

Ala Ser Gly Ile Asn Val Phe Asp Pro Lys Phe Asn Ile Ala Ala Pro
        515                 520                 525

Gly Ala Asp Gln Ser Val Tyr Phe Pro Tyr Thr Glu Lys Gln Thr Arg
    530                 535                 540

Leu Thr Ala Phe Arg Pro Ala Ile Glu Glu Leu Leu Phe Ser Lys Val
545                 550                 555                 560

Asp Asn Asp Glu His Ile Gly Tyr Leu Glu Asp Arg Lys Lys Pro Ile
                565                 570                 575

Leu Phe Thr Met Ala Arg Leu Asp Thr Val Lys Asn Thr Ser Gly Leu
            580                 585                 590

Thr Glu Trp Tyr Gly Lys Asn Lys Arg Leu Arg Ser Leu Val Asn Leu
        595                 600                 605

Val Val Val Gly Gly Ser Phe Asp Pro Thr Lys Ser Lys Asp Arg Glu
    610                 615                 620

Glu Ala Ala Glu Ile Lys Lys Met His Met Leu Ile Glu Lys Tyr Gln
625                 630                 635                 640

Leu Lys Gly Gln Ile Arg Trp Ile Ala Ala Gln Thr Asp Arg Tyr Arg
                645                 650                 655

Asn Ser Glu Leu Tyr Arg Thr Ile Ala Asp Ser Lys Gly Ala Phe Val
            660                 665                 670

Gln Pro Ala Leu Tyr Glu Ala Phe Gly Leu Thr Val Ile Glu Ala Met
        675                 680                 685

Asn Cys Gly Leu Pro Thr Phe Ala Thr Asn Gln Gly Gly Pro Ala Glu
    690                 695                 700

Ile Ile Val Asp Gly Val Ser Gly Phe His Ile Asp Pro Asn Asn Gly
705                 710                 715                 720

Asp Glu Ser Ser Asn Lys Val Ala Asn Phe Phe Gln Lys Cys Arg Glu
                725                 730                 735

Asp Pro Glu Tyr Trp Asn Arg Ile Ser Val Gln Gly Leu Asn Arg Ile
            740                 745                 750

Tyr Glu Cys Tyr Thr Trp Lys Ile Tyr Ala Asn Lys Val Leu Asn Met
        755                 760                 765

Gly Ser Ile Tyr Thr Phe Trp Arg Thr Leu Tyr Arg Asp Gln Lys Gln
    770                 775                 780

Ala Lys Gln Arg Tyr Ile Glu Thr Phe Tyr Asn Leu Glu Phe Arg Asn
```

-continued

```
785                 790                 795                 800

Leu Val Lys Asn Val Pro Ile Arg Gln Asp Glu Thr Pro Gln Gly Pro
                805                 810                 815

Lys Glu Arg Arg Glu Lys Val Lys Pro Gln Ile Ser Gln Arg His Ala
            820                 825                 830

Leu Lys Leu Leu Pro Ile Val Phe Gln Glu Thr Leu Val Tyr Ser Ser
        835                 840                 845

Thr Lys Leu Glu Leu Tyr Ser Met Gln Leu Ala Ser Ala Val His Leu
    850                 855                 860

Ser Lys Ser Pro Val Met Ser Ile Lys Leu Thr Lys Ser Ile Asn Ser
865                 870                 875                 880

Ala Phe Pro Phe Pro Met Leu Asp Cys Tyr Tyr Ser Tyr Phe Val Tyr
                885                 890                 895

Gly Ser Leu Pro Ser Leu Phe Ser Pro Val Leu Leu Leu Leu Gln Leu
            900                 905                 910

Tyr
```

MODULATING REDUCING SUGAR CONTENT IN A PLANT

This application is a U.S. National Stage Application of International Application No. PCT/EP2019/057703 filed Mar. 27, 2019, which was published in English on Oct. 3, 2019, as International Publication No. WO 2019/185699 A1. International Application No. PCT/EP2019/057703 claims priority to European Application No. 18164769.4 filed Mar. 28, 2018.

FIELD OF THE INVENTION

The present invention discloses the polynucleotide sequences of genes encoding sucrose synthase (SUS) from *Nicotiana tabacum* and variants, homologues and fragments thereof. The polypeptide sequences encoded thereby and variants, homologues and fragments thereof are also disclosed. The modulation of the expression of the one or more NtSUS genes or the function or activity of the NtSUS polypeptide(s) encoded thereby to modulate the level of reducing sugars in a plant or part thereof is also disclosed.

BACKGROUND

There is a continuing need in the art to produce tobacco material in which the release of flavor compounds in aerosol and smoke is altered. There is also a continuing need in the art to produce tobacco material in which the release of acrylamide in aerosol and smoke is altered.

The present invention seeks to address these and other needs.

SUMMARY OF THE INVENTION

Sucrose synthase (SUS) is a key enzyme involved in sucrose synthesis and a key enzyme in driving the accumulation of reducing sugars—such as glucose, fructose, lactose and maltose—in cured tobacco leaves. By modulating the expression of SUS it is possible to modulate the pool of reducing sugars during and after curing of tobacco leaf. Altered content of reducing sugar in cured tobacco can result in a different perception of the tobacco flavor obtained upon heating. As described herein, certain NtSUS genes are over-expressed during curing whereas others are not and will not contribute to modulating levels of reducing sugars. However, these genes are likely to be involved in other metabolic pathways and changes in their expression could result in a phenotype that is detrimental agronomically (for example, slow growth).

Knowing which NtSUS genes are over-expressed during curing advantageously allows for the selection of plants with changes in only the relevant genes and reduces potential negative effects on other metabolic processes.

Several SUS genomic polynucleotide sequences from *Nicotiana tabacum* are described herein, including NtSUS1-S(SEQ ID NO: 1), NtSUS1-T (SEQ ID NO: 3), NtSUS2-S (SEQ ID NO: 5), NtSUS2-T (SEQ ID NO: 7), NtSUS3-S (SEQ ID NO: 9), NtSUS3-T (SEQ ID NO: 11), NtSUS4-S (SEQ ID NO: 13), NtSUS4-T (SEQ ID NO: 15), NtSUS5-S(SEQ ID NO: 17), NtSUS5-T (SEQ ID NO: 19), NtSUS6-S(SEQ ID NO: 21) and NtSUS6-T (SEQ ID NO: 23). The corresponding deduced polypeptide sequences for NtSUS1-S(SEQ ID NO: 2), NtSUS1-T (SEQ ID NO: 4), NtSUS2-S (SEQ ID NO: 6), NtSUS2-T (SEQ ID NO: 8), NtSUS3-S (SEQ ID NO: 10), NtSUS3-T (SEQ ID NO: 12), NtSUS4-S(SEQ ID NO: 14), NtSUS4-T (SEQ ID NO: 16), NtSUS5-S(SEQ ID NO: 18), NtSUS5-T (SEQ ID NO: 20), NtSUS6-S(SEQ ID NO: 22) and NtSUS6-T (SEQ ID NO: 24) are also disclosed. NtSUS2-S, NtSUS2-T, NtSUS3-S, NtSUS3-T, NtSUS4-S and NtSUS4-T may play a role in sugar metabolism during curing. NtSUS2-S, NtSUS3-S, NtSUS3-T and NtSUS4-S, in particular, are shown to play a role in sugar metabolism during curing. During tobacco curing, flue-cured tobacco usually contains at least eight times more reducing sugars than air-cured tobacco which is principally due to high accumulation of starch in Virginia tobacco. However after plant harvest and during the senescence process a large part of starch is converted first into sucrose and then into reducing sugars likely involving SUS, as well as invertases, as a key enzyme for sucrose metabolism. The present disclosure is therefore particularly useful in modulating reducing sugar content in cured plant material.

In one aspect, there is described a plant cell comprising: (i) a polynucleotide comprising, consisting or consisting essentially of a sequence having at least 95% sequence identity to SEQ ID NO: 1 or SEQ ID NO: 3 or SEQ ID NO: 9 or SEQ ID NO: 11 or SEQ ID NO: 17 or SEQ ID NO: 19 or SEQ ID NO: 21 or SEQ ID NO: 23; or a polynucleotide comprising, consisting or consisting essentially of a sequence having at least 80% sequence identity to SEQ ID NO: 5 or SEQ ID NO: 7 or SEQ ID NO: 13 or SEQ ID NO: 15; (ii) a polypeptide encoded by the polynucleotide set forth in (i); (iii) a polypeptide comprising, consisting or consisting essentially of a sequence having at least 94% sequence identity to SEQ ID NO: 2; or at least 93% sequence identity to SEQ ID NO: 4; or least 95% sequence identity to SEQ ID NO: 6; or at least 96% sequence identity to SEQ ID NO: 8; or at least 93% sequence identity to SEQ ID NO: 10 or SEQ ID NO: 12; or at least 95% sequence identity to SEQ ID NO: 14; or at least 96% sequence identity to SEQ ID NO: 16; or at least 89% sequence identity to SEQ ID NO: 18; or at least 92% sequence identity to SEQ ID NO: 20; or at least 93% sequence identity to SEQ ID NO: 22; or at least 94% sequence identity to SEQ ID NO: 24; or (iv) a construct, vector or expression vector comprising the isolated polynucleotide set forth in (i), wherein said plant cell comprises at least one modification which modulates the expression or activity of the polynucleotide or the polypeptide as compared to a control plant cell in which the expression or activity of the polynucleotide or polypeptide has not been modified.

There is also described a polypeptide comprising, consisting or consisting essentially of a sequence having at least 69% sequence identity to SEQ ID NO: 2 or SEQ ID NO: 4; or least 80% sequence identity to SEQ ID NO: 6 or SEQ ID NO: 8; or at least 74% sequence identity to SEQ ID NO: 10 or SEQ ID NO: 12; or at least 76% sequence identity to SEQ ID NO: 14 or SEQ ID NO: 16; or at least 68% sequence identity to SEQ ID NO: 18 or SEQ ID NO: 20; or at least 69% sequence identity to SEQ ID NO: 22 or SEQ ID NO: 24.

Suitably, said plant cell comprises a polynucleotide comprising, consisting or consisting essentially of a sequence having at least 80% sequence identity to SEQ ID NO:5 or SEQ ID NO: 13 or at least 95% sequence identity to SEQ ID NO: 9 or SEQ ID NO: 11.

Suitably, said plant cell comprises a polypeptide comprising, consisting or consisting essentially of a sequence having at least 81% sequence identity to SEQ ID NO: 6, or at least 72% sequence identity to SEQ ID NO: 10 or SEQ ID NO: 12 or at least 80% sequence identity to SEQ ID NO: 14.

Suitably, said plant cell comprises a polypeptide comprising, consisting or consisting essentially of a sequence having at least 80% sequence identity to SEQ ID NO: 6, or at least 74% sequence identity to SEQ ID NO: 10 or SEQ ID NO: 12 or at least 76% sequence identity to SEQ ID NO: 14.

Suitably, the at least one modification is a modification of the plant cell's genome, or a modification of the construct, vector or expression vector, or a transgenic modification.

Suitably, the modification of the plant cell's genome, or the modification of the construct, vector, or expression vector is a mutation or edit.

Suitably, the modification increases or decreases the expression or activity of the polynucleotide or the polypeptide as compared to the control plant cell.

Suitably, the plant cell comprises an interference polynucleotide comprising a sequence that is at least 80% complementary to at least 19 nucleotides of an RNA transcribed from the polynucleotide of claim 1(i).

Suitably, the modulated expression or activity of the polynucleotide or the polypeptide modulates the level of reducing sugars in leaf derived from the plant cell as compared to the level of reducing sugar in leaf derived from a control plant, suitably wherein the reducing sugar is glucose or fructose or suitably, wherein the leaf is early cured or cured leaf.

In another aspect, there is described a plant or part thereof comprising the plant cell as described herein.

In another aspect, there is described plant material, cured plant material, or homogenized plant material, derived from the plant or part thereof as described herein.

Suitably, the plant material comprises biomass, seed, stem, flowers, or leaves from the plant or part thereof as described herein.

Suitably, the cured plant material is flue-cured, sun-cured or air-cured plant material.

In another aspect, there is described a tobacco product comprising the plant cell as described herein, a part of the plant as described herein or the plant material as described herein.

In another aspect, there is described a method for producing the plant as described herein, comprising the steps of: (a) providing a plant cell comprising a polynucleotide comprising, consisting or consisting essentially of a sequence having at least 95% sequence identity to SEQ ID NO: 1 or SEQ ID NO: 3 or SEQ ID NO: 9 or SEQ ID NO: 11 or SEQ ID NO: 17 or SEQ ID NO: 19 or SEQ ID NO: 21 or SEQ ID NO: 23; or having at least 80% sequence identity to SEQ ID NO: 5 or SEQ ID NO: 7 or SEQ ID NO: 13 or SEQ ID NO: 15; (b) modifying the plant cell to modulate the expression of said polynucleotide as compared to a control plant cell; and (c) propagating the plant cell into a plant.

Suitably, step (c) comprises cultivating the plant from a cutting or seedling comprising the plant cell.

Suitably, the step of modifying the plant cell comprises modifying the genome of the cell by genome editing or genome engineering.

Suitably, the genome editing or genome engineering is selected from CRISPR/Cas technology, zinc finger nuclease-mediated mutagenesis, chemical or radiation mutagenesis, homologous recombination, oligonucleotide-directed mutagenesis and meganuclease-mediated mutagenesis.

Suitably, the step of modifying the plant cell comprises transfecting the cell with a construct comprising a polynucleotide comprising, consisting or consisting essentially of a sequence having at least 95% sequence identity to SEQ ID NO: 1 or SEQ ID NO: 3 or SEQ ID NO: 9 or SEQ ID NO: 11 or SEQ ID NO: 17 or SEQ ID NO: 19 or SEQ ID NO: 21 or SEQ ID NO: 23; or having at least 80% sequence identity to SEQ ID NO: 5 or SEQ ID NO: 7 or SEQ ID NO: 13 or SEQ ID NO: 15 operably linked to a constitutive promoter.

Suitably, the step of modifying the plant cell comprises introducing an interference polynucleotide comprising a sequence that is at least 80% complementary to an RNA transcribed from the polynucleotide of claim 1(i) into the cell.

Suitably, the plant cell is transfected with a construct expressing an interference polynucleotide comprising a sequence that is at least 80% complementary to at least 19 nucleotides of an RNA transcribed from the polynucleotide as described herein.

In another aspect, there is described a method for producing cured plant material with an altered amount of reducing sugars as compared to control plant material, comprising the steps of: (a) providing a plant or part thereof or the plant material as described herein; (b) harvesting the plant material therefrom; and (c) curing the plant material.

Suitably, the plant material comprises cured leaves, cured stems or cured flowers, or a mixture thereof.

Suitably, the curing method is selected from the group consisting of air curing, fire curing, smoke curing, and flue curing.

Some Advantages

Advantageously, the NtSUS polynucleotide sequences described herein are expressed during curing, particularly from the onset of curing. Modulating the expression of one or more NtSUS polynucleotide sequences can result in modulated levels of reducing sugars—such as glucose and fructose—in cured tobacco leaves. In particular, increasing or decreasing the expression of one or more NtSUS polynucleotides can result in increased or decreased levels of reducing sugars and a different perception of the tobacco obtained therefrom upon heating.

In cigarette smoke, reducing sugars impact the release of carbonyl components like formaldehyde, acetaldehyde, acetone, 2-furfural and acrolein (see The Chemical Components of Tobacco and Tobacco Smoke, 2$^{nd}$ Edition, Rodgman and Perfetti, 2016). Altering reducing sugar content may therefore change the release of such carbonyl compounds. Regarding aroma release in aerosol and smoke, glucose and to a lesser extent fructose may generate Amadori compounds via Maillard reaction when interacting with amino acids upon heating. Although the free amino acids are considered as the limiting factors in this chemical reaction, the presence of reducing sugars is necessary to allow the formation of Amadori compounds. Bread, nutty or popcorn-like flavor results from heating proline and glucose thus generating 2-acetyl-1-pyrroline like products. As proline and reducing sugars are particularly abundant in flue-cured tobacco, nutty notes are obtained when heating or smoking Virginia tobacco. In a blend, acrylamide (a carcinogenic compound resulting from the interaction of glucose (fructose) with asparagine upon heating) may typically result from a combination of Burley (high in asparagine) with Virginia (high in reducing sugars) tobacco. Therefore, modifying the reducing sugar versus amino acid balance may impact the release of both flavour compounds and acrylamide in aerosol and smoke.

Advantageously, recombined tobacco material of heated tobacco often requires reducing sugars for proper Cast Leaf preparation. Modulating the expression of SUS genes during leaf curing may impact the content and the balance of the reducing sugars thereby affecting Cast Leaf preparation.

Advantageously, non-genetically modified plants can be created which may be more acceptable to consumers.

Advantageously, the present disclosure is not restricted to the use of EMS mutant plants. An EMS mutant plant can have less potential to bring improved properties to a crop after breeding. Once breeding is started, the desirable characteristic(s) of the EMS mutant plant can be lost for different reasons. For example, several mutations may be required, the mutation can be dominant or recessive, and the identification of a point mutation in a gene target can be difficult to reach. In contrast, the present disclosure exploits the use of NtAAT polynucleotides that can be specifically manipulated to produce plants with a desirable phenotype. The disclosure may be applied to various plant varieties or crops.

BRIEF DESCRIPTION OF THE DRAWINGS

FIG. 1 is a bar graph showing the content per variety of reducing sugars after harvest (ripe), after two days of curing (48 hours curing) and at the end of curing.

DETAILED DESCRIPTION

Section headings as used in this disclosure are for organisation purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures.

The singular forms "a," "and" and "the" include plural references unless the context clearly dictates otherwise.

The term "and/or" means (a) or (b) or both (a) and (b).

The present disclosure contemplates other embodiments "comprising," "consisting of" and "consisting essentially of" the embodiments or elements presented herein, whether explicitly set forth or not.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used throughout the specification and the claims, the following terms have the following meanings:

"Coding sequence" or "polynucleotide encoding" means the nucleotides (RNA or DNA molecule) that comprise a polynucleotide which encodes a polypeptide. The coding sequence can further include initiation and termination signals operably linked to regulatory elements including a promoter and polyadenylation signal capable of directing expression in the cells of an individual or mammal to which the polynucleotide is administered. The coding sequence may be codon optimized.

"Complement" or "complementary" can mean Watson-Crick (for example, A-T/U and C-G) or Hoogsteen base pairing between nucleotides or nucleotide analogs. "Complementarity" refers to a property shared between two polynucleotides, such that when they are aligned antiparallel to each other, the nucleotide bases at each position will be complementary.

"Construct" refers to a double-stranded, recombinant polynucleotide fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "control" in the context of a control plant or control plant cells means a plant or plant cells in which the expression, function or activity of one or more genes or polypeptides has not been modified (for example, increased or decreased) and so it can provide a comparison with a plant in which the expression, function or activity of the same one or more genes or polypeptides has been modified. As used herein, a "control plant" is a plant that is substantially equivalent to a test plant or modified plant in all parameters with the exception of the test parameters. For example, when referring to a plant into which a polynucleotide has been introduced, a control plant is an equivalent plant into which no such polynucleotide has been introduced. A control plant can be an equivalent plant into which a control polynucleotide has been introduced. In such instances, the control polynucleotide is one that is expected to result in little or no phenotypic effect on the plant. The control plant may comprise an empty vector. The control plant may correspond to a wild-type plant. The control plant may be a null segregant wherein the T1 segregant no longer possesses the transgene.

"Donor DNA" or "donor template" refers to a double-stranded DNA fragment or molecule that includes at least a portion of the gene of interest. The donor DNA may encode a fully-functional polypeptide or a partially-functional polypeptide.

"Endogenous gene or polypeptide" refers to a gene or polypeptide that originates from the genome of an organism and has not undergone a change, such as a loss, gain, or exchange of genetic material. An endogenous gene undergoes normal gene transmission and gene expression. An endogenous polypeptide undergoes normal expression.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms including increasing transcriptional efficiency, stabilization of mature mRNA and translational enhancement.

"Expression" refers to the production of a functional product. For example, expression of a polynucleotide fragment may refer to transcription of the polynucleotide fragment (for example, transcription resulting in mRNA or functional RNA) and/or translation of mRNA into a precursor or mature polypeptide. "Overexpression" refers to the production of a gene product in transgenic organisms that exceeds levels of production in a null segregating (or non-transgenic) organism from the same experiment.

"Functional" and "full-functional" describes a polypeptide that has biological function or activity. A "functional gene" refers to a gene transcribed to mRNA, which is translated to a functional or active polypeptide.

"Genetic construct" refers to DNA or RNA molecules that comprise a polynucleotide that encodes a polypeptide. The coding sequence can include initiation and termination signals operably linked to regulatory elements including a promoter and polyadenylation signal capable of directing expression.

"Genome editing" refers to changing an endogenous gene that encodes an endogenous polypeptide, such that polypeptide expression of a truncated endogenous polypeptide or an endogenous polypeptide having an amino acid substitution is obtained. Genome editing can include replacing the region of the endogenous gene to be targeted or replacing the entire endogenous gene with a copy of the gene that has a truncation or an amino acid substitution with a repair mechanism—such as HDR. Genome editing may also include generating an amino acid substitution in the endogenous gene by generating a double stranded break in the endogenous gene that is then repaired using NHEJ. NHEJ may add or delete at least one base pair during repair which may generate an amino acid substitution. Genome editing may also include deleting a gene segment by the simultaneous action of two nucleases on the same DNA strand in order to create a truncation between the two nuclease target sites and repairing the DNA break by NHEJ.

"Heterologous" with respect to a sequence means a sequence that originates from a foreign species, or, if from the same species, is substantially modified from its native form in composition and/or genomic locus by deliberate human intervention.

"Homology-directed repair" or "HDR" refers to a mechanism in cells to repair double strand DNA lesions when a homologous piece of DNA is present in the nucleus, mostly in G2 and S phase of the cell cycle. HDR uses a donor DNA or donor template to guide repair and may be used to create specific sequence changes to the genome, including the targeted addition of whole genes. If a donor template is provided along with the site specific nuclease, then the cellular machinery will repair the break by homologous recombination, which is enhanced several orders of magnitude in the presence of DNA cleavage. When the homologous DNA piece is absent, NHEJ may take place instead.

The terms "homology" or "similarity" refer to the degree of sequence similarity between two polypeptides or between two polynucleotide molecules compared by sequence alignment. The degree of homology between two discrete polynucleotides being compared is a function of the number of identical, or matching, nucleotides at comparable positions.

"Identical" or "identity" in the context of two or more polynucleotides or polypeptides means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be determined manually or by using a computer sequence algorithm such as ClustalW, ClustalX, BLAST, FASTA or Smith-Waterman. The popular multiple alignment program ClustalW (*Nucleic Acids Research* (1994) 22, 4673-4680; *Nucleic Acids Research* (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

The term "increase" or "increased" refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or a function or an activity, such as but not limited to polypeptide function or activity, transcriptional function or activity, and/or polypeptide expression. The term "increased," or the phrase "an increased amount" can refer to a quantity or a function or an activity in a modified plant or a product generated from the modified plant that is more than what would be found in a plant or a product from the same variety of plant processed in the same manner, which has not been modified. Thus, in some contexts, a wild-type plant of the same variety that has been processed in the same manner is used as a control by which to measure whether an increase in quantity is obtained.

The term "increase" or "increased" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or, or at least 150%, or at least 200% more of a quantity or a function—such as polypeptide function, transcriptional function, or polypeptide expression. The term "increased," or the phrase "an increased amount" can refer to a quantity or a function in a modified plant or a product generated from the modified plant that is less than what would be found in a plant or a product from the same variety of plant processed in the same manner, which has not been modified. Thus, in some contexts, a wild-type plant of the same variety that has been processed in the same manner is used as a control by which to measure whether a reduction in quantity is obtained.

The term "inhibit" or "inhibited" refers to a reduction of from about 98% to about 100%, or a reduction of at least 98%, at least 99%, but particularly of 100%, of a quantity or a function or an activity, such as but not limited to polypeptide function or activity, transcriptional function or activity, and/or polypeptide expression.

The term "introduced" means providing a polynucleotide (for example, a construct) or polypeptide into a cell. Introduced includes reference to the incorporation of a polynucleotide into a eukaryotic cell where the polynucleotide may be incorporated into the genome of the cell, and includes reference to the transient provision of a polynucleotide or polypeptide to the cell. Introduced includes reference to stable or transient transformation methods, as well as sexually crossing. Thus, "introduced" in the context of inserting a polynucleotide (for example, a recombinant construct/expression construct) into a cell, means "transfection" or "transformation" or "transduction" and includes reference to the incorporation of a polynucleotide into a eukaryotic cell where the polynucleotide may be incorporated into the genome of the cell (for example, chromosome, plasmid, plastid or mitochondrial DNA), converted into an autonomous replicon, or transiently expressed (for example, transfected mRNA).

The terms "isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. A polypeptide that is the predominant species present in a preparation is substantially purified. In particular, an isolated polynucleotide is separated from open reading frames that flank the desired gene and encode polypeptides other than the desired polypeptide. The term "purified" as used herein denotes that a polynucleotide or polypeptide gives rise to essentially one band in an electrophoretic gel. Particularly, it means that the polynucleotide or polypeptide is at least 85% pure, more preferably at least 95% pure, and most preferably at least 99% pure. Isolated polynucleotides may be purified from a host cell in which they naturally occur. Conventional polynucleotide purification methods known to skilled artisans may be used to obtain isolated polynucleotides. The term also embraces recombinant polynucleotides and chemically synthesized polynucleotides.

"Modulate" or "modulating" refers to causing or facilitating a qualitative or quantitative change, alteration, or modification in a process, pathway, function or activity of interest. Without limitation, such a change, alteration, or modification may be an increase or decrease in the relative process, pathway, function or activity of interest. For example, gene expression or polypeptide expression or polypeptide function or activity can be modulated. Typically, the relative change, alteration, or modification will be determined by comparison to a control.

"Non-homologous end joining (NHEJ) pathway" as used herein refers to a pathway that repairs double-strand breaks in DNA by directly ligating the break ends without the need for a homologous template. The template-independent religation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

The term 'non-naturally occurring' describes an entity—such as a polynucleotide, a genetic mutation, a polypeptide, a plant, a plant cell and plant material—that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. In certain embodiments, a mutation is not a naturally occurring mutation that exists naturally in a polynucleotide or a polypeptide—such as a gene or a polypeptide. Differences in genetic background can be detected by phenotypic differences or by molecular biology techniques known in the art—such as polynucleotide sequencing, presence or absence of genetic markers (for example, microsatellite RNA markers).

"Oligonucleotide" or "polynucleotide" means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a given sequence under stringent hybridization conditions. Thus, a polynucleotide also encompasses a probe that hybridizes under stringent hybridization conditions. Polynucleotides may be single stranded or double stranded, or may contain portions of both double stranded and single stranded sequence. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Polynucleotides may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). Hybridization stringency increases as the propensity to form DNA duplexes decreases. In polynucleotide hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments. DNA duplexes are stabilised by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions. To hybridize under "stringent conditions" describes hybridization protocols in which polynucleotides at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the given sequence hybridize to the given sequence at equilibrium. Since the given sequences are generally present at excess, at Tm, 50% of the probes are occupied at equilibrium.

"Stringent hybridization conditions" are conditions that enable a probe, primer, or oligonucleotide to hybridize only to its specific sequence. Stringent conditions are sequence-dependent and will differ. Stringent conditions typically comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, for example, 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Suitably, the conditions are such that sequences at least about 65%, 70%, 75%, 85%, 90%, 95%, 98%, or 99% homologous to each other typically remain hybridized to each other.

"Moderately stringent conditions" use washing solutions and hybridization conditions that are less stringent, such that a polynucleotide will hybridize to the entire, fragments, derivatives, or analogs of the polynucleotide. One example comprises hybridization in 6×SSC, 5×Denhardt's solution, 0.5% SDS and 100 μg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (see Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)). "Low stringent conditions" use washing solutions and hybridization conditions that are less stringent than those for moderate stringency, such that a polynucleotide will hybridize to the entire, fragments, derivatives, or analogs of the polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 μg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (see Ausubel et al., 1993; Kriegler, 1990).

"Operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. "Operably linked" refers to the association of polynucleotide fragments in a single fragment so that the function of one is regulated by the other. For example, a promoter is operably linked with a polynucleotide fragment when it is capable of regulating the transcription of that polynucleotide fragment.

The term "plant" refers to any plant at any stage of its life cycle or development, and its progenies. In one embodiment, the plant is a tobacco plant, which refers to a plant belonging to the genus *Nicotiana*. The term includes reference to whole plants, plant organs, plant tissues, plant propagules, plant seeds, plant cells and progeny of same. Plant cells include, without limitation, cells from seeds, suspension cultures, embryos, meristematic regions, callus tissue, leaves, roots, shoots, gametophytes, sporophytes, pollen, and microspores. Suitable species, cultivars, hybrids and varieties of tobacco plant are described herein.

"Polynucleotide", "polynucleotide sequence" or "polynucleotide fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. A polynucleotide can be, without limitation, a genomic DNA, complementary DNA (cDNA), mRNA, or antisense RNA or a fragment(s) thereof. Moreover, a polynucleotide can be single-stranded or double-stranded, a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid (PNA). Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, the polynucleotides include their corresponding RNA sequences, and their complementary (for example, completely complementary) DNA or RNA sequences, including the reverse complements thereof. The polynucleotides of the present disclosure are set forth in the accompanying sequence listing.

"Polypeptide" or "polypeptide sequence" refer to a polymer of amino acids in which one or more amino acid residues is an artificial chemical analogue of a corresponding naturally occurring amino acid, as well as to naturally occurring polymers of amino acids. The terms are also inclusive of modifications including, but not limited to, glycosylation, lipid attachment, sulfation, gamma-carboxylation of glutamic acid residues, hydroxylation and ADP-ribosylation. The polypeptides of the present disclosure are set forth in the accompanying sequence listing.

"Promoter" means a synthetic or naturally-derived molecule which is capable of conferring, activating or enhancing expression of a polynucleotide in a cell. The term refers to a polynucleotide element/sequence, typically positioned upstream and operably-linked to a double-stranded polynucleotide fragment. Promoters can be derived entirely from regions proximate to a native gene of interest, or can be composed of different elements derived from different native promoters or synthetic polynucleotide segments. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents.

"Tissue-specific promoter" and "tissue-preferred promoter" as used interchangeably herein refer to a promoter that is expressed predominantly but not necessarily exclusively in one tissue or organ, but that may also be expressed in one specific cell. A "developmentally regulated promoter" refers to a promoter whose function is determined by developmental events. A "constitutive promoter" refers to a promoter that causes a gene to be expressed in most cell types at most times. An "inducible promoter" selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include promoters regulated by light, heat, stress, flooding or drought, pathogens, phytohormones, wounding, or chemicals such as ethanol, jasmonate, salicylic acid, or safeners.

"Recombinant" as used herein refers to an artificial combination of two otherwise separated segments of sequence—such as by chemical synthesis or by the manipulation of isolated segments of polynucleotides by genetic engineering techniques. The term also includes reference to a cell or vector, that has been modified by the introduction of a heterologous polynucleotide or a cell derived from a cell so modified, but does not encompass the alteration of the cell or vector by naturally occurring events (for example, spontaneous mutation, natural transformation or transduction or transposition) such as those occurring without deliberate human intervention.

"Recombinant construct" refers to a combination of polynucleotides that are not normally found together in nature. Accordingly, a recombinant construct may comprise regulatory sequences and coding sequences that are derived from different sources, or regulatory sequences and coding sequences derived from the same source, but arranged in a manner different than that normally found in nature. The recombinant construct can be a recombinant DNA construct.

"Regulatory sequences" and "regulatory elements" as used interchangeably herein refer to polynucleotide sequences located upstream (5' non-coding sequences), within, or downstream (3' non-coding sequences) of a coding sequence, and which influence the transcription, RNA processing or stability, or translation of the associated coding sequence. Regulatory sequences include promoters, translation leader sequences, introns, and polyadenylation recognition sequences. The terms "regulatory sequence" and "regulatory element" are used interchangeably herein.

"Site-specific nuclease" refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), CRISPR/Cas9-based systems, and meganucleases.

The term "tobacco" is used in a collective sense to refer to tobacco crops (for example, a plurality of tobacco plants grown in the field and not hydroponically grown tobacco), tobacco plants and parts thereof, including but not limited to, roots, stems, leaves, flowers, and seeds prepared and/or obtained, as described herein. It is understood that "tobacco" includes *Nicotiana tabacum* plants and products thereof.

The term "tobacco products" refers to consumer tobacco products, including but not limited to, smoking materials (for example, cigarettes, cigars, and pipe tobacco), snuff, chewing tobacco, gum, and lozenges, as well as components, materials and ingredients for manufacture of consumer tobacco products. Suitably, these tobacco products are manufactured from tobacco leaves and stems harvested from tobacco and cut, dried, cured, and/or fermented according to conventional techniques in tobacco preparation.

"Transcription terminator", "termination sequences", or "terminator" refers to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Transgenic" refers to any cell, cell line, callus, tissue, plant part or plant, the genome of which has been altered by the presence of a heterologous polynucleotide, such as a recombinant construct, including those initial transgenic events as well as those created by sexual crosses or asexual propagation from the initial transgenic event. The term does not encompass the alteration of the genome (chromosomal or extra-chromosomal) by conventional plant breeding methods or by naturally occurring events—such as random cross-fertilization, non-recombinant viral infection, non-recombinant bacterial transformation, non-recombinant transposition, or spontaneous mutation.

"Transgenic plant" refers to a plant which comprises within its genome one or more heterologous polynucleotides, that is, a plant that contains recombinant genetic material not normally found therein and which has been introduced into the plant in question (or into progenitors of the plant) by human manipulation. For example, the heterologous polynucleotide can be stably integrated within the genome such that the polynucleotide is passed on to successive generations. The heterologous polynucleotide can be integrated into the genome alone or as part of a recombinant construct. The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems and the like. Each heterologous polynucleotide may confer a different trait to the transgenic plant.

"Transcription activator-like effector" or "TALE" refers to a polypeptide structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence. A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion polypeptides of the catalytic domain of a nuclease, such as endonuclease FokI, and a designed TALE DNA-binding domain that may be targeted to a custom DNA sequence.

A "TALEN monomer" refers to an engineered fusion polypeptide with a catalytic nuclease domain and a designed TALE DNA-binding domain. Two TALEN monomers may be designed to target and cleave a TALEN target region.

"Transgene" refers to a gene or genetic material containing a gene sequence that has been isolated from one organism and is introduced into a different organism. This non-native segment of DNA may retain the ability to produce RNA or polypeptide in the transgenic organism, or it may alter the normal function of the transgenic organism's genetic code. The introduction of a transgene has the potential to change the phenotype of an organism.

"Variant" with respect to a polynucleotide means: (i) a portion or fragment of a polynucleotide; (ii) the complement of a polynucleotide or portion thereof; (iii) a polynucleotide that is substantially identical to a polynucleotide of interest or the complement thereof; or (iv) a polynucleotide that hybridizes under stringent conditions to the polynucleotide of interest, complement thereof, or a polynucleotide substantially identical thereto.

"Variant" with respect to a peptide or polypeptide means a peptide or polypeptide that differs in sequence by the insertion, deletion, or conservative substitution of amino acids, but retain at least one biological function or activity. Variant may also mean a polypeptide that retains at least one biological function or activity. A conservative substitution of an amino acid, that is, replacing an amino acid with a different amino acid of similar properties (for example, hydrophilicity, degree and distribution of charged regions) is recognized in the art as typically involving a minor change.

The term "variety" refers to a population of plants that share constant characteristics which separate them from other plants of the same species. While possessing one or more distinctive traits, a variety is further characterized by a very small overall variation between individuals within that variety. A variety is often sold commercially.

"Vector" refers to a polynucleotide vehicle that comprises a combination of polynucleotide components for enabling the transport of polynucleotides, polynucleotide constructs and polynucleotide conjugates and the like. A vector may be a viral vector, bacteriophage, bacterial artificial chromosome or yeast artificial chromosome. A vector may be a DNA or RNA vector. Suitable vectors include episomes capable of extra-chromosomal replication such as circular, double-stranded nucleotide plasmids; linearized double-stranded nucleotide plasmids; and other vectors of any origin. An "expression vector" as used herein is a polynucleotide vehicle that comprises a combination of polynucleotide components for enabling the expression of polynucleotide(s), polynucleotide constructs and polynucleotide conjugates and the like. Suitable expression vectors include episomes capable of extra-chromosomal replication such as circular, double-stranded nucleotide plasmids; linearized double-stranded nucleotide plasmids; and other functionally equivalent expression vectors of any origin. An expression vector comprises at least a promoter positioned upstream and operably-linked to a polynucleotide, polynucleotide constructs or polynucleotide conjugate, as defined below.

"Zinc finger" refers to a polypeptide structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

"Zinc finger nuclease" or "ZFN" refers to a chimeric polypeptide molecule comprising at least one zinc finger DNA binding domain effectively linked to at least one nuclease or part of a nuclease capable of cleaving DNA when fully assembled.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and polypeptide and polynucleotide chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Polynucleotides

In one embodiment, there is provided an isolated polynucleotide comprising, consisting or consisting essentially of a sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

Suitably, the polynucleotide(s) described herein encode an active polypeptide that has at least about 50%, 60%, 70%, 80%, 90%, 95%, 96%, 97%, 98%, 99%, 100% or more of the function or activity of the polypeptide(s) shown in the sequence listing.

In another embodiment, there is provided an isolated polynucleotide comprising, consisting or consisting essentially of a polynucleotide having at least 60% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 or to SEQ ID NO:5, SEQ ID NO: 9, SEQ ID NO: 11 or SEQ ID NO: 13.

Suitably, the isolated polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 or to SEQ ID NO:5, SEQ ID NO: 9, SEQ ID NO: 11 or SEQ ID NO: 13.

Suitably, the isolated polynucleotide comprises, consists or consist essentially of a sequence having at least about 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 or to SEQ ID NO:5, SEQ ID NO: 9, SEQ ID NO: 11 or SEQ ID NO: 13.

Suitably, the isolated polynucleotide comprises, consists or consist essentially of a sequence having at least about 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 5, SEQ ID NO: 7, SEQ ID NO: 13 or SEQ ID NO: 15.

Suitably, the isolated polynucleotide comprises, consists or consist essentially of a sequence having at least about 95%, 96%, 97%, 98%, 99%, 99.1%, 99.2%, 99.3%, 99.4%, 99.5%, 99.6%, 99.7%, 99.8%, 99.9% or 100% sequence identity to SEQ ID NO: 1, SEQ ID NO: 3, SEQ ID NO: 9, SEQ ID NO: 11, SEQ ID NO: 17, SEQ ID NO: 19, SEQ ID NO: 21 or SEQ ID NO: 23.

In another embodiment, there is provided polynucleotides comprising, consisting or consisting essentially of polynucleotides with substantial homology (that is, sequence similarity) or substantial identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 or to SEQ ID NO:5, SEQ ID NO: 9, SEQ ID NO: 11 or SEQ ID NO: 13.

In another embodiment, there is provided fragments of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23.

In another embodiment, there is provided fragments of SEQ ID NO:5, SEQ ID NO: 9, SEQ ID NO: 11 or SEQ ID NO: 13 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:5, SEQ ID NO: 9, SEQ ID NO: 11 or SEQ ID NO: 13.

In another embodiment, there is provided polynucleotides comprising a sufficient or substantial degree of identity or similarity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 or to SEQ ID NO:5, SEQ ID NO: 9, SEQ ID NO: 11 or SEQ ID NO: 13 that encode a polypeptide that functions as a SUS.

In another embodiment, there is provided a polymer of polynucleotides which comprises, consists or consists essentially of a polynucleotide designated herein as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23 or to SEQ ID NO:5, SEQ ID NO: 9, SEQ ID NO: 11 or SEQ ID NO: 13.

Suitably, the polynucleotides described herein encode members of the SUS family.

A polynucleotide as described herein can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, they include their corresponding RNA sequences, and their complementary (for example, completely complementary) DNA or RNA sequences, including the reverse complements thereof.

A polynucleotide as described herein will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in hybridisation assays or primers for use in amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide comprising the use of the probes or primers or both. Exemplary primers are described herein.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the polypeptide sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries include cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under decreased stringency conditions, typically moderately stringent conditions, and commonly highly stringent conditions to the polynucleotide(s), as described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y. and can be readily determined by those having ordinary skill in the art based on, for example, the length or base composition of the polynucleotide.

One way of achieving moderately and high stringent conditions are defined herein. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N. Y). When hybridizing a polynucleotide to a polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (C)=81.5+16.6 (log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a first sequence is positioned in the 5'-to-3' direction, and if a second sequence is positioned in the 5'-to-3' direction within the same polynucleotide molecule/strand, then the first sequence and the second sequence are orientated in the same direction, or have the same orientation. Typically, a promoter sequence and a gene of interest under the regulation of the given promoter are positioned in the same orientation.

However, with respect to the first sequence positioned in the 5'-to-3' direction, if a second sequence is positioned in the 3'-to-5' direction within the same polynucleotide molecule/strand, then the first sequence and the second sequence are orientated in anti-sense direction, or have anti-sense orientation. Two sequences having anti-sense orientations with respect to each other can be alternatively described as having the same orientation, if the first sequence (5'-to-3' direction) and the reverse complementary sequence of the first sequence (first sequence positioned in the 5'-to-3') are positioned within the same polynucleotide molecule/strand. The sequences set forth herein are shown in the 5'-to-3' direction.

At least one modification (for example, mutation) can be included in one or more of NtSUS1-S, NtSUS1-T, NtSUS2-S, NtSUS2-T, NtSUS3-S, NtSUS3-T, NtSUS4-S, NtSUS4-T, NtSUS5-S, NtSUS5-T, NtSUS6-S and NtSUS6-T. At least one modification (for example, mutation) can be included in one or more of NtSUS2-S, NtSUS2-T, NtSUS3-S, NtSUS3-T, NtSUS4-S and NtSUS4-T.

At least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T is not modulated.

At least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T is not modulated.

3. Polypeptide

In another aspect, there is provided an isolated polypeptide comprising, consisting or consisting essentially of a polypeptide having at least 60% sequence identity to any of the polypeptide described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

In one embodiment, there is provided a polypeptide comprising, consisting or consisting essentially of a sequence having at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2 or SEQ ID NO: 4.

In another embodiment, there is provided a polypeptide comprising, consisting or consisting essentially of a sequence having at least 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2.

In another embodiment, there is provided a polypeptide comprising, consisting or consisting essentially of a sequence having at least 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 4.

In one embodiment, there is provided a polypeptide comprising, consisting or consisting essentially of a sequence having at least 80%, 81%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 6 or SEQ ID NO: 8.

In another embodiment, there is provided a polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 6.

In another embodiment, there is provided a polypeptide comprising, consisting or consisting essentially of a sequence having at least 96%, 97%, 98%, 99%, 99.1%, 99.2%, 99.3%, 99.4%, 99.5%, 99.6%, 99.7%, 99.8%, 99.9% or 100% sequence identity to SEQ ID NO: 8.

In one embodiment, there is provided a polypeptide comprising, consisting or consisting essentially of a sequence having at least 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 10 or SEQ ID NO: 12.

In another embodiment, there is provided a polypeptide comprising, consisting or consisting essentially of a sequence having at least 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 10 or SEQ ID NO: 12.

In one embodiment, there is provided a polypeptide comprising, consisting or consisting essentially of a sequence having at least 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 14 or SEQ ID NO: 16.

In another embodiment, there is provided a polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 14.

In another embodiment, there is provided a polypeptide comprising, consisting or consisting essentially of a sequence having at least 96%, 97%, 98%, 99%, 99.1%, 99.2%, 99.3%, 99.4%, 99.5%, 99.6%, 99.7%, 99.8%, 99.9% or 100% sequence identity to SEQ ID NO: 16.

In one embodiment, there is provided a polypeptide comprising, consisting or consisting essentially of a sequence having at least 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 18 or SEQ ID NO: 20.

In another embodiment, there is provided a polypeptide comprising, consisting or consisting essentially of a sequence having at least 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 18.

In another embodiment, there is provided a polypeptide comprising, consisting or consisting essentially of a sequence having at least 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 20.

In one embodiment, there is provided a polypeptide comprising, consisting or consisting essentially of a sequence having at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 22 or SEQ ID NO: 24.

In another embodiment, there is provided a polypeptide comprising, consisting or consisting essentially of a sequence having at least 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 22.

In another embodiment, there is provided a polypeptide comprising, consisting or consisting essentially of a sequence having at least 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 24.

In one embodiment, there is provided a polypeptide encoded by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23; or SEQ ID NO:5, SEQ ID NO: 9, SEQ ID NO: 11 or SEQ ID NO: 13.

The polypeptide can include sequences comprising a sufficient or substantial degree of identity or similarity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 or SEQ ID NO: 24; or SEQ ID NO: 6, SEQ ID NO: 10, SEQ ID NO: 12 or SEQ ID NO: 14 to function as a SUS.

The fragments of the polypeptide(s) typically retain some or all of the function or activity of the full length sequence.

As discussed herein, the polypeptides also include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still have some or all of their function or activity. Suitably, this function or activity is modulated.

A deletion refers to removal of one or more amino acids from a polypeptide. An insertion refers to one or more amino acid residues being introduced into a predetermined site in a polypeptide.

Insertions may comprise intra-sequence insertions of single or multiple amino acids. A substitution refers to the replacement of amino acids of the polypeptide with other amino acids having similar properties (such as similar hydrophobicity, hydrophilicity, antigenicity, propensity to form or break a-helical structures or β-sheet structures). Amino acid substitutions are typically of single residues, but may be clustered depending upon functional constraints placed upon the polypeptide and may range from about 1 to about 10 amino acids. The amino acid substitutions are preferably conservative amino acid substitutions as described below. Amino acid substitutions, deletions and/or insertions can be made using peptide synthetic techniques—such as solid phase peptide synthesis or by recombinant DNA manipulation. Methods for the manipulation of DNA sequences to produce substitution, insertion or deletion variants of a polypeptide are well known in the art. The variant may have alterations which produce a silent change and result in a functionally equivalent polypeptide. Deliberate amino acid substitutions may be made on the basis of similarity in polarity, charge, solubility, hydrophobicity, hydrophilicity and the amphipathic nature of the residues as long as the secondary binding of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| | | |
|---|---|---|
| ALIPHATIC | Non-polar | Gly Ala Pro |
| | | Ile Leu Val |
| | Polar-uncharged | Cys Ser Thr Met |
| | | Asn Gly |
| | Polar-charged | Asp Glu |
| | | Lys Arg |
| AROMATIC | | His Phe TrpTyr |

The polypeptide may be a mature polypeptide or an immature polypeptide or a polypeptide derived from an immature polypeptide. Polypeptides may be in linear form or cyclized using known methods. Polypeptides typically comprise at least 10, at least 20, at least 30, or at least 40 contiguous amino acids.

At least one modification (for example, mutation) can be included in one or more of NtSUS1-S, NtSUS1-T, NtSUS2-S, NtSUS2-T, NtSUS3-S, NtSUS3-T, NtSUS4-S, NtSUS4-T, NtSUS5-S, NtSUS5-T, NtSUS6-S and NtSUS6-T.

At least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtSUS2-S, NtSUS2-T, NtSUS3-S, NtSUS3-T, NtSUS4-S and NtSUS4-T whereas no modification(s) (for example, mutation(s)) are included in one or more of NtSUS1-S, NtSUS1-T, NtSUS5-S, NtSUS5-T, NtSUS6-S and NtSUS6-T.

At least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T is not modulated.

At least one modification (for example, mutation) can be included in one or more of NtSUS2-S, NtSUS3-S, NtSUS3-T and NtSUS4-S whereas no modification(s) (for example, mutation(s)) are included in one or more of NtSUS1-S, NtSUS1-T, NtSUS2-T, NtSUS4-T, NtSUS5-S, NtSUS5-T, NtSUS6-S and NtSUS6-T is not modulated.

Modifying Plants a. Transformation

Recombinant constructs can be used to transform plants or plant cells in order to modulate polypeptide expression, function or activity. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which polypeptide expression, function or activity are modulated can include mutant, non-naturally occurring, transgenic, man-made or genetically engineered plants or plant cells. Suitably, the transgenic plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant. Suitably, the transgenic modification alters the expression or function or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent polypeptide, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell including biolistics, gene gun techniques, *Agrobacterium*-mediated transformation, viral vector-mediated transformation, freeze-thaw method, microparticle bombardment, direct DNA uptake, sonication, microinjection, plant virus-mediated transfer, and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified polypeptide operably linked, in the sense or antisense orientation, to regulatory sequences are joined to appropriate T-DNA sequences by conventional methods. These are introduced into protoplasts by polyethylene glycol techniques or by electroporation techniques, both of which are standard. Alternatively, such vectors comprising recombinant DNA molecules encoding the subject purified polypeptide are introduced into live *Agrobacterium* cells, which then transfer the DNA into the plant cells. Transformation by naked DNA without accompanying T-DNA vector sequences can be accomplished via fusion of protoplasts with DNA-containing liposomes or via electroporation. Naked DNA unaccompanied by T-DNA vector sequences can also be used to transform cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease, the promoter of 82E4 and the promoter of SAG genes. Suitable anther-specific promoters can be used. Suitable root-preferred promoters known to persons skilled in the art may be selected. Suitable seed-preferred promoters include both seed-specific promoters (those promoters active during seed development such as promoters of seed storage polypeptides) and seed-germinating promoters (those promoters active during seed germination). Such seed-preferred promoters include Cim1 (cytokinin-induced message); cZ19B1 (maize 19 kDa zein); milps (myo-inositol-1-phosphate synthase); mZE40-2, also known as Zm-40; nuclc; and celA (cellulose synthase). Gama-zein is an endosperm-specific promoter. Glob-1 is an embryo-specific promoter. For dicots, seed-specific promoters include bean beta-phaseolin, napin, β-conglycinin, soybean lectin, cruciferin, and the like. For monocots, seed-specific promoters include a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an Itp2 promoter, cim1 promoter, maize end1 and end2 promoters, nuc1 promoter, Zm40 promoter, eepl and eep2; lec1, thioredoxin H promoter; mlip15 promoter, PCNA2 promoter; and the shrunken-2 promoter. Examples of inducible promoters include promoters responsive to pathogen attack, anaerobic conditions, elevated temperature, light, drought, cold temperature, or high salt concentration. Pathogen-inducible promoters include those from pathogenesis-related polypeptides (PR polypeptides), which are induced following infection by a pathogen (for example, PR polypeptides, SAR polypeptides, beta-1,3-glucanase, chitinase).

In addition to plant promoters, other suitable promoters may be derived from bacterial origin for example, the octopine synthase promoter, the nopaline synthase promoter and other promoters derived from Ti plasmids, or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

Suitable methods of introducing polynucleotides into plant cells and subsequent insertion into the plant genome include microinjection (*Biotechniques* (1986) 4:320-334), electroporation (*Proc. Natl. Acad. Sci. USA* (1986) 83:5602-5606), *Agrobacterium*-mediated transformation (U.S. Pat. Nos. 5,981,840 and 5,563,055), direct gene transfer (*EMBO J.* (1984) 3:2717-2722), and ballistic particle acceleration (U.S. Pat. Nos. 4,945,050, 5,879,918, 5,886,244, 5,932,782; Plant Cell, Tissue, and Organ Culture: Fundamental Methods, ed. Gamborg and Phillips (Springer-Verlag, Berlin) (1995); and *Biotechnology* (1988) 6:923-926).

b. Mutation

A plant or plant cell comprising a mutation in one or more polynucleotides or polypeptides described herein is disclosed, wherein said mutation results in modulated function or activity of NtSUS or the polypeptide(s) encoded thereby.

There is provided a method for modulating the level of a NtSUS polypeptide in a (cured) plant or in (cured) plant material said method comprising introducing into the genome of said plant one or more mutations that modulate expression of at least one NtSUS gene, wherein said at least one gene is selected from the sequences according to the present disclosure.

There is also provided a method for identifying a plant with modulated levels of reducing sugars, said method comprising screening a polynucleotide sample from a plant of interest for the presence of one or more mutations in the sequences according to the present disclosure, and optionally correlating the identified mutation(s) with mutation(s) that are known to modulate levels of reducing sugars.

There is also disclosed a plant or plant cell that is heterozygous or homozygous for one or more mutations in a NtSUS gene according to the present disclosure, wherein said mutation results in modulated expression of the gene or function or activity of the NtSUS polypeptide encoded thereby.

A number of approaches can be used to combine mutations in one plant including sexual crossing. A plant having one or more favourable heterozygous or homozygous mutations in a gene according to the present disclosure that modulates expression of the gene or the function or activity of the polypeptide encoded thereby can be crossed with a plant having one or more favourable heterozygous or homozygous mutations in one or more other genes that modulate expression thereof or the function or activity of the polypeptide encoded thereby. In one embodiment, crosses are made in order to introduce one or more favourable heterozygous or homozygous mutations within gene according to the present disclosure within the same plant.

The function or activity of one or more polypeptides of the present disclosure in a plant is increased or decreased if the function or activity is lower or higher than the function or activity of the same polypeptide(s) in a plant that has not been modified to inhibit the function or activity of that polypeptide and which has been cultured, harvested and cured using the same protocols.

In some embodiments, the mutation(s) is introduced into a plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded polypeptide can be determined using methods that are well known in the art. Insertional mutations in gene exons usually result in null-mutants. Mutations in conserved residues can be particularly effective in inhibiting the metabolic function of the encoded polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Fragments of polynucleotides and polypeptides are also disclosed. Fragments of a polynucleotide may encode polypeptide fragments that retain the biological function of the native polypeptide and hence are involved in the metabolite transport network in a plant. Alternatively, fragments of a polynucleotide that are useful as hybridization probes or PCR primers generally do not encode fragment polypeptides retaining biological function. Furthermore, fragments of the disclosed polynucleotides include those that can be assembled within recombinant constructs as discussed herein. Fragments of a polynucleotide may range from at least about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides or about 1400 nucleotides and up to the full-length polynucleotide encoding the polypeptides described herein. Fragments of a polypeptide may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, and up to the full-length polypeptide described herein. Mutant polypeptide variants can be used to create mutant, non-naturally occurring or transgenic plants (for example, mutant, non-naturally occurring, transgenic, man-made or genetically engineered plants) or plant cells comprising one or more mutant polypeptide variants. Suitably, mutant polypeptide variants retain the function of the unmutated polypeptide. The function of the mutant polypeptide variant may be higher, lower or about the same as the unmutated polypeptide.

Mutations in the polynucleotides and polypeptides described herein can include man-made mutations or synthetic mutations or genetically engineered mutations. Mutations in the polynucleotides and polypeptides described herein can be mutations that are obtained or obtainable via a process which includes an in vitro or an in vivo manipulation step. Mutations in the polynucleotides and polypeptides described herein can be mutations that are obtained or obtainable via a process which includes intervention by man.

Methods that introduce a mutation randomly in a polynucleotide can include chemical mutagenesis and radiation mutagenesis. Chemical mutagenesis involves the use of exogenously added chemicals—such as mutagenic, teratogenic, or carcinogenic organic compounds—to induce mutations. Mutagens that create primarily point mutations and short deletions, insertions, missense mutations, simple sequence repeats, transversions, and/or transitions, including chemical mutagens or radiation, may be used to create the mutations.

Mutagens include ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)amino-propylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. The dosage of the mutagenic chemical or radiation is determined experimentally for each type of plant tissue such that a mutation frequency is obtained that is below a threshold level characterized by lethality or reproductive sterility. Any method of plant polynucleotide preparation known to those of skill in the art may be used to prepare the plant polynucleotide for mutation screening.

The mutation process may include one or more plant crossing steps.

After mutation, screening can be performed to identify mutations that create premature stop codons or otherwise non-functional genes. After mutation, screening can be performed to identify mutations that create functional genes that are capable of being expressed at increased or decreased levels. Screening of mutants can be carried out by sequencing, or by the use of one or more probes or primers specific to the gene or polypeptide. Specific mutations in polynucleotides can also be created that can result in modulated gene expression, modulated stability of mRNA, or modulated stability of polypeptide. Such plants are referred to herein as "non-naturally occurring" or "mutant" plants. Typically, the mutant or non-naturally occurring plants will include at least a portion of foreign or synthetic or man-made nucleotide (for example, DNA or RNA) that was not present in the plant before it was manipulated. The foreign nucleotide may be a single nucleotide, two or more nucleotides, two or more contiguous nucleotides or two or more non-contiguous nucleotides—such as at least 10, 20, 30, 40, 50,100, 200, 300, 400, 500, 600, 700, 800, 900, 1000, 1100, 1200, 1300, 1400 or 1500 or more contiguous or non-contiguous nucleotides.

c. Transgenics and Gene Editing

Other than mutagenesis, compositions that can modulate the expression or function or activity of one or more of the NtSUS polynucleotides or polypeptides encoded thereby include sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more polypeptides; sequence-specific polynucleotides that can interfere with the enzymatic function of one or more polypeptides or the binding function of one or more polypeptides with respect to substrates or regulatory polypeptides; antibodies that exhibit specificity for one or more polypeptides; small molecule compounds that can interfere with the stability of one or more polypeptides or the enzymatic function of one or more polypeptides or the binding function of one or more polypeptides; zinc finger polypeptides that bind one or more polynucleotides; and meganucleases that have function towards one or more polynucleotides. Gene editing technologies, genetic editing technologies and genome editing technologies are well known in the art.

d. Zinc Finger Nucleases

Zinc finger polypeptides can be used to modulate the expression or function or activity of one or more of the NtSUS polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger polypeptide binding. Alternatively, the genomic DNA sequence is searched for two unique sites for zinc finger polypeptide binding wherein both sites are on opposite strands and close together, for example, 1, 2, 3, 4, 5, 6 or more base pairs apart. Accordingly, zinc finger polypeptides that bind to polynucleotides are provided.

A zinc finger polypeptide may be engineered to recognize a selected target site in a gene. A zinc finger polypeptide can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the polynucleotide target and that does not occur in the cell or organism comprising the polynucleotide which is to be modified. Methods for the design of zinc finger polypeptide which binds specific polynucleotides which are unique to a target gene are known in the art.

In other embodiments, a zinc finger polypeptide may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the disclosure provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger polypeptide and zinc finger nuclease to a plant are similar to those described below for delivery of meganuclease.

e. Meganucleases

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more NtSUS polynucleotides described herein. The meganuclease may be an engineered meganuclease with altered DNA-recognition properties. Meganuclease polypeptides can be delivered into plant cells by a variety of different mechanisms known in the art.

The disclosure encompass the use of meganucleases to inactivate a NtSUS polynucleotide(s) described herein (or any combination thereof as described herein) in a plant cell or plant. Particularly, the disclosure provides a method for inactivating a NtSUS polynucleotide in a plant using a meganuclease comprising: a) providing a plant cell comprising a NtSUS polynucleotide as described herein; (b) introducing a meganuclease or a construct encoding a meganuclease into said plant cell; and (c) allowing the meganuclease to substantially inactivate the NtSUS polynucleotide(s)

Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the function of the engineered meganuclease to cleave and mutate the meganuclease recognition site.

f. TALENs

One method of gene editing involves the use of transcription activator-like effector nucleases (TALENs) which induce double-strand breaks which cells can respond to with repair mechanisms. NHEJ reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. For certain applications, it may be desirable to precisely remove the NtSUS polynucleotide from the genome of the plant. Such applications are possible using a pair of engineered meganucleases, each of which cleaves a meganuclease recognition site on either side of the intended deletion. TALENs that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

g. CRISPR/Cas

Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) polypeptides to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of polypeptide transcription factors. CRISPR/Cas technology was implemented in plants in the method of international application WO 2015/189693 A1, which discloses a viral-mediated genome editing platform that is broadly applicable across plant species. The RNA2 genome of the tobacco rattle virus (TRV) was engineered to carry and deliver guide RNA into *Nicotiana benthamiana* plants overexpressing Cas9 endonuclease. In the context of the present disclosure, a guide RNA may be derived from any of the NtSUS polynucleotide sequences disclosed herein and the teaching of WO 2015/189693 A1 applied to edit the genome of a plant cell and obtain a desired mutant plant. The fast pace of the development of the technology has generated a great variety of protocols with broad applicability in plantae, which have been well catalogued in a number of recent scientific review articles (for example, *Plant Methods* (2016) 12:8; and *Front Plant Sci*. (2016) 7: 506). A review of CRISPR/Cas systems with a particular focus on its application in plants is in *Biotechnology Advances* (2015) 33, 1, p 41-52. Bortesi and Fischer also make comparisons between the CRISPR/Cas technology, zinc finger nucleases, and TALENs. More recent developments in the use of CRISPR/Cas for manipulating plant genomes are discussed in *Acta Pharmaceutica Sinica B* (2017) 7, 3, p 292-302) and *Curr. Op. in Plant Biol*. (2017) 36, 1-8. CRISPR/Cas9 plasmids for use in plants are listed in "addgene", the non-profit plasmid repository (addgene.org), and CRISPR/Cas plasmids are commercially available.

h. Antisense Modification

Antisense technology is another well-known method that can be used to modulate the expression or activity of a NtSUS polypeptide. A polynucleotide of the NtSUS gene to be repressed is cloned and operably linked to a regulatory region and a transcription termination sequence so that the antisense strand of RNA is transcribed. The recombinant construct is then transformed into a plant cell and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' polynucleotide. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA (siRNA) duplexes of 21-24 bp length by RNases III, which are double-stranded RNA-specific endonucleases. The siRNAs can be subsequently recognized by RNA-induced silencing complexes that promote the unwinding of siRNA through an ATP-dependent process. The unwound antisense strand of the siRNA guides the activated RNA-induced silencing complexes to the targeted mRNA comprising a sequence complementary to the siRNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the siRNA strand. The activated RNA-induced silencing complexes can be recycled to catalyze another cleavage event.

Interfering RNA expression vectors may comprise interfering RNA constructs encoding interfering RNA polynucleotides that exhibit RNA interference by reducing the expression level of mRNAs, pre-mRNAs, or related RNA variants. The expression vectors may comprise a promoter positioned upstream and operably-linked to an Interfering RNA construct, as further described herein. Interfering RNA expression vectors may comprise a suitable minimal core promoter, a Interfering RNA construct of interest, an upstream (5') regulatory region, a downstream (3') regulatory region, including transcription termination and polyadenylation signals, and other sequences known to persons skilled in the art, such as various selection markers.

The double-stranded RNA molecules may include siRNA molecules assembled from a single oligonucleotide in a stem-loop structure, wherein self-complementary sense and antisense regions of the siRNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating interfering RNA.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated polynucleotide that is situated between two complementary polynucleotides regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the siRNA molecule is a double-stranded RNA or ssRNA molecule between about 15 and about 35 nucleotides in length. In another embodiment, the siRNA molecule is a double-stranded RNA or ssRNA molecule between about 17 and about 30 nucleotides in length. In another embodiment, the siRNA molecule is a double-stranded RNA or ssRNA molecule between about 19 and about 25 nucleotides in length. In another embodiment, the siRNA molecule is a double-stranded RNA or ssRNA molecule between about 21 to about 23 nucleotides in length. In certain embodiments, hairpin structures with duplexed regions longer than 21 nucleotides may promote effective siRNA-directed silencing, regardless of loop sequence and length. Exemplary sequences for RNA interference are described herein.

The target mRNA sequence is typically between about 14 to about 50 nucleotides in length. The target mRNA can, therefore, be scanned for regions between about 14 and about 50 nucleotides in length that preferably meet one or more of the following criteria: an A+T/G+C ratio of between about 2:1 and about 1:2; an AA dinucleotide or a CA dinucleotide at the 5' end; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected sequence is unique to the target mRNA. Alternatively, a sequence can be selected (and a siRNA sequence designed) using computer software available commercially (for example, OligoEngine, Target Finder and the siRNA Design Tool which are commercially available).

In one embodiment, target mRNA sequences are selected that are between about 14 and about 30 nucleotides in length that meet one or more of the above criteria. In another embodiment, sequences are selected that are between about 16 and about 30 nucleotides in length that meet one or more of the above criteria. In a further embodiment, sequences are selected that are between about 19 and about 30 nucleotides in length that meet one or more of the above criteria. In another embodiment, sequences are selected that are between about 19 and about 25 nucleotides in length that meet one or more of the above criteria.

In an exemplary embodiment, the siRNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotides described herein. The specific antisense sequence comprised by the siRNA molecule can be identical or substantially identical to the complement. In one embodiment, the specific antisense sequence comprised by the siRNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

One method for inducing double stranded RNA-silencing in plants is transformation with a gene construct producing hairpin RNA (see Nature (2000) 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (*Plant J.* (2001), 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617).

Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

The interfering RNA molecules can comprise one or more 5' or 3'-cap structures. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the function, cellular distribution, cellular uptake, bioavailability or stability of the interfering RNA molecule. The polynucleotides may be synthesized or modified by methods well established in the art. Chemical modifications include 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate.

Ligands may be conjugated to an interfering RNA molecule, for example, to enhance its cellular absorption. In certain embodiments, a hydrophobic ligand is conjugated to the molecule to facilitate direct permeation of the cellular membrane. In certain instances, conjugation of a cationic ligand to oligonucleotides often results in improved resistance to nucleases.

"Targeted Induced Local Lesions In Genomes" (TILLING) is another mutagenesis technology that can be used to generate and/or identify polynucleotides encoding polypeptides with modified expression, function or activity. TILLING also allows selection of plants carrying such mutants. TILLING combines high-density mutagenesis with high-throughput screening methods. Methods for TILLING are well known in the art (see McCallum et al., (2000) *Nat Biotechnol* 18: 455-457 and Stemple (2004) *Nat Rev Genet* 5(2): 145-50).

Various embodiments are directed to expression vectors comprising one or more of the NtSUS polynucleotides or interfering RNA constructs that comprise one or more NtSUS polynucleotides described herein.

Various embodiments are directed to expression vectors comprising one or more of the NtSUS polynucleotides or one or more interfering RNA constructs described herein.

Various embodiments are directed to expression vectors comprising one or more NtSUS polynucleotides or one or more interfering RNA constructs encoding one or more interfering RNA polynucleotides described herein that are capable of self-annealing to form a hairpin structure, in which the construct comprises (a) one or more of the NtSUS polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed NtSUS polynucleotides can be utilised for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference can be enzymatically converted to siRNAs to modulate RNA levels.

Thus, various embodiments are directed to expression vectors comprising one or more NtSUS polynucleotides or interfering RNA constructs described herein encoding interfering RNA polynucleotides capable of self-annealing, in which the construct comprises (a) one or more of the NtSUS polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the NtSUS polypeptides described herein (or any combination thereof as described herein) by promoting co-suppression of gene expression.

Various compositions and methods are provided for modulating the endogenous gene expression level by modulating the translation of mRNA. A host (tobacco) plant cell can be transformed with an expression vector comprising: a promoter operably-linked to a NtSUS polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a NtSUS polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

i. Mobile Genetic Elements

Alternatively, genes can be targeted for inactivation by introducing transposons (for example, IS elements) into the genomes of plants of interest. These mobile genetic elements can be introduced by sexual cross-fertilization and insertion mutants can be screened for loss in polypeptide function. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

j. Ribozymes

Alternatively, NtSUS polynucleotides can be targeted for inactivation by introducing ribozymes derived from a number of small circular RNAs that are capable of self-cleavage and replication in plants. These RNAs can replicate either alone (viroid RNAs) or with a helper virus (satellite RNAs).

Examples of suitable RNAs include those derived from avocado sunblotch viroid and satellite RNAs derived from tobacco ringspot virus, lucerne transient streak virus, velvet tobacco mottle virus, *Solanum nodiflorum* mottle virus, and subterranean clover mottle virus. Various target RNA-specific ribozymes are known to persons skilled in the art.

4. Plants

The mutant or non-naturally occurring plants or plant cells can have any combination of one or more mutations in one or more NtSUS genes which results in modulated expression or function or activity of those genes or their gene products. For example, the mutant or non-naturally occurring plants or plant cells may have a single mutation in a single NtSUS gene; multiple mutations in a single NtSUS gene; a single mutation in two or more or three or more or four or more NtSUS genes; or multiple mutations in two or more or three or more or four or more NtSUS genes. By way of further example, the mutant or non-naturally occurring plants or plant cells may have one or more mutations in a specific portion of the NtSUS gene(s)—such as in a region of the NtSUS gene that encodes an active site of the NtSUS polypeptide or a portion thereof. By way of further example, the mutant or non-naturally occurring plants or plant cells may have one or more mutations in a region outside of one or more NtSUS gene(s)—such as in a region upstream or downstream of the NtSUS gene it regulates provided that they modulate the function or expression of the NtSUS gene(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant polynucleotide is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

a. Preparation of Modified Plants, Screening, and Crossing

Prepared NtSUS polynucleotides from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the samples are optionally pooled, they can be subjected to polynucleotide-specific amplification techniques, such as PCR. Any one or more primers or probes specific to the gene or the sequences immediately adjacent to the gene may be utilized to amplify the sequences within the optionally pooled sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. See, for example, McCormick et al., Plant Cell Reports 5:81-84 (1986). These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

Accordingly, in a further aspect there is provided a method of preparing a mutant plant. The method involves providing at least one cell of a plant comprising a NtSUS gene encoding a functional NtSUS polynucleotide described herein (or any combination thereof as described herein). Next, the at least one cell of the plant is treated under conditions effective to modulate the function of the NtSUS polynucleotide(s) described herein. The at least one mutant plant cell is then propagated into a mutant plant, where the mutant plant has a modulated level of NtSUS polypeptide(s) described (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term “mutant plant” includes mutant plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. The same technique can also be applied to the introgression of one or more non-naturally occurring mutation(s) from a first plant into a second plant. Plants showing a desired trait may be screened out of a pool of mutant plants. Suitably, the selection is carried out utilising the knowledge of the polynucleotide as described herein. Consequently, it is possible to screen for a genetic trait as compared to a control. Such a screening approach may involve the application of conventional amplification and/or hybridization techniques as discussed herein. Thus, a further aspect of the present disclosure relates to a method for identifying a mutant plant comprising the steps of: (a) providing a sample comprising a NtSUS polynucleotide from a plant; and (b) determining the sequence of the NtSUS polynucleotide, wherein a difference in the sequence of the NtSUS polynucleotide as compared to the NtSUS polynucleotide of a control plant is indicative that said plant is a mutant plant. In another aspect there is provided a method for identifying a mutant plant which accumulates increased or decreased levels of reducing sugar(s) as compared to a control plant comprising the steps of: (a) providing a sample from a plant to be screened; (b) determining if said sample comprises one or more mutations in one or more of the NtSUS polynucleotides described herein; and (c) determining the level of at least one reducing sugar of said plant. Suitably the level of at least one reducing sugar is determined in green leaves, early cured leaves or in cured leaves. In another aspect there is provided a method for preparing a mutant plant which has increased or decreased levels of at least one reducing sugar as compared to a control plant comprising the steps of: (a) providing a sample from a first plant; (b) determining if said sample comprises one or more mutations in one or more the NtSUS polynucleotides described herein that result in modulated levels of at least one reducing sugar; and (c) transferring the one or more mutations into a second plant. Suitably the level of at least one reducing sugar is determined in green leaves, early cured leaves or in cured leaves. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has increased or decreased levels of at least one reducing sugar as compared to a control plant comprising the steps of: (a) providing a sample from a first plant; (b) determining if said sample comprises one or more mutations in one or more of the NtSUS polynucleotides described herein that results in modulated levels of at least one reducing sugar; and (c) introgressing the one or more mutations from the first plant into a second plant. Suitably the level of at least one reducing sugar is determined in green leaves, early cured leaves or in cured leaves. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the “mutant plants” may have one or more mutations localised only to a specific region of the plant—such as within the sequence of the one or more NtSUS polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one genomic region of the plant—such as within the sequence of one or more of the NtSUS polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the NtSUS polynucleotide(s) described herein; or may not have one or more mutations in one or more, two or more, three or more, four or more or five or more introns of the NtSUS polynucleotide(s) described herein; or may not have one or more mutations in a promoter of the NtSUS polynucleotide(s) described herein; or may not have one or more mutations in the 3' untranslated region of the NtSUS polynucleotide(s) described herein; or may not have one or more mutations in the 5' untranslated region of the NtSUS polynucleotide(s)

described herein; or may not have one or more mutations in the coding region of the NtSUS polynucleotide(s) described herein; or may not have one or more mutations in the non-coding region of the NtSUS polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a NtSUS polynucleotide described herein comprising: (a) subjecting a plant, a plant cell or plant material to mutagenesis; (b) obtaining a sample from said plant, plant cell or plant material or descendants thereof; and (c) determining the polynucleotide sequence of the NtSUS gene or a variant or a fragment thereof, wherein a difference in said sequence is indicative of one or more mutations therein. This method also allows the selection of plants having mutation(s) that occur(s) in genomic regions that affect the expression of the NtSUS gene in a plant cell, such as a transcription initiation site, a start codon, a region of an intron, a boundary of an exon-intron, a terminator, or a stop codon.

b. Plant Families, Species, Varieties, Seeds, and Tissue Culture

Plants suitable for use in genetic modification include monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., Sorghum spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), Salix spp. (willow), *Eucalyptus* spp. (*eucalyptus*), Triticosecale (tritic wheat times rye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), Musyclise alca (banana), *Solanum tuberosum* (potato), *Brassica oleracea* (broccoli, cauliflower, Brussels sprouts), *Camellia sinensis* (tea), Fragaria *ananassa* (strawberry), *Theobroma cacao* (cocoa), Coffeycliseca (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), Rosa spp. (rose), *Dianthus* caryophyllus (carnation), *Petunia* spp. (*petunia*), Poinsettia *pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), Acer spp. (maple), *Hordeum vulgare* (barley), *Poa pratensis* (bluegrass), *Lolium* spp. (ryegrass) and *Phleum pratense* (timothy), *Panicum virgatum* (switchgrass), Sorghuycliseor (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant tobacco, non-naturally occurring tobacco or transgenic tobacco plants or plant cells modified to modulate gene expression levels thereby producing a plant or plant cell—such as a tobacco plant or plant cell—in which the expression level of a polypeptide is modulated within tissues of interest as compared to a control. The disclosed compositions and methods can be applied to any species of the genus *Nicotiana*, including *N. rustica* and *N. tabacum* (for example, LA B21, LN KY171, TI 1406, Basma, *Galpao*, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosuata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N.* x *sanderae*. In one embodiment, the plant is *N. tabacum*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC *Galpao* tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, Va. 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket A1, Basma Drama B84/31, BasmaI Zichna ZP4/B, Basma Xanthi BX 2A, Batek, Besuki Jember, C104, Coker 347, Criollo Misionero, Delcrest, Djebel 81, DVH 405, Galpão Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or function of a NtSUS polynucleotide(s) described herein (or any combination thereof as described herein). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a polynucleotide conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include cells from leaves, pollen, embryos, cotyledons, hypocotyls, roots, root tips, anthers, flowers and a part thereof, ovules, shoots, stems, stalks, pith and capsules or callus or protoplasts derived therefrom.

The plant material that is described herein can be cured tobacco material—such as flue cured—such as Virginia type—or sun-cured—such as Burley type and Dark type—tobacco material.

The plant material that is described herein can be air cured tobacco material—such as Burley type and Dark type.

The CORESTA recommendation for tobacco curing is described in: CORESTA Guide N° 17, April 2016, Sustainability in Leaf Tobacco Production.

c. Modulating Reducing Sugar Content

One object is to provide mutant, transgenic or non-naturally occurring plants or parts thereof that exhibit modulated levels of at least one reducing sugar in the plant material, for example, in cured leaves. Suitably, mutant, transgenic or non-naturally occurring plants or parts thereof that exhibit modulated levels of at least one reducing sugar as compared to a control plant. Suitably, the mutant, transgenic or non-naturally occurring plants or parts thereof have substantially the same visual appearance as the control plant.

Accordingly, there is described herein mutant, transgenic or non-naturally occurring plants or parts thereof or plant cells that have modulated levels of at least one reducing sugar as compared to control cells or control plants. The mutant, transgenic or non-naturally occurring plants or plant cells have been modified to modulate the synthesis or function of one or more of the NtSUS polypeptides described herein by modulating the expression of one or more of the corresponding NtSUS polynucleotides described herein. Suitably, the modulated levels of at least one reducing sugar are observed in at least the green leaves, suitably early cured or cured leaves. In certain embodiments, the level of reducing sugars in the plant—such as the green leaves, suitably early cured or cured leaves or cured tobacco—may be modulated. In certain embodiments, the level of reducing sugars in the plant—such as the green leaves, suitably early cured leaves, cured leaves or cured tobacco—may be modulated.

In certain embodiments the activity and/or expression of or more of NtSUS1-S, NtSUS1-T, NtSUS2-S, NtSUS2-T, NtSUS3-S, NtSUS3-T, NtSUS4-S, NtSUS4-T, NtSUS5-S, NtSUS5-T, NtSUS6-S and NtSUS6-T is modulated.

In certain embodiments, the activity and/or expression of or more of NtSUS2-S, NtSUS2-T, NtSUS3-S, NtSUS3-T, NtSUS4-S and NtSUS4-T is modulated.

In certain embodiments, the activity and/or expression of one or more of NtSUS2-S, NtSUS2-T, NtSUS3-S, NtSUS3-T, NtSUS4-S and NtSUS4-T is modulated and the activity and/or expression of one or more of NtSUS1-S, NtSUS1-T, NtSUS5-S, NtSUS5-T, NtSUS6-S and NtSUS6-T is not modulated.

In certain embodiments, the activity and/or expression of NtSUS2-S, NtSUS2-T, NtSUS3-S, NtSUS3-T, NtSUS4-S and NtSUS4-T is modulated and the activity and/or expression of NtSUS1-S, NtSUS1-T, NtSUS5-S, NtSUS5-T, NtSUS6-S and NtSUS6-T is not modulated.

In certain embodiments, the activity and/or expression of or more of NtSUS2-S, NtSUS3-S, NtSUS3-T and NtSUS4-S is modulated and the activity and/or expression of one or more of NtSUS1-S, NtSUS1-T, NtSUS2-T, NtSUS4-T, NtSUS5-S, NtSUS5-T, NtSUS6-S and NtSUS6-T is not modulated.

In certain embodiments, the activity and/or expression of NtSUS2-S, NtSUS3-S, NtSUS3-T and NtSUS4-S is modulated and the activity and/or expression of NtSUS1-S, NtSUS1-T, NtSUS2-T, NtSUS4-T, NtSUS5-S, NtSUS5-T, NtSUS6-S and NtSUS6-T is not modulated. A further aspect, relates to a mutant, non-naturally occurring or transgenic plant or cell, wherein the expression or the function of one or more of the NtSUS polypeptides described herein is modulated and a part of the plant (for example, the green leaves, suitably early cured or cured leaves or cured tobacco) have decreased levels of at least one reducing sugar of at least 5% therein as compared to a control plant in which the expression or the function of said NtSUS polypeptide(s) has not been modulated. In certain embodiments, the level of at least one reducing sugar in the plant—such as the green leaves, suitably early cured or cured leaves or cured tobacco—may be modulated, for example, by at least about 5%.

A still further aspect, relates to a cured plant material—such as cured leaf or cured tobacco—derived or derivable from a mutant, non-naturally occurring or transgenic plant or cell, wherein expression of one or more of the NtSUS polynucleotides described herein or the function of the NtSUS polypeptide encoded thereby is modulated and wherein the level of at least one reducing sugar is modulated by at least 5% as compared to a control plant.

Suitably the visual appearance of said plant or part thereof (for example, leaf) is substantially the same as the control plant. Suitably, the plant is a tobacco plant or a coffee plant.

Embodiments are also directed to compositions and methods for producing mutant, non-naturally occurring or transgenic plants or plant cells that have been modified to modulate the expression or function of the one or more of the NtSUS polynucleotides or NtSUS polypeptides described herein which can result in plants or plant components (for example, leaves—such as green leaves or early cured or cured leaves—or tobacco) or plant cells with modulated reducing sugar content.

The mutant, non-naturally occurring or transgenic plants obtained according to this disclosure can be similar or substantially the same in visual appearance to the corresponding control plants. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant.

In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants. Suitably, the plant is a tobacco plant or a coffee plant.

In another aspect, there is provided a method for modulating the amount of at least one reducing sugar in at least a part of a plant (for example, the leaves—such as cured leaves—or in tobacco), comprising the steps of: (i) modulating the expression or function of an one or more of the NtSUS polypeptides described herein (or any combination thereof as described herein), suitably, wherein the NtSUS polypeptide(s) is encoded by the corresponding NtSUS polynucleotides described herein; (ii) measuring the level of the at least one reducing sugar in at least a part (for example, the leaves—such as cured leaves—or tobacco or in smoke) of the mutant, non-naturally occurring or transgenic plant obtained in step (i); and (iii) identifying a mutant, non-naturally occurring or transgenic plant in which the level of the at least one reducing sugar therein has been modulated in comparison to a control plant. Suitably, the visual appearance of said mutant, non-naturally occurring or transgenic plant is substantially the same as the control plant. Suitably, the plant is a tobacco plant.

In another aspect, there is provided a method for modulating the amount of at least one reducing sugar in at least a part of cured plant material—such as cured leaf—comprising the steps of: (i) modulating the expression or function of an one or more of the NtSUS polypeptides (or any combination thereof as described herein), suitably, wherein the NtSUS polypeptide(s) is encoded by the corresponding NtSUS polynucleotides described herein; (ii) harvesting plant material—such as one or more of the leaves—and curing for a period of time; (iii) measuring the level of the at least one reducing sugar in at least a part of the cured plant material obtained in step (ii) or during step (ii); and (iv) identifying cured plant material in which the level of the at least one reducing sugar therein has been modulated in comparison to a control plant.

An increase in expression as compared to the control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more, which includes an increase in transcriptional function or NtSUS polynucleotide expression or NtSUS polypeptide expression or a combination thereof.

An increase in function or activity as compared to a control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional function or NtSUS polynucleotide expression or NtSUS polypeptide expression or a combination thereof.

A reduction in function or activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

Polynucleotides and recombinant constructs described herein can be used to modulate the expression or function or activity of the NtSUS polynucleotides or NtSUS polypeptides described herein in a plant species of interest, suitably tobacco.

A number of polynucleotide based methods can be used to increase gene expression in plants and plant cells. By way of example, a construct, vector or expression vector that is compatible with the plant to be transformed can be prepared which comprises the gene of interest together with an upstream promoter that is capable of overexpressing the gene in the plant or plant cell. Exemplary promoters are described herein. Following transformation and when grown under suitable conditions, the promoter can drive expression in order to modulate the levels of NtSUS in the plant, or in a specific tissue thereof. In one exemplary embodiment, a vector carrying one or more NtSUS polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

The expression of sequences from promoters can be enhanced by including expression control sequences, including enhancers, chromatin activating elements, transcription factor responsive elements and the like. Such control sequences may be constitutive, and upregulate transcription in a universal manner; or they may be facultative, and upregulate transcription in response to specific signals. Signals associated with senescence and signals which are active during the curing procedure are specifically indicated.

Various embodiments are therefore directed to methods for modulating the expression level of one or more NtSUS polynucleotides described herein (or any combination thereof as described herein) by integrating multiple copies of the NtSUS polynucleotide into a plant genome, comprising: transforming a plant cell host with an expression vector that comprises a promoter operably-linked to one or more NtSUS polynucleotides described herein. The polypeptide encoded by a recombinant polynucleotide can be a native polypeptide, or can be heterologous to the cell.

In one embodiment, the plant of use in the present disclosure is a plant that is flue-cured as such plants have a high reducing sugar content (greater than about 14% dry weight when field grown at the end of curing). Mutant, transgenic or non-naturally occurring plants or parts thereof that are flue-cured can have a reducing sugar content that is less than about 14% dry weight when field grown at the end of curing—such as less than about 10% dry weight when field grown at the end of curing, or less than about 5% dry weight when field grown at the end of curing, or less than about 1% dry weight when field grown at the end of curing.

In one embodiment, the plant of use in the present disclosure is a plant that is sun-cured as such plants have a reducing sugar content of greater than about 6.8% dry weight when field grown at the end of curing). Mutant, transgenic or non-naturally occurring plants or parts thereof that are sun-cured can have a reducing sugar content that is less than about 5% dry weight when field grown at the end of curing—such as less than about 2.5% dry weight when field grown at the end of curing, or less than about 1% dry weight when field grown at the end of curing.

In one embodiment, the plant of use in the present disclosure is a plant that is air-cured. Such plants have a reducing sugar content of greater than about 1.7% dry weight when field grown at the end of curing. Mutant, transgenic or non-naturally occurring plants or parts thereof that are sun-cured can have a reducing sugar content that is less than about 1.5% dry weight when field grown at the end of curing—such as less than about 1% dry weight when field grown at the end of curing, or less than about 0.5% dry weight when field grown at the end of curing.

In certain embodiments, the use of plants that are flue-cured or sun-cured is preferred.

Measuring Free Amino Acid Content

Amino acid content can be measured using various methods that are known in the art. One such method is Method MP 1471 rev 5 2011, Resana, Italy: Chelab Silliker S.r.I, Mérieux NutriSciences Company. For amino acid determination in cured plant leaves, after mid-rib removal, cured lamina are dried at 40° C. for 2-3 days, if required. Tobacco material is then ground in fine powder (~100 uM) before the analysis of amino acid content. Another method for measuring amino acid content in plant material is described in UNI EN ISO 13903:2005. In certain embodiments, the measurement of free amino acid content is performed according to UNI EN ISO 13903:2005.

Measuring Reducing Sugar Content

Reducing sugar content can be measured using a segmented-flow colorimetric method developed for analysis of tobacco samples as adapted by Skalar Instrument Co (West Chester, Pa.) and described in Tobacco Science 20: 139-144 (1976). The measurement of reducing sugar content is also described in Coresta Recommended Method 38, CRM38, CRM and ISO 15154: 2003. For reducing sugar determination in cured leaves, after mid-rib removal, cured lamina are dried at 40° C. for 2-3 days, if required. Tobacco material is then ground in fine powder (~100 uM) before the analyses of reducing sugars. In certain embodiments, the measurement of reducing sugar content is performed according to ISO 15154: 2003.

Breeding

A plant carrying a mutant allele of one or more NtSUS polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny tobacco seed, under plant growth conditions, to yield the non-naturally occurring plant. The method may further comprises: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the polynucleotide sequence information for the polynucleotide(s) described herein (or any combination thereof as described herein).

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or function of the polypeptide(s) encoded thereby. Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme function of polypeptides and polynucleotides; and polypeptide gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression, function or activity of NtSUS polypeptides or NtSUS polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

5. Modification of Other Genes

Without limitation, the plants and parts thereof described herein can be modified either before or after the expression, function or activity of the one or more NtSUS polynucleotides and/or NtSUS polypeptides according to the present disclosure have been modulated.

One or more of the following further genetic modifications can be present in the mutant, non-naturally occurring or transgenic plants and parts thereof.

One or more genes that are involved in the conversion of nitrogenous metabolic intermediates can be modified resulting in lower levels of at least one tobacco-specific nitrosamine (TSNA).

Non-limiting examples of such genes include those encoding nicotine demethylase—such as CYP82E4, CYP82E5 and CYP82E10 as described in WO2006/091194, WO2008/070274, WO2009/064771 and WO2011/088180—and nitrate reductase, as described in WO2016/046288.

One or more genes that are involved in heavy metal uptake or heavy metal transport can be modified resulting in lower heavy metal content. Non-limiting examples include genes in the family of multidrug resistance associated polypeptides, the family of cation diffusion facilitators (CDF), the family of Zrt-Irt-like polypeptides (ZIP), the family of cation exchangers (CAX), the family of copper transporters (COPT), the family of heavy-metal ATPases (for example, HMAs, as described in WO2009/074325 and WO2017/129739), the family of homologs of natural resistance-associated macrophage polypeptides (NRAMP), and other members of the family of ATP-binding cassette (ABC) transporters (for example, MRPs), as described in WO2012/028309, which participate in transport of heavy metals—such as cadmium.

Other exemplary modifications can result in plants with modulated expression or function of isopropylmalate synthase which results in a change in sucrose ester composition which can be used to alter favour profile (see WO2013/029799).

Other exemplary modifications can result in plants with modulated expression or function of threonine synthase in which levels of methional can be modulated (see WO2013/029800).

Other exemplary modifications can result in plants with modulated expression or function of one or more of neoxanthin synthase, lycopene beta cyclase and 9-cis-epoxycarotenoid dioxygenase to modulate beta-damascenone content to alter flavour profile (see WO2013/064499).

Other exemplary modifications can result in plants with modulated expression or function of members of the CLC family of chloride channels to modulate nitrate levels therein (see WO2014/096283 and WO2015/197727).

Other exemplary modifications can result in plants with modulated expression or function of one or more asparagine synthetases to modulate levels of asparagine in leaf and modulated levels of acrylamide in aerosol produced upon heating or combusting the leaf (see WO2017/042162). Examples of other modifications include modulating herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB polypeptide of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*.

Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single polypeptide and significantly delayed the evolution of resistant insects.

Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered.

Another exemplary modification results in altered reproductive capability, such as male sterility.

Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance.

Another exemplary modification results in plants in which the activity of one or more endogenous glycosyltransferases—such as N-acetylglucosaminyltransferase, β(1,2)-xylosyltransferase and a(1,3)-fucosyl-transferase is modulated (see WO2011/117249).

Another exemplary modification results in plants in which the activity of one or more nicotine N-demethylases is modulated such that the levels of nornicotine and metabolites of nornicotine—that are formed during curing can be modulated (see WO2015169927).

Other exemplary modifications can result in plants with improved storage polypeptides and oils, plants with enhanced photosynthetic efficiency, plants with prolonged shelf life, plants with enhanced carbohydrate content, and plants resistant to fungi. Transgenic plants in which the expression of S-adenosyl-L-methionine (SAM) and/or cystathionine gamma-synthase (CGS) has been modulated are also contemplated.

One or more genes that are involved in the nicotine synthesis pathway can be modified resulting in plants or parts of plants that when cured, produce modulated levels of nicotine. The nicotine synthesis genes can be selected from the group consisting of: A622, BBLa, BBLb, JRE5L1, JRE5L2, MATE1, MATE 2, MPO1, MPO2, MYC2a, MYC2b, NBB1, nic1, nic2, NUP1, NUP2, PMT1, PMT2, PMT3, PMT4 and QPT or a combination of one or more thereof.

One or more genes that are involved in controlling the amount of one or more alkaloids can be modified resulting in plants or parts of plants that produce modulated levels of alkaloid. Alkaloid level controlling genes can be selected from the group consisting of; BBLa, BBLb, JRE5L1, JRE5L2, MATE1, MATE 2, MYC2a, MYC2b, nic1, nic2, NUP1 and NUP2 or a combination of two or more thereof.

One or more such traits may be introgressed into the mutant, non-naturally occurring or transgenic plants from another cultivar or may be directly transformed into it.

Various embodiments provide mutant plants, non-naturally occurring plants or transgenic plants, as well as biomass in which the expression level of one or more polynucleotides according to the present disclosure are modulated to thereby modulate the level of polypeptide(s) encoded thereby.

6. Consumable Products

Parts of the plants described herein, particularly the leaf lamina and midrib of such plants, can be incorporated into or used in making various consumable products including but not limited to aerosol forming materials, aerosol forming devices, smoking articles, smokable articles, smokeless products, medicinal or cosmetic products, intravenous preparations, tablets, powders, and tobacco products. Examples of aerosol forming materials include tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured plant material from the mutant, transgenic and non-naturally occurring plants described herein. Processes of curing green tobacco leaves are known by those having skills in the art and include without limitation air-curing, fire-curing, flue-curing and sun-curing as described herein.

In another embodiment, there is described tobacco products including tobacco-containing aerosol forming materials comprising plant material—such as leaves, preferably cured leaves—from the mutant tobacco plants, transgenic tobacco plants or non-naturally occurring tobacco plants described herein. The tobacco products described herein can be a blended tobacco product which may further comprise unmodified tobacco.

7. Products and Methods for Crop Management and Agriculture

The mutant, non-naturally occurring or transgenic plants may have other uses in, for example, agriculture. For example, mutant, non-naturally occurring or transgenic plants described herein can be used to make animal feed and human food products.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a NtSUS polynucleotide (or any combination thereof as described herein) in a sample of polynucleotide. Accordingly, a composition is described comprising one or more primers for specifically amplifying at least a portion of one or more of the NtSUS polynucleotides and optionally one or more probes and optionally one or more reagents for conducting the amplification or detection.

Accordingly, gene specific oligonucleotide primers or probes comprising about 10 or more contiguous polynucleotides corresponding to the NtSUS polynucleotide(s) described herein are disclosed. Said primers or probes may comprise or consist of about 15, 20, 25, 30, 40, 45 or 50 more contiguous polynucleotides that hybridise (for example, specifically hybridise) to the NtSUS polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in amplification or detection). The one or more specific primers or probes can be designed and used to amplify or detect a part or all of the polynucleotide(s). By way of specific example, two primers may be used in a PCR protocol to amplify a polynucleotide fragment. The PCR may also be performed using one primer that is derived from a polynucleotide sequence and a second primer that hybridises to the sequence upstream or downstream of the polynucleotide sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a NtSUS polynucleotide(s) described herein (or any combination thereof as described herein) in a sample comprising the step of: (a) providing a sample comprising, or suspected of comprising, a polynucleotide; (b) contacting said sample with one or more primers or one or more probes for specifically detecting at least a portion of the NtSUS polynucleotide(s); and (c) detecting the presence of an amplification product, wherein the presence of an amplification product is indicative of the presence of the NtSUS polynucleotide(s) in the sample. In a further aspect, there is also provided the use of one or more primers or probes for specifically detecting at least a portion of the NtSUS polynucleotide(s). Kits for detecting at least a portion of the NtSUS polynucleotide(s) are also provided which comprise one or more primers or probes for specifically detecting at least a portion of the NtSUS polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for using the kit.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a NtSUS polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by polynucleotide variability. Thus, the present disclosure further provides a means to follow segregation of one or more genes or polynucleotides as well as chromosomal sequences genetically linked to these genes or polynucleotides using such techniques as AFLP analysis.

The invention is further described in the Examples below, which are provided to describe the invention in further detail. These examples, which set forth a preferred mode presently contemplated for carrying out the invention, are intended to illustrate and not to limit the invention.

EXAMPLES

Example 1: Identification of Key Sucrose Metabolism Genes after Curing in Burley, Va. and Oriental Tobacco Leaf To identify key functions contributing to sucrose metabolism during early curing time of Burley, Va. and Oriental tobacco leaf, an overrepresentation analysis for the function of genes up-regulated in cured leaves after 48 hours curing, as compared to the ripe leaves at harvest (log 2 fold change >2, adjusted p-value <0.05) is performed in Burley, Va. and Oriental tobacco. Genes involved in the production of reducing sugars and that are active after 48 hours curing independently of the curing types and tobacco varieties are identified. Tobacco genes involved in the production of reducing sugars are identified.

The key genes directly involved in the production of reducing sugars during early curing in leaves belong to the gene family of SUS. SUS is likely a key enzyme to drive the accumulation of reducing sugars in cured detached leaves.

The tobacco genome is found to have 12 NtSUS gene products distributed in 6 families with one S and one T copy from each ancestor: NtSUS1-S(SEQ ID NO: 1), NtSUS1-T (SEQ ID NO: 3), NtSUS2-S(SEQ ID NO: 5), NtSUS2-T (SEQ ID NO: 7), NtSUS3-S(SEQ ID NO: 9), NtSUS3-T (SEQ ID NO: 11), NtSUS4-S(SEQ ID NO: 13), NtSUS4-T (SEQ ID NO: 15), NtSUS5-S(SEQ ID NO: 17), NtSUS5-T (SEQ ID NO: 19), NtSUS6-S(SEQ ID NO: 21) and NtSUS6-T (SEQ ID NO: 23).

SUS transcripts are from the genomic sequences NtSUS2-S(SEQ ID NO: 5), NtSUS3-S(SEQ ID NO: 9), NtSUS3-T (SEQ ID NO: 11) and NtSUS4-S(SEQ ID NO: 13). These genes are up-regulated during leaf curing (senescence), as shown in Table 1. This confirms that S copies are particularly involved in the chemical modification of early cured leaves and in this particular case the increase of glucose and fructose.

Although low amounts of reducing sugar levels are found in cured leaves of Burley, compared to Virginia and Oriental (see FIG. 1), NtSUS genes are nevertheless activated in Burley (see Table 1), likely as a constitutive response to also ensure available carbon source for amino acid synthesis during the early curing phase.

In both Burley (BU) and Virginia (FC), NtSUS1-S and NtSUS1-T which are not expressed during early curing (see Table 1) are particularly expressed in root and stem, indicating a possible specific function in these tissues to deliver carbohydrates for cell wall synthesis or supply carbon resources under anoxia. On the other hand, NtSUS3-S, NtSUS3-T, NtSUS4-S, which are induced during early leaf curing, are also expressed in all organs, whereas NtSUS2-S and NtSUS2-T are mainly expressed in immature flowers and petals. NtSUS5-S, NtSUS5-T, NtSUS6-S and NtSUS6-T are expressed at low levels in all the analysed plant tissues (see Table 2).

To increase the pool of reducing sugars in cured leaves, overexpression of NtSUS2-S, NtSUS3-S, NtSUS3-T and/or NtSUS4-S using a senescence induced promoter like SAG12 or E4 might be considered (the use of a constitutive promoter may strongly change plant metabolism). On the other hand, knocking-out NtSUS2-S, NtSUS3-S, NtSUS3-T and/or NtSUS4-S may contribute to reduce the content of reducing sugars in cured leaves.

Example 2—Silencing of NtSUS Expression in Virginia Tobacco Leaf

The silencing of NtSUS in Burley tobacco is investigated to determine if these genes contribute to decreasing reducing sugar content in cured Virginia tobacco leaves. A specific DNA fragment within the coding sequence of both NtSUS is cloned with the strong constitutive *Mirabilis* Mosaic Virus (MMV) promoter in a GATEWAY vector. The NtSUS gene fragment is flanked between MMV and the 3' nos terminator sequence of the nopaline synthase gene of *Agrobacterium tumefaciens*.

To enable the selection of low reducing sugar content plants, independent T0 plant leaves and respective control lines are analyzed after 60h curing to determine the impact on reducing sugar content. The best T0 lines displaying the lowest level of reducing sugar selected. Seeds are harvested from these best T0 lines. T1 progeny are assayed by qPCR to determine the efficiency of the NtSUS silencing events in relation to decreasing the reducing sugar content.

Manipulating NtSUS genes (for example, with either a constitutive promotor or a specific senescence promotor—such as SAG12 or E4) may change the chemistry of tobacco cured leaves. Similarly knocking-out NtSUS genes using a gene editing strategy—such as CRISPR-Cas or mutant selection may change amino acid leaf chemistry of the main varieties of commercial tobacco.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

Expression of NtSUS genes during early curing in Burley (BU), Virginia (FC) and Oriental (OR)

| | BU | | | FC | | | OR | | |
|---|---|---|---|---|---|---|---|---|---|
| | Green | Ripe | 48h curing | Green | Ripe | 48h curing | Green | Ripe | 48h curing |
| NtSUS1-S | 3.4 | 0.2 | 0.0 | 10.4 | 0.0 | 0.4 | 3.4 | 0.1 | 0.5 |
| NtSUS1-T | 4.1 | 0.2 | 0.0 | 11.4 | 0.1 | 0.2 | 3.4 | 0.2 | 0.6 |
| NtSUS2-S | 0.2 | 0.3 | 28.5 | 0.3 | 0.1 | 1.7 | 0.6 | 2.3 | 17.8 |
| NtSUS2-T | 4.0 | 1.7 | 5.0 | 2.6 | 0.3 | 0.5 | 2.7 | 2.8 | 3.7 |
| NtSUS3-S | 23.4 | 55.6 | 130.4 | 14.2 | 57.8 | 82.3 | 18.7 | 42.0 | 163.9 |
| NtSUS3-T | 8.5 | 12.2 | 76.5 | 2.4 | 3.2 | 41.2 | 6.1 | 10.7 | 126.7 |
| NtSUS4-S | 11.6 | 4.9 | 22.8 | 15.5 | 3.6 | 22.9 | 19.0 | 18.9 | 105.4 |
| NtSUS4-T | 3.2 | 2.7 | 8.1 | 2.7 | 3.1 | 1.9 | 38.0 | 56.2 | 37.9 |
| NtSUS5-S | 0.6 | 0.2 | 0.1 | 5.1 | 0.1 | 0.5 | 1.4 | 0.3 | 0.8 |
| NtSUS5-T | 0.5 | 0.5 | 0.3 | 3.6 | 0.4 | 0.6 | 1.1 | 0.8 | 1.6 |
| NtSUS6-S | 7.8 | 9.5 | 8.2 | 7.6 | 7.7 | 5.4 | 7.8 | 8.2 | 8.3 |
| NtSUS6-T | 3.1 | 4.2 | 4.7 | 1.6 | 4.3 | 3.2 | 3.7 | 4.9 | 5.0 |

TABLE 2

Expression of NtSUS genes in root, stem, mid-leaf, immature flower (imflower), sepal, and petal of Burley (BU) and Virginia (FC) plants grown in the field

| | BU | | | | | | FC | | | | | |
|---|---|---|---|---|---|---|---|---|---|---|---|---|
| | root | stem | mid-leaf | imflower | sepal | petal | root | stem | mid-leaf | imflower | sepal | petal |
| NtSUS1-S | 206.4 | 294.0 | 0.9 | 8.2 | 1.6 | 6.4 | 95.7 | 129.1 | 0.7 | 31.7 | 1.1 | 0.7 |
| NtSUS1-T | 170.0 | 348.6 | 1.0 | 14.4 | 2.5 | 9.0 | 70.9 | 137.6 | 1.1 | 36.9 | 1.7 | 1.7 |
| NtSUS2-S | 26.4 | 17.0 | 0.4 | 86.1 | 12.9 | 97.9 | 27.3 | 13.5 | 0.4 | 197.3 | 7.7 | 150.3 |
| NtSUS2-T | 61.5 | 55.1 | 2.2 | 96.9 | 37.3 | 172.7 | 4.2 | 12.7 | 0.4 | 122.6 | 12.4 | 111.4 |
| NtSUS3-S | 7.7 | 23.0 | 31.8 | 10.3 | 22.5 | 32.4 | 81.0 | 98.7 | 40.4 | 14.6 | 67.5 | 34.6 |
| NtSUS3-T | 6.7 | 6.4 | 5.0 | 8.8 | 7.9 | 13.7 | 13.9 | 20.2 | 2.8 | 4.7 | 6.8 | 17.7 |
| NtSUS4-S | 26.5 | 40.0 | 8.5 | 19.4 | 14.7 | 23.4 | 30.6 | 43.4 | 6.6 | 31.4 | 10.3 | 34.1 |
| NtSUS4-T | 40.7 | 29.3 | 6.4 | 3.2 | 6.0 | 4.1 | 52.6 | 47.7 | 4.8 | 5.4 | 12.6 | 20.4 |
| NtSUS5-S | 2.6 | 6.5 | 0.5 | 5.6 | 1.4 | 1.1 | 2.2 | 2.2 | 0.3 | 4.4 | 0.5 | 0.4 |
| NtSUS5-T | 2.6 | 5.9 | 0.6 | 5.3 | 1.0 | 1.9 | 2.6 | 2.3 | 1.2 | 3.4 | 0.8 | 1.8 |
| NtSUS6-S | 8.3 | 7.8 | 7.8 | 8.9 | 6.8 | 7.1 | 9.4 | 8.5 | 6.6 | 9.5 | 7.3 | 8.6 |
| NtSUS6-T | 2.7 | 2.4 | 4.1 | 3.0 | 3.1 | 4.9 | 4.0 | 3.4 | 3.6 | 4.2 | 3.2 | 5.2 |

SEQUENCE LISTING

SEQ ID NO: 1: Polynucleotide sequence of NtSUS1-S

```
atggcagctagtggtcttagcattaagaaaagtttggaggaatccattttggctcatccagatgaaattttggctct

caagtcaaggtacattactacatataatgatattaagaactagaggcttatccaaggttttgttacatttttgaaat

tataagtttagaacctaatagtacttggtagcacttgtttccttattatctagctgttgttactgcttgttgctact

gctttctgttcatctttccttgagcccggtctatcggaaacaacctctctattctcaaagtataaggtttgcgtaca

tactacctccccagactctacttgtggaatttactgtttttgttgtgttgttgtaatctaatatttattagaatttt

actgatttttcacatatatatatctatgtcccctgtcgaaaattctatagctcatgttagctaaatacattagtacc

attgtttttaattgttttggttttggcacaggattgaaactgaagggaaaggggtaatgaaaccacttgatctcttg

aaccatttggtttctgttactagtaagacaaatggagtaaatattgtacctagtgcacttgtggaagttctcagttg
```

-continued cagccaagaagctgtgattgtaccaccaaaactagcactagctgtacgtccgaggcccggtgtatgggagtacttgt cactgaatcttaagacaaagaaagtggctgaattaagcattcctgaataccttcaattgaaagagaacactgttgat gaaaggtaaagtattagtctgcgatttcgctttgtgaaattgaagtttttgttttgattcataatgttttgtgtatc aattatgttaccagtggaaacatattggagttggattttgagccatttacaacagttacaccaccaaaaacactttc tgactctattggcaatggtttggagtttcttaatcgccacattgcttcgaaaatgtttcatgataaggagatttcca gatgcctccttgacttcctcagaaaccataactacaaaggaaaggtaataaaaaaaagtgtttctttaaacaagttg tatgattatgtgtatatttctaagtatgttaacttgaaaacagtcattgatggtgaaagaaagcattcaaagcctag agagtttccaacttgttctgaaaaaagcagaggaacatttgtgcacattgaatccagaaactccatactccaatttt gaatcaaagtttgaagagattggcttggaaagagggtggggaaacaccgctgaacgcgtgcaagacactatcagtca tcttttgcatctccttgaggctcctaacgcgtcttctttggaaaatttccttggtagaatcccattggttttcaatg ttgtgattctaactccacatggttattttgctcaagataatgtcttgggctatcctgacactggtggccaggtttgt gtccaatattttgcattcttgatcaagttctttataccatttgaaccaacaatcttnaacattcttttttggttgt gaaatgttgaataggttgtttacattcttgatcaagttccagctatggagcgtgagatgcttcatcgtatgaagctt caaggactcgatgatatcatccctcgcatccttgttgtaagtggccttaattttcctagtttcatttacacctctaa atgaaattgatctttttttgttgttttatatcaggtaacaaggctgctgcctgatgcagtaggaaccacctgtggcga gcggatggagaaagtatatggggcagaacattctcatataattcgtgttccatttagaactgagaagggaatgttgc gcaaatggatctcacgattcgaagtctggccatacatggaaactttcactgaggttggaacataaaaacaaataaaa tccattggaatgttccttctgcaattgaaaatgtcttgctaactgaagacccatttttaaattgatcatcaggatgt tgcagaagaacttgtcaaagaattgcaagctaaaccagacttgatcattggaaactacagtgagggaaatcttgctg cctctttgcttgcgaagaaatttggggctactcagtgtactattgctcatgccttggaaaaaaactaagtatccaaac tctgaccttaattggaagaagtttgatgacaagtatcatttctcaagtcagttcactgctgatctctttgccatgaa tcacactgatttcatcatcaccagcactttccaagaaattgctggaaggtaaaagcaaatgcacaccatcatagtat ttcatatttttacccttgtttatactatttccattcaccgaccccgacttgtttaggattgagccatagttgttgtt gttgtttgtttatactatttccatttgccgaccacaacttgtttaggactgaggtatagttgttgttgttggtttgt tcatattattttcattcgctaaccctaacttgtttgggactgaggcatagtagtagtagtagttgttgctattagtt tatactatttccatttgccaaccccaacttgtttggtactgagacatagttgttgttgttgttgtttgtttatacta tttccatttgccgaccccaacttgtttaggactgaggtatagttgttgttgttggtttgttcatattattttcattc gctaaccccaacttgtttgggactgaggcatagtagtagtagtagtagttgttgctattagtttatactatttccat ttgccaaccccaacttgtttggtactgagacatagttgttgttgttgtttgtttatactatttcaatttgtcgaccc caatttgtttgggaccaaggcatggttgttgttgttgtttgtttgtttttactgtttccattgatattggaacattt gttatttgcagcaaaaacactgtaggacagtatgagagtcatactgcttttaccatgcctggattgtaccgagtagt ccatggaatcgattcgtttgatccaaagttcaacattgtctccccctggggctgatatgtcaatctacttcccttaca ctgagaaggagaaaaggctaaccaacttccacccggaaattgaagaactcctctacagtcctgttgagaataaggac cacttgttagtctccttaatttgcttttatttcatcccatttatgatcgcttttatcccaacagatcgattaatcat ttgttatcaacataaacagatgtgtgttgaaggaccggaacaagccaattctctttaccatggcaaggctagatcgc gtgaagaatctaacagggctcgtggaatggtatgctaagaatgcaaggctgagggagcttgttaaccttgtggttgt aggcggagacagaaggaaagaatccaaagatttagaagagcaagcagagatgaagaagatgtatgatcttatcgaaa cctataacctgaacggccaattcaggtggatttcttcccaaatgaatcgtgtgaggaacggagaactctatcgttac attgcagacacgaggggtgctttcgttcaaccagcattctacgaggcttttggtttgacagttgtagagtctatgac ttgtggtttgccaacttttgctacttgtaatggtggaccatttgagattatagtgaatggaaaatctggtttccata -continued ttgatcctaatcaaggtgacaaggctgctgatatgttggtaaatttctttgaaaaatctaaagaagatccaagttat tgggatgctatttccaagggaggtctgcaacgtattcttgaaaagtaagcttttgcatttgattagcacaagtgcac aaccaagatttaacttttgaacaaactaaaactaaccctttttttgtattttcttttgctaggtatacatggcaaatt tattcacagaaagtgatcacactatctgggatttatggattctggaagtatgcaaccaagaatgataaagttgctag tgcaaagaagcgctatcttgagatgttttatgaacttggatttaagaaatcagtaagtgtcaattttaaaggggaac cttggatcaacggttaagttgtctttgtgcaacctataggtcaggggtttgagccgtagaagtagccactaatattt acattagggtagactgtgtacatatcacaccccttggggtacggccctttcctggatcctgtatgaacgcgggatgc cttgtgcaccgggctgtattttttttttttagtgtcacttctgtattttgtttgagcttgtttataaagtttggaaat ctgctgctaatttgtatatttgttggttgtgtatttcaggctgagaaagttccattggctattgatgaatag SEQ ID NO: 2: Polypeptide sequence of NtSUS1-S
MAASGLSIKKSLEESILAHPDEILALKSRIETEGKGVMKPLDLLNHLVSVTSKTNGVNIVPSALVEVLSCSQEAVIV

PPKLALAVRPRPGVWEYLSLNLKTKKVAELSIPEYLQLKENTVDESGNILELDFEPFTTVTPPKTLSDSIGNGLEFL

NRHIASKMFHDKEISRCLLDFLRNHNYKGKSLMVKESIQSLESFQLVLKKAAEEHLCTLNPETPYSNFESKFEEIGLE

RGWGNTAERVQDTISHLLHLLEAPNASSLENFLGRIPLVFNVVILTPHGYFAQDNVLGYPDTGGQVVYILDQVPAME

REMLHRMKLQGLDDIIPRILVVTRLLPDAVGTTCGERMEKVYGAEHSHIIRVPFRTEKGMLRKWISRFEVWPYMETF

TEDVAEELVKELQAKPDLIIGNYSEGNLAASLLAKKFGATQCTIAHALEKTKYPNSDLNWKKEDDKYHESSQFTADL

FAMNHTDFIITSTFQEIAGSKNTVGQYESHTAFTMPGLYRVVHGIDSFDPKFNIVSPGADMSIYFPYTEKEKRLTNF

HPEIEELLYSPVENKDHLCVLKDRNKPILFTMARLDRVKNLTGLVEWYAKNARLRELVNLVVVGGDRRKESKDLEEQ

AEMKKMYDLIETYNLNGQFRWISSQMNRVRNGELYRYIADTRGAFVQPAFYEAFGLTVVESMTCGLPTFATCNGGPF

EIIVNGKSGFHIDPNQGDKAADMLVNFFEKSKEDPSYWDAISKGGLQRILEKYTWQIYSQKVITLSGIYGENKYATK

NDKVASAKKRYLEMEYELGEKKSAEKVPLAIDE

SEQ ID NO: 3: Polynucleotide sequence of NtSUS1-T
atggcaggcagtggtcttagcattaaggaaagtttggaggaatccattttggctcatccagatgaaattttggctct caagtcaaggtacattactgcataatgatattaagacctagaagcggatccaagattttgttacatttttgaaatta taagtttagaatctaatatttgttatcgcttgtttccttattatcttgctgttgttactgcctgttgctactagttt ctgttcatccttccttgagctgagtttctatcggaaacaacctctctactctcaaagtaggaataagttatgcgtac acactaccctccccagactccacttgtgtaatttactgagtttgttgttgttgttgttgtaatctaatacttgttag aattttactgatttttcacatatatatctatgacccatgtcgaaaatactatagctcatgtgctaaatacattagta ccattgttttgtaattgttttggttttggaacaggattgaaactgaagggaaaggggtaatgaaaccagttgatctc ttgaaccatttggtttctgttactagtaaaacaaatggagtaaatgttgtacctagtgcacttgtggaagttctcag ttgcagccaagaagctgtgattgtaccaccaaaactagcactagctgtacgtccgaggcccggtgtatgggagtact tgtcactgaatcttaagacaaagaaagtggctgaattgagcattcctgagtaccttcaattgaaagagaatactgtt gatgaaaggtaaagtaatagtctgcgatttcgctttgtgaaattgaagtttttttgtttgattcttaatgttttgtgt atcaattatgttaccagtggaaacatcttggagttggattttgagccatttacaactgttacaacaccaaaaacact ttctgactctattggcaatggtttggagtttcttaatcgccacattgcttcgaaaatgtttcttgataaggagattg ccaagtgcctccttgactttctcagaaaccataactacaaaggaaaggtagtaaaaaaaagtgtttctttaaacaagt tgtatgattatgtgtgtatttctaaatatgtcaatttgaaaacagtcattgatggtgaaagaaagcattcaaagcct ggagagtttccaacttgttctgaaaaaaagcagaggaatatttgcacacactgaatccagaaactccatactccaaat ttgaatccaagtttgaagagattggcttggaaagagggtggggaaacaccgctgaacgcgtgcaagacaccattagt catcttttgcatctccttgaggctcctaacgcgtcttccttggaaaatttccttggtagaatcccattggttttcaa tgttgtgattctcaccccacatggttattttgctcaagataatgtcttgggctatcctgacactggtggccaggttt gtgtccgatataacatatcaagaaattttgcattcttgatcatgttctttataccatttgaaccaacattctttttt -continued tggttgtgaaatgttgaataggttgtttacattcttgatcaagttccagctatggagcgtgagatgcttcatcgtat gaagcttcaaggactcgacgatatcatccctcgcatccttgttgtaagtgcccttaattttcctggtttggtttacc tctaaatgaaattgattttctggctttctaactttttggattgatctttttgttgttttatatcaggtaactaggc tgctgcctgatgctgtaggaaccacttgtggcgagtggatggagaaagtatatggggcagaacattctcatataatt cgtgttccatttagaactgagaaaggaatgttgcgcaaatggatctcacgattcgaagtctggccatacatggaaac tttcactgaggttggaacataaaaacaaataaaaatcattggaatgttcttctgcatttgaaaatgtcttgctaact aaagactcatttttaaattaatcatcaggatgttgcagaagaacttgtcaaagaattgcaagctaaaccagacttga taattggaaactacagtgagggaaatcttgctgcctcattgcttgctaagaaatttggggctactcagtgtactatt gctcatgccttggaaaaaactaagtatccaaactctgaccttaattggaagaagtttgatgacaagtatcatttctc aagtcagttcactgctgatctttttgccatgaatcacactgatttcattatcaccagcactttccaagaaattgctg gaaggtaaaagcaaatgcacaccatcatagtatttcatatttttaccctagtttatactatttccatttgtcaactc caacttgtttgggattgaaccatagttgttgtttgtttatactatttccattcgccgaccccaacttatttgggact gagacataattgttgttattattgtttgtttgtttatactatttccattctcagaccccaacttctttgggactgag ccgtagattgttgttgttgttgttgttgttgtttgtttatgctatttccgttcaccgaccccaacttatttgggact gaggtgtagaagtagtcgttgttgtttgtttatacgacttccaattgatattcgaatgtttttatttttgcagcaag aacactgtaggacagtatgagagtcatactgcttttaccatgcctggattgtatcgagtagtccatggaatcaattc gtttgatccaaagttcaacattgtctcccctggggctgatatgtcaatctacttcccttacactgagaaggagaaaa gactaaccaacttccacccggaaattgaagaactcctctacagtcctgttgagaataaggaccacttgttagtcttc tttatttcattcatttttctacacctttttttcaacagattgattgattggttcttatcaacgtaaacagatgtgt gttgaaggaccagaacaagccaattctctttaccatggcaaggctagatcgcgtgaagaatctaacagggctcgtgg aatggtatgcaaagaatgcaaggctaagggagctcgttaaccttgtggttgtaggcggagacagaaggaaagaatcc aaagatttagaagagcaagcagagatgaagaagatgtatgatcttatcgaaacatacaacctgaatggccaattcag gtggatttcttcccaaatgaatcgtgtgaggaacggagaactttatcgatacattgcagacacgaggggtgctttcg ttcaaccagcattttatgaggcatttggtttgacagttgttgagtctatgacttgtggtttgccaacttttgctact tgtaatggtggaccatttgagattatagtgaatggaaaatctggtttccatattgatcctaatcaaggtgacaaggc tgctgatatgttggttaatttcttcgaaaaatctaaagaagatccaagttattgggatactatttccaagggtggtc tgcagcgtattcttgaaaagtaagcttttgcatttgattagcacaagtgtacaaccaagatttaacttatgaacaaa ctaaaactaaccctttttttattttcttttgctaggtatacatggcaaatttattcacagaaagtgatcacattatc tgggatttatggattctggaaatatgcaaccaagaatgacaaagttgctagtgcgaagaagcgctatcttgaaatgt tttatgaatttgggtttaagaaatcagtaagtgtcacttctgtattttgtttgagcttgtttgtaaagtttggcaat cttctgctaatttgtactatatttgttgacttgtgcatttcaggctgagaaagttccattggctattgatgaatag SEQ ID NO: 4: Polypeptide sequence of NtSUS1-T
MAGSGLSIKESLEESILAHPDEILALKSRIETEGKGVMKPVDLLNHLVSVTSKTNGVNVVPSALVEVLSCSQEAVIV

PPKLALAVRPRPGVWEYLSLNLKTKKVAELSIPEYLQLKENTVDESGNILELDFEPFTTVTTPKTLSDSIGNGLEFL

NRHIASKMELDKETAKCLLDFLRNHNYKGKSLMVKESIQSLESFQLVLKKAEEYLHTLNPETPYSKFESKFEEIGLE

RGWGNTAERVQDTISHLLHLLEAPNASSLENFLGRIPLVFNVVILTPHGYFAQDNVLGYPDTGGQVVYILDQVPAME

REMLHRMKLQGLDDIIPRILVVTRLLPDAVGTTCGEWMEKVYGAEHSHIIRVPFRTEKGMLRKWISRFEVWPYMETF

TEDVAEELVKELQAKPDLIIGNYSEGNLAASLLAKKFGATQCTTAHALEKTKYPNSDLNWKKEDDKYHFSSQFTADL

FAMNHTDFIITSTFQEIAGSKNTVGQYESHTAFTMPGLYRVVHGINSFDPKENIVSPGADMSIYFPYTEKEKRLTNE

HPEIEELLYSPVENKDHLCVLKDQNKPILFTMARLDRVKNLTGLVEWYAKNARLRELVNLVVVGGDRRKESKDLEEQ

AEMKKMYDLIETYNLNGQFRWISSQMNRVRNGELYRYIADTRGAFVQPAFYEAFGLTVVESMTCGLPTFATCNGGPF

-continued

EIIVNGKSGFHIDPNQGDKAADMLVNFFEKSKEDPSYWDTISKGGLQRILEKYTWQIYSQKVITLSGIYGENKYATK

NDKVASAKKRYLEMEYEFGEKKSAEKVPLAIDE

SEQ ID NO: 5: Polynucleotide sequence of NtSUS2-2
atggctgaacgtgctctgactcgtgttcacagccttcgtgaacgtcttgatgccactttggctgcacatcgcaatga gatattgctgtttctttcaaggtattgcctaagtagtgttcttgtttcctacaaaagattcagttggtgttcaaaaa acgatatgtgatttgatttatctgcctaagtcttggtagtcataattatccggtacctgtgctggtgcgagttagct ggttcggaaactactcttatgaaaacgagagatttagttggtgttgtctgcaattctgtagtatggactattaagca gatagatcatgtttgatatcgaaaaggaatgtatatgtgatgttacttgaactggttttggttattacaggattgaa agccatggaaaagggatcttgaaacctcaccagctattggctgagttcgatgcaattcgccaagatgacaaaaagaa gctgaatgatcatgcatttgaagaactcctgaaatctactcaggtaattttgattttggctaaatgtgttaccaagc tgaatgatcatgcatttgagtttgtgtccgactactacaatgatatgttataccaggaagcgattgttctgccacct tgggttgcacttgccattcgtttgaggcctggtgtgtgggaatatgtccgtgtgaatgttaatgctctagtcgttga ggagctgaccgtccctgagtatttgcattttaaggaagaacttgttgatggaacgtaagttttagtctcttatttga tactatgttagagaataggcagtggattcaatttatcagtgttgtttttacctaatgcagctccaatggaaatttc gttctcgagttggattttgagcccttcactgcatcctttcctaaaccgaccctcaccaaatctattgggaatggagt tgaattcctcaataggcacctttctgcgaaaatgttccatgacaaggaaagcatgaccccgcttcttgaatttcttc gggttcacaattataagggcaaggtaactttgttattcccattcatatatatgttcagtttgtgcttatcatgcgcc caatgatgtatgaatatgtactaaaggatagatgtacgatttcgtttgcagacaatgatgctgaatgacagaataca gaatttaaccactctgcaaaatgtcctaaggaaggcagaggaataccttattatgcttccccctgaaactccatttt ccgaattcgaacacaagttccaagaaattggattggagaagggatggggcgacactgcggagcgcgtgctagagatg atatgcatgcttcttgatctacttgaggctcccgactcctgtactcttgagaagttcctagggagaattcctatggt gttcaacgtggttatcctttccccccatggatatttcgcccaggaaaatgtcttgggttatcccgacactggtggcc aggtgcattactttagtctttgtccgtgagtctatgttgctcagatcctctacaatgccactgtacccgtgtaggat actccaaatataatgcattttggaggatctgtcaccggtgcaatggcattttggaggtcggagcaacaaacaactg ctagtatgcttctaaagcttgcttccataaatgctaaggtccttcacccgtaatgtgcaggttgtctacatattaga tcaagttccagccttggagcgtgaaatgcttaaacgcctaaaggagcaaggacttgatataacaccgcgtattctta ttgttagtatttcttgtacttgtaattgctgcggattacacaaaattttctctttattggcaacttatcttgatatt attcccaggttactcgtctgctgcctgatgcagttggaacaacttgtggtcagcggcttgagaaggtgtatggagcc gagcactcacatattcttagggtcccctttaggaccgagaagggcattgttcgcaaatggatatctcgctttgaagt gtggccatacatggagactttcactgaggtgacactaagcttccttgtatttgtctatcttctaattggtattagga acaatttgctaattattaacgctttggcttttcgtacatcaggatgttgcaaaagaacttgctgcagaactgcaggc caagccagatttgataattggcaactatagcgagggaaatcttgtggcttcattgctggctcacaagttaggcgtaa cgcaggtctgtgttatttttcacctcttataaatctgattgtatttccattagtctggaactaaaagtactaaaatt ttcttttcttcgctgtgttatttgccttctgcagtgcaccattgcccatgcattggagaaaacaaagtatcctgatt ctgacatctactggaaaaaatttgacgaaaaataccatttctcgtcccagtttaccgctgatcttattgcaatgaat cacaccgattttatcatcaccagcactttccaggagatagcaggaaggtataacatcaattgctaattcggttgcag taacattttgttcgatttcttccccttatgcttaacctaataccctaatgaattttccagcaaggacactgtcggac agtacgagagtcaccaggcattcacaatgcctggattgtacagagtcgttcacggcattgatgtgttcgatcccaaa ttcaacattgtctcacctggagctgatataaacctgtatttcccatattccgagaaggaaaagagattgacagcact tcacccagaaattgaggagcttctgtacagtgatgttgagaacgaggaacatctgtaagtttctaacttactcgtac cgtcagtggcagagccagaattttcattaaaatggggtcaaaatataaagacataaattcacaaagaagccaagggg -continued tgtcaatatgtagtataaatatattaaaaaaattacctagctacacaatgtaattttccgacaaaggggtatcggtt gcacttcttgaatacatgtggctctgccactgggtacagttacaaagtcctgttacctatgtagatgagcttgtgct gaacatgttgtgattttggtaggtgtgtgctaaaggacaggaataagccaatcttattcacaatggcgagattggat cgtgtgaagaacttaaccggacttgttgagtggtacgccaagaacgcacggctaagggagttggttaaccttgttgt cgttggtggagaccgaaggaaggaatccaaagatttggaagagcaagcagagatgaagaagatgtatgagctaataa agactcacaacttaaatggccaattcagatggatttcttcacagatgaaccgagtaaggaacggcgaactctaccga tacattgccgacactaggggagctttcgtgcagcctgcattctatgaggctttcggtttgactgttgttgaggccat gacctgtggtttgcctacatttgcaactaatcatggcggtccagctgagatcatcgttaacggaaaatccggcttcc atatcgatccatatcacggtgagcaagctgctgatctgctagctgatttctttgagaaatgtaagacggaaccttct cattgggaaactatttcaaccggtggcctgaagcgcatccaagagaagtaagcaactctttcttgactctagtcatt caaattaacttgggatttgaggcatagttgattgataatttatcgcgtctctactactatatacaggtacacgtggc aaatctactcggagagattattgacgttggctgctgtttacggtttctggaaacatgtttctaagcttgatcgtcta gaaatccgtcgatatctagaaatgttttatgctctcaaataccggaagatggtgagttcttctgcttcctgctcttc tcatagtgtttaatatacacttgattgattgcattcacttagactaagttgctcggacacgggtgtggatgtccgac acgagtgcggatctagagttcagatccttcaagatgtaaattataagattcggggatatggatcctagtacggatac gggtgcgagaatccggctaaaaataattttaaaaaaaattatctctaaattatgagatattatgtggaatacttacg tataacttgtaaagtgtagattttttttaattctcaagttgtagattagtaaatgattgatttcctagataagtatg ctattttcttcaaatttactcttctgatttcgaaaatcaaattgtatctcgtctcgaatttttccgtccgttatggt caaagtacccaaaatcgtttgaccaaatcggtacggatcccatacccacacccacactagtgtcgtattgacacggg tgccgcacctaaactgctatgtcggagcaacttagcacttagagaatcattgatgttaaattttcttaattcttgaa tctgctaatgaagattttatcttggtttttgtttaggctgaagctgttccattggctgctgaatga SEQ ID NO: 6: Polypeptide sequence of NtSUS2-2
MAERALTRVHSLRERLDATLAAHRNEILLFLSRIESHGKGILKPHQLLAEFDAIRQDDKKKLNDHAFEELLKSTQEA

IVLPPWVALAIRLRPGVWEYVRVNVNALVVEELTVPEYLHEKEELVDGTSNGNEVLELDFEPFTASFPKPTLTKSIG

NGVEFLNRHLSAKMFHDKESMTPLLEFLRVHNYKGKTMMLNDRIQNLTTLQNVLRKAEEYLIMLPPETPFSEFEHKF

QEIGLEKGWGDTAERVLEMICMLLDLLEAPDSCTLEKFLGRIPMVFNVVILSPHGYFAQENVLGYPDTGGQVVYILD

QVPALEREMLKRLKEQGLDITPRILIVTRLLPDAVGTTCGQRLEKVYGAEHSHILRVPFRTEKGIVRKWISRFEVWP

YMETFTEDVAKELAAELQAKPDLIIGNYSEGNLVASLLAHKLGVTQCTIAHALEKTKYPDSDIYWKKEDEKYHFSSQ

FTADLIAMNHTDFIITSTFQEIAGSKDTVGQYESHQAFTMPGLYRVVHGIDVFDPKENIVSPGADINLYFPYSEKEK

RLTALHPEIEELLYSDVENEEHLCVLKDRNKPILFTMARLDRVKNLTGLVEWYAKNARLRELVNLVVVGGDRRKESK

DLEEQAEMKKMYELIKTHNLNGQFRWISSQMNRVRNGELYRYIADTRGAFVQPAFYEAFGLTVVEAMTCGLPTFATN

HGGPAEIIVNGKSGFHIDPYHGEQAADLLADFFEKCKTEPSHWETISTGGLKRIQEKYTWQIYSERLLTLAAVYGFW

KHVSKLDRLEIRRYLEMFYALKYRKMAEAVPLAAE

SEQ ID NO: 7: Polynucleotide sequence of NtSUS2-T
atgctttttatgggagtaaattttatggccggtcattcaactttgtgttcattacgcaaaagtcatttttcttggtg tttattacgcaagtcatttttctttttttttgttacgtaaaaatcattcaactatgtgtttattatctaaaattca attttttttttcctttttgttacacaaaaatcattttactttactctatttatcacaaaagtcaccttggccagattt tataataggcttttatcttttgttacacaaaaattattttactttactctatttatcacaaaagtcaccttggccag attttataataggcttttatcttttgttacacaaaaattattttactttactctatttatcacaaaagtcaccttgg ccagattttacaatacttttaccttaaaagactattatgcccttgacattataaatcctctcatttatataatacct tctatatgatacactatataatatatttttacctaggtattttacttataattaaaataatattaaattattttatt -continued

```
tatctattttataatatattcatacatttaatttttcatggcaaatcactttgtttaatcatatttaaacatgaac

aaattttaaatatcaaaaaaataaaaaaataaaaaaaatatttatttgaaataataacaaacagatttgtttaacaa

atgatagtttttttttatagtcaataaaatttttaaaaaaattcaaagatatttgtttttaatattaatatttttaa

agctttatctgttaatattatttatttgaaagtattaatctgatgtgtcattgtgttaaatgtgagtattttattta

ttggattaatgagtatggcttggctgataaaaagctttgattttataattttcattaaaaatattttattaagctag

tacctgacaaatttaatatcttgaaaattaacgttaagaaaaaattaaatataaaaatatattataaaaataataaa

taaataatatcaagttattttaattataaataaaatacatggttaaaaatatattatatagcatataatatagaagg

tattacataaatgagatgatttaaagggcataatagacttttcaggtgaatgatttgtaaaatatggttaaagtgat

tattgtgataattagagcatagtaaaataatttttatgtaacaaaagaaaaaaaaaatgacttttgggtaatgaaca

taaatttgaataacttttacgtaacaaaagaataaaataaattttggataataaacataaaattgaatgaccaccta

taaaatttattatttttttgggctcttcttgatttgatttttttagtttagcctttgcagtaatcttggttgtcacgc

gtagcgttgtgctttcgccacataagtatttagtagacttaattaatgtcattatatcggttggtgtggttttaatt

acttaactgtactattatattaggtggaaggtttgaaaatttatagtagtaacattctagatcattgaaaatattgg

tgtttcagtgactttttagtatgtcattttcattttctaagtggttgtactaatatagtatattaaaattttgattg

gttgagaaacaatctctctcacctacacggtacgggtaaggtatgcgtatacgcttatcctccctacactccatttg

tgggactattgttgttattttggataagctgaggtatccatcttctactaactgcactagtttatttttttttgctgt

ttacagttgaaacaattgtctgaggatttctcacctgctgaatcaactgcaatggctgaacgtgtgctgactcgtgt

tcacagccttcgtgaacgtcttgatgctactttggctgctcatcgcaatgagatattactgtttctttcaaggtata

gccaaagatagtattcttgttaactaaaaaagattcagttggtgttcaaaaaacgatacgtttatctgcctaagtct

tggtagtcagaattatccggtacctatgctggtgtgagttagctggctaggaaaccactcttatgaaaacaagagat

ttagttagagttgtctgtaattctgtagtatggactatgtatgtgatgctatttgaactggttttggttattatagg

attgaaagccatggaaaagggatcttgaaaccgcatcagctattggctgagtttgatgcaattcgccaagatgacaa

aaagaaactgaatgatcatgcatttgaagaactcctgaagtccactcaggtaatatggttttggctatatttgtcgc

caacgccaagctcatatttttatattattttgagcttgtgtctgaatacgacgatgatatgttatactaggaagcaa

ttgttctgccaccttgggttgcacttgcgattcgtttgaggcctggtgtgtgggaatatgtccgtgtgaatgtcaat

gcgctagtcgttgaggagctgactgtccctgagtatttgcatttcaaggaagaacttgtcgatggaacgtaagtgtt

agtcttcaatttgatgctatgttagagaataggctgtggaatttattgatcaatgctgtgctttgtcctgatacagc

tccaatggaaatttcgttctcgagttggattttgagcccttcaccgcatcctttcctaaaccaaccctcaccaaatc

tatcggaaatggagttgaattcctcaataggcacctctctgcgaaaatgttccatgacaaggaaagcatgaccccgc

ttcttgaatttcttcgggttcacaattataagggcaaggtgacttgctatttccatttatctataggttcggtttgt

gcttatcatgcgcccaatgacatatgaatatgcgctaaaggatagatatatgatttcctttgcagacaatgatgctg

aacgacagaatacagaatttaaccacactgcaaaatgtcctaaggaaggcagaggaatacctcattatgcttccccc

tgaaactccattttccgaattcgaacacaagttccaagaaattggattggagaagggatggggcgacactgcagagc

gcgtgctggagatgatatgcatgcttcttgatctcctcgaggctcccgattcctgtactcttgagaagttcttgggg

agaattcctatggtgttcaatgtggttatcctttccccccacggatatttcgcccaggaaaatgtcttgggttatcc

cgacactggtggccaggtgcattactttaatctttatccgtgagtctatgtttgttcgaatcctctagaaatgtcac

tgtacctatgtaggatactccaaatataatgcatttgggggatctgttatgggtgcgatggcatttttggaggtc

ggagcaacaaacaattgctatgtattcttctaaagcttgctttcataaatgctaaggtccttcacccttaatgtgca

ggttgtctatatattagatcaagttccagccttggagcgtgaaatgcttaagcgcctaaaggagcaaggacttgata

tcacaccgcgtattcttattgttagtatttcctgtacttgtaattactgcggattacacaaaatttcctttttatct

tcttaacaacttatcttgatggtattcccaggttactcgtctgctacctgatgcagttggaacgacttgtggtcagc
```

-continued ggcttgagaaggtgtatggagccgagcactcacatattctgagggtcccctttaggactgagaagggcattgttcgt aaatggatctctcgctttgaagtgtggccatatatggagactttcactgaggtgacactaaaacttccttatatttg tctatcttctaattggtattaggaataatttgttaattgttaactctttgtcttttcgtacatcaggatgtcgcaaa agaacttgctgcagaattgcaggccaagccagatttgataataggcaactatagcgagggaaatcttgtggcttcat tgctcgctcataagttaggcgtaacacaggtctgtgttgtttttcactctcttaaagatctgattgcatttccatta gtctggaactagaagtactaaaaagttcttttcttcactgtgttatttgccgtcggcagtgcaccatagctcatgca ttggagaaaacaaagtatcctgattctgacatctactggaaaaaattcgatgaaaaataccatttctcgtcccagtt taccgctgatcttattgcaatgaatcacaccgattttatcatcaccagcactttccaggagatagcaggaaggtata acatcaatttgctacttcgactgcaacagcattgtgttcccatttctttcccttatgcttaacctaataccgtcatg aattttccagcaaggacactgtcggacagtacgagagtcatcaggcattcacaatgcccggattgtacagagttgtt cacggcattgatgtgttcgaccccaaattcaacattgtctcacctggagctgacataaacctctatttcccatattc cgagaaggaaaagagactgacagcacttcaccctgaaatcgaggagctgctgtacagtgacattgagaacgaggaac atctgtaagtttctaccttactcgtacagtcagtggcggagccagaattttcactaaaataaggtcaaaatataaag acataaatccacaaagaagccaagggtgtcaatatatagtataaatacattaaaaaaattacctatctacacagtgt aattttccgacaaaggggtgtcggttgacactccttgaatacatgtggctctgccactgggtacagttacaaagttc tgttacctatgtagatgagcttgtgctgaacatgttgtgattttggcaggtgtgtgctaaaggacaggaataagcca atcttattcacaatggcgagattggatcgtgtgaagaatttaaccggacttgttgagtggtatgccaagaacgcacg gctaagggagttggttaaccttgttgtggttggtggagatcgaaggaaagaatccaaagatttggaagagcaaacag aaatgaaaaagatgtatgagctaataaagactcacaatttaaatggccaattcagatggatttcttcacagatgaac cgagtgaggaacggtgaactctaccgatacattgctgacactagaggagctttcgtgcagcctgcattctacgaggc tttcggtttgactgttgttgaggccatgacctgtggtttgcctacatttgcaactaatcatggcggtccagctgaga tcatcgttaacggaaaatctggcttccacatcgatccatatcacggtgagcaagctgctgatctgctagctgatttc tttgagaaatgtaagacagaaccttctcattgggaaaccatttcaacgggtggcctgaagcgcatccaagagaagta agcaactctttcttgactctagtcattgaaattaactttcttgactctagtcattgaaattaactcgggatttgagg cgtagttgattgatattttatcgcgtctctactactgatatatacaggtacacgtggcaaatctactcggagaggct attgacattggctgctgtttacgggttctggaaacatgtttctaagcttgatcgtctagaaatccgtcgatatcttg aaatgttttatgctctcaaataccgcaagatggtgagttcctcttcttccttgcccttctcctagtgtttaagatac aatataattgattgcattatcttagagaatcattaatgttaaattttcttaattcttgaatctgttaatgaagtttt tctcttggtttttgtttaggctgaagctgttccattggctgctgagtga SEQ ID NO: 8: Polypeptide sequence of NtSUS2-T

MLFMGLKQLSEDFSPAESTAMAERVLTRVHSLRERLDATLAAHRNEILLELSRIESHGKGILKPHQLLAEFDAIRQD

DKKKLNDHAFEELLKSTQEATVLPPWVALAIRLRPGVWEYVRVNVNALVVEELTVPEYLHFKEELVDGTSNGNEVLE

LDFEPFTASFPKPTLTKSIGNGVEFLNRHLSAKMFHDKESMTPLLEFLRVHNYKGKTMMLNDRIQNLTTLQNVLRKA

EEYLIMLPPETPFSEFEHKFQEIGLEKGWGDTAERVLEMICMLLDLLEAPDSCTLEKFLGRIPMVFNVVILSPHGYF

AQENVLGYPDTGGQVVYILDQVPALEREMLKRLKEQGLDITPRILIVTRLLPDAVGTTCGQRLEKVYGAEHSHILRV

PFRTEKGIVRKWISRFEVWPYMETFTEDVAKELAAELQAKPDLIIGNYSEGNLVASLLAHKLGVTQCTIAHALEKTK

YPDSDIYWKKEDEKYHESSQFTADLIAMNHTDFIITSTFQEIAGSKDTVGQYESHQAFTMPGLYRVVHGIDVFDPKF

NIVSPGADINLYFPYSEKEKRLTALHPEIEELLYSDIENEEHLCVLKDRNKPILFTMARLDRVKNLTGLVEWYAKNA

RLRELVNLVVVGGDRRKESKDLEEQTEMKKMYELIKTHNLNGQFRWISSQMNRVRNGELYRYIADTRGAFVQPAFYE

AFGLTVVEAMTCGLPTFATNHGGPAEIIVNGKSGFHIDPYHGEQAADLLADFFEKCKTEPSHWETISTGGLKRIQEK

YTWQIYSERLLTLAAVYGEWKHVSKLDRLEIRRYLEMFYALKYRKMAEAVPLAAE

-continued

SEQ ID NO: 9: Polynucleotide sequence of NtSUS3-S atggcgaatccaaagttcacaagagtacctagcatgagggagagagttgaggatactctctctgctcaccgtaacca gcttgttgctctcctctccaggtatattaataaactctatatacttgttatttctttattttttgtctttactga taaatttaactgttttcttctttaaatcttgctttcgatgcatgatttctgttgtgttaaattgcgtaaccatttta tctaaaagtttatgctgataaacacttttaaattttaatatgtaaattatattatgtctcaacatcaacatgtggat ggccaaaaatataaagcttaattttcgttattttgaatgatttttctctgcgagtgttacggtttgcgtacacatta cctaaacctcctccctagtccccacttgtgggaatttaattttttttttctttgttttttttttgttgttgttgttgt ctgagttcaattcctaccatgttagcttggcaaaaataagttggtaaagcttgaccccaactagttttagttgatcg atttatttggtgatttatagttcaataataataattactattagagaaagttccagcagcttttctgtttgtttttc cagttttagtgattgatatatgtgtatatatattctttgtttcttttaagatacgtggcgcaggggaaggggatatt gcaacctcaccacttgatcgatgagttcaacaacgctgtatgtgatgacactgcttgtgagaagctcaaagatggtc cctttagtgaagtcttgaaagctactcaggtatattcactaatccatgggaatcaagatgatactgtatatctttat tatggtgtctttcagaaatttgacgatgatgaaatgcaacttttctctgtttgtcaccttatccagactgtttttt attttttattttttcatttttttaacttgaaatgctcttaatttcctttgtttatcgataagaccggatttacaatgta tgaacggagcatcttaagaaccttctggaatgaagatataagatataaaacatggtgtccgttttctcctttgtgga atcagtgtacatatagactgttattttggtcccactttctggatcttctgatcacaccttctcatgcagaggcgagc ttgatggtttcaacctttaaattcttactattgaatccatttcactttcgaaattatgagttcgaaatctaatattt gttgaaattttttgcaaatgttcacatataagtttaagctttgtgtcaagaatactgggctcaatggattccaataga ccaggctgtatccgcctctgtctccactctccctgcatccacttctttcgtgtgactaataatgcttaatgagctag aactcgttttaatgtttgaataagttgcttatatcagagcagcttttgatgtttcaatctttaacgggttatgcagt accagcattctgcggctgaaaaacaggaatctgagatttacttgtctctggctgaatttcttgttcattttgctaac aagtactttggagttaatgcttgctctctgttgtcaaaataggaagccattgtgctgccaccatttgttgccatagc agttcgtccaaggccaggtgtttgggagtatgttcgtgttaatgtatatgatttgagcgttgaacaattgactgttc ctgaatatcttcatttcaaggaagaacttgtggatggagagtaagctctttcttatttcaatacgaaacataaaaat ttacagaagttgaataattaacaaatttgttgattttaatgtatgccaggggtaataatcactttgtgcttgagct ggattttgagccatttaatgcatcagttcctcgtccatctcgatcgtcatccattggcaatggagtccaattcctca atcgtcatctttcctcaattatgtttcgcagcaaagactctctggaccccttacttgatttccttagaggacactgt cataaagggaatgtaagtaccaaaagcagttttccctttgtaaatgtctgcttgtccctgattatctactaaatctt tcaacacgcgcaaccattataagaaatgtacaatacttctagttagaatttcatcatcgacaaactatctgctttac tttttattttttcccatttgatggatgatagtttagtttatataacagatgatattttggttgaagggtaccatgaac tttttcacaaccacttaatggatacatagttgtaatagttgacattttggaataatattgtctcacttggaaatgtt taagaagtattactacttctatttgtaagatggattgtttatctatgcaggtcttgatgttgaatgatcgtatacag cgaatctccaggctggagtctgctctttctaaagcagaggattatctctccaagctatcaccagatacatcctataa tgagttcgaatacgcgtgagcttgtacacatttgttttgttttctttcaagcatatgtaatttctcaagaaaaggga aatctataggagttgaaacattctttatggaaccatgtgcatgcagattgcaagaaatgggctttgagagaggttgg ggtgatactgccagacgtgttttggagacgatgcatcttctttctgacattcttcaggctccggatccatcaacctt ggagacatttcttggtagactacctatggtgttcaatgtcgtcatattatcccctcatggatattttggccaagcaa atgtcttgggtttgcccgacactggtggccaggtaataacaaggagaatgaggtcttgtattatgtactccctccgt tccaatctatatgaacctatttgactgggtatggaaagaaatgaagacttgtaaaacttgtggttctttagaaattc caaacattacatttggtttttttccctcttcctggaaattatactactgaatcatctctagatgttccagtttaactt gagacgtaagggtaaataacggaccattactctgtcctttcttgcagtaggcttggtacaatgaatatagttcgcat -continued agttgccggaagctagagctgtgttagaaaactcaggaacattaatttggcgatgctaatcactgctaatgttactg aagcatccatggttttccttgatgttattctccttttggttgcttcacaggttgtctatatactggatcaagtgcgt gccttggaggccgaaatgcttcttagaataaagcaacaaggacttaacttcaagcctagaatccttgtcgtgagtac atatatattatgcaagctcttatttggtttgtgggattgcagttgacatcaatttgcttactctgattactaaaggt cacacggctgatacctgatgctaaaggaaccatgtgcaaccagaggttggagaggattagtggaactgaatactcgc atattttacgtgtcccttttaggacagagaagggaatccttcataaatggatatctaggtttgatgtatggccttac ctggagaagttcactgaggtaacctctttgtcccttggaaattgccttttgttgctgatgtttctgctagtgtgctt aaatgacggatgttaactagtcacttgctagcgtttgcaatagcaacgggaaaagaaaggatttttgctagtttgaa gtctgcctccaagaaaaattatattaaaagtttatggctagtggaaacatcagtcattcatgtaccttatttctatg cccaagttgtttaagttgaaagtaatttggccaactatgcaaattgggagaacgtgtagccaactattgtgtttgcc gacatgttgatatactttttggtcctgatttatatttgttggtttgtcatactggatgaagcaattctcatgttttt ctgcttatatatattggaagaagagatacttgtcgtttcatcatttttctcgacctctctattaccaacactttgcc aatttaatgtttggaaatgtcttcttgaccaggatgtggcaagtgaaatgaccgctgagctccagggaaagccagat ctgattattggcaactacagtgatggaaatttagttgcctcccttttggcatataaaatgggtgtcacacaggtagg aaatacatgattctttatcttgctagcactaagtcttgaggttatgtatctgcaatagaaattttacgctttgcctt catttctttttaattatttttccagtgtaccattgctcatgccttggaaaaaacaaagtatcctgattctgacatct actggaaaaagtttgaggagaaatatcatttttcatgtcagtttactgctgatctactggcaatgaataattcagat ttcattatcaccagtacttatcaagagattgcaggaacgtaagtcattttaatctggtcgtttaaatctgatatttc ttccctagtagtctattcaatccgaatttcagttcagtatatgatgtcatcggttgaggaactgtgattggtaacct tatcaaatccgtagctgctctataattttatttcgtaattggagaaacaatttttattattgagcttgtagtctga gctagaatttggttctttatctatcaagtagcataatactacaactatttttatgtgtggcaatttgcaatttcaa ttttctatttctataagttgcagcttttcttcctgttctgatcatatttacatggctgaaactcaatagaaaactag gctagttgatcaaaagtagttggatgctttaaaattagtagacgttttgctaaatgagtgaccaatgttattaaaaa aacgttcatgttttcaacccttttggcatacatttgaccactgcccaagattttggataagtacatgcagtgcttat aattataaagcattttatcccaccttgtttttcattatgaaaattaagtaatttacgagtatttgtataagttactt cataaattagaagtaaatctggattgtgtaaagttattcgccccgtatatactgaaagctacttgaacaagcaaaaa aacagacaaacgtaacattctccatggattaatgagacttgtatatatatatatatatatgtaaagagagagaga gagagatttggcttgtaaccacatgtatattatgccatatggatgtgacattgatgtgactagacctaaatgttttg tttcaatgtccacgggagttttacgtagagttaagaggagaagagagtgaggaatactaatgtttgatggtacccct tggcttcttgacctggatactcagtgttcttattcatgcctatactttggtccttgatttcattctcccttttctag cttgagctgcatcaaagaaattccactgtaaaaaaaataatgctcaccatattggtgcaacatggcaaacatgtatc ctatttgatgatcaatcaactttatttttctcctgttaattgacctcagtgtgtaactctctatgtatgatagcatt gtaacttgtgtcatgattcataaatagggtactagaattggatggttgacatagtaaatggtcaattgatgatccac aaaatatgcacctactgattaaaatgtgatagggcaggtttatttttgtttgtggttaacacagtacttaaccctat atttaatacaatttggcttatctacaatcttttcttcagtgtttatgcgaattccttattgcacaacaatattgtct ttctgagttctattctgttgttgcttacacttttattattccagtaacatagatgtgaagacattagattggttgct tgcaaattgatagccacttgtttcaggaagaatactgttggtcagtacgagagccatactgcattcaccctcccggg actatatcgcgtcgttcatggcattgatgttttcgatcccaaattcaatatagtgtctcctggagctgacatgacaa tttatttcccatattctgacaaggaaaaaagactaacgtctttgcatggctcgattgaaaagttgttatttgatcct gcgcagaatgaagagcatatgtaagtggcatccgtttgtacttaatttttttggaatagatgacatattatttgcat -continued

```
gaatatgaaaaggagggtctgatatgattttctatagataaactaccaatgatattatttaaaaactcctggatact
gtattaggagaagaagagaaccaggggtagatggcattagaatcccttaaatcttgaagagtcgtcactaacgctcc
caacacttctgcctcagaccctcaactaaatactattattgttgatttctttggagaagctataagaatctctctct
ccttatggtgaaaattttacttggctttatacttaacttccaaggctccctcttataaaatgcaaaaactgtctgta
ttcactctcttggttaacaattgatccaatcaaatgcatatggaacatctttctttacgtttcttctaaagttcgtt
tgaggataaggagtagaatctgagaagatagactagtaggtaaccttagggacggatgtggaaattaacatatgggc
tcagcttttctgccgagtgcagaccatgtatatgcgttaaaaaattcactaaacaagtaaatgtttgattttgaacc
cagtaaatcaaatgagttgtggtagaatctcgaactcgaaccgataaagttcaaatccaggatccgcttttaggtaa
actctaccttgggaagtgttatatatatgtccctgattatttctttttccgtttcctttctattttaatttttaaag
ttatttttagatggttttatttttgataagtggtaagttgttaatattccaaattaaatgccattgtcataactat
atacatttataaagaatgattgatcctagtttctcattcctaagatccaaataaggcaataaacaatgtcttagtaa
ttggacctgcttctggtgatcaacgcttgatcgcgtagttagttatagatgactgtaaaaactttaaccattttaat
ggttttgtcaaagaacaaatatcggacatattatagagaatggactattgtactttgcttctgattggtcattttat
tgtgatccgtaaattggctgtgactgatgtcatatctttgcttacagaggtaatctgaatgataaatcaaaacccat
aatttttttcaatggcaaggctagaccatgttaagaacattacgggactagttgagtgctatgctaaaaatgccacat
tgagggaattggcgaaccttgttgtagtagctggatacaacgatgtaaagaaatccagtgatagagaagaaataaca
gaaattgagaagatgcatgctcttattaaggagcataaattggatgggcaattcagatgggtatcagcccaaacaaa
ccgggcacgtaatggtgagctctatcgctatatagctgaccagagaggtatatttgttcaggtatgctatttgtatt
gtattagtccaatttcatttttttgcaccaaaagaaaggttgttattgtgacgtatatgtttgttttagcctgcattt
tatgaagcatttggactaacggtggttgaagctatgacttgtggtcttccaacatttgcaacttgccatggtggtcc
taatgagatcattgaacccggtgtatctgggttccatattgatccttatcatcccgataaagctgctgaactcatgt
cagaattctttcaacgctgcaaacaagatcctactcactgggaaaaaaatatctgcatctggtctccgaaggattctt
gagaggtctgtagttgtgtacatgtatagaagattaaagaatgctaccttgatatttatttgaatcaaaaataacag
gaacatctcttttttgaacatcactcaagttcttatattaaataatttttaggtatacgtggaagatttactccgag
aggctgatgactttatctggcgtatatggtttctggaagcttgtttcaaaacttgagaggcgtgaaactagacgata
ccttgagatgttctacattctcaaattccgcgagttggtgagtgccttttagctcctttttcagttccaataaactat
atatgtggtttaagtaagtattaagcataaacatgtccgtgcttggggctgtcgaaaatgctatggacatatcctga
gctaaggatttttcaagaaaattgatgttagctttactctatttacaggcaaaatctgtacctctagcaattgatga
caagtga
```

SEQ ID NO: 10: Polypeptide sequence of NtSUS3-S

```
MANPKFTRVPSMRERVEDTLSAHRNQLVALLSRYVAQGKGILQPHHLIDEFNNAVCDDTACEKLKDGPFSEVLKATQ
EAIVLPPFVAIAVRPRPGVWEYVRVNVYDLSVEQLTVPEYLHFKEELVDGEGNNHFVLELDFEPFNASVPRPSRSSS
IGNGVQFLNRHLSSIMFRSKDSLDPLLDFLRGHCHKGNVLMLNDRIQRISRLESALSKAEDYLSKLSPDTSYNEFEY
ALQEMGFERGWGDTARRVLETMHLLSDILQAPDPSTLETFLGRLPMVFNVVILSPHGYFGQANVLGLPDTGGQVVYI
LDQVRALEAEMLLRIKQQGLNFKPRILVVTRLIPDAKGTMCNQRLERISGTEYSHILRVPFRTEKGILHKWISRFDV
WPYLEKFTEDVASEMTAELQGKPDLIIGNYSDGNLVASLLAYKMGVTQCTIAHALEKTKYPDSDIYWKKFEEKYHFS
CQFTADLLAMNNSDFIITSTYQEIAGTKNTVGQYESHTAFTLPGLYRVVHGIDVFDPKFNIVSPGADMTIYFPYSDK
EKRLTSLHGSIEKLLFDPAQNEEHIGNLNDKSKPIIFSMARLDHVKNITGLVECYAKNATLRELANLVVVAGYNDVK
KSSDREEITEIEKMHALIKEHKLDGQFRWVSAQTNRARNGELYRYIADQRGIFVQPAFYEAFGLTVVEAMTCGLPTF
ATCHGGPNEIIEPGVSGFHIDPYHPDKAAELMSEFFQRCKQDPTHWEKISASGLRRILERYTWKIYSERLMTLSGVY
GFWKLVSKLERRETRRYLEMFYILKFRELAKSVPLAIDDK
```

-continued

SEQ ID NO: 11: Polynucleotide sequence of NtSUS3-T atgtttacatggctgaaactcaatataaaaaacaagggtaggtgatcaaaaatcgttggatgcttaaaatcagtaga cgttttgctaaatgagcgaccaatgttattgaaaacgttcatgttttcaacccttttggcatacatttgagcattgc ccaagattttggataagtagatgcagtgcttataattttaaagcattgtatcctgccttgtttttcattgtcaaaat taattaacttacaagtatttctataagttgcttcataaattagaagtaaatctggattgtgtaatgttattcgcctc gtaaatactgaaagctgcttgaacaagtgaaaaaacacagacaaacgtaacattctccatggattgatgagacttgt aaaatacatatatagaaatttggcttgtaaccacatgtatattatgccatatggatgtgacattgatgtgactagac ctaaatgttttgtttccatgtccactggagttttacgtatagttaagaggagaaaagactgaggaatactaatgtat gatggtacccctttgcttcttgacctggatacccagtgttcctattcatgcctatactttggtccttgatttcactc tccctttttctaacttgagctgcatcaaagaaatttccactgtaaaaaaataaataatgctcaccatatctctgcaac attgcaaacatgtatcccatatgattgatattggtgcgacatggcaaacatgtatcctatttgatgatcaatcaaat ttatttttcccctgtcaaaatgacctcagtgtgtaattccctatgtatttgatagcattgtaactcgtgtcatgatt catgaatagggtactagaattgcatggttgacaaatattaactggtcgattgatgatccacaaaacatgcacttact gactaaaatgtgatgggacagatttatttttgtttgtgattaacacagtacttaaccctatacttaatacaatttgg cctagctacaatcttttcttcagtgcaaattccttgttacacgaccaatattgtctttctgagttctattctgttgt tacttacacttttattattcgaataagacattagattgcttgcatgcaaattgatagccacttgtttcaggaagaat actgttggtcagtacgagagccatactgcattcaccctcccaggactatatcgcgtcgttcatggcattgatgtttt cgatcccaaattcaatatagtgtctcctggagctgacatgacaatttacttcccatattctgacaaggaaaaaagac taacgtctttgcatggctcgattgagaagttgttatttgatcctgcgcagaatgaagagcatatgtaagtgacatcc atttgtacttattttaatttggaatagatgacatacttatttgcatgaatataaactgacaacccagagatttccta cattagaaaaggagggtctgatatgattttctacaaataaattcccagtgatattgttcaaaaagtcctggatactt tattatgagagaaccagggatagatggcactagaatcccttaatcttgagaagtcgccacttatcgctcccaacact ttctgagaccctcaagtaactactattattgtttgatatcttggagaagctataagaatctttttctccttattgta atttttttacgtgactttaaacttaacttccaagctccttctgataaaatgcaaaaactgtctgtattcactgtct tggtttattaacaattgatccaatcaaatgcatatggaacatctttctttttgtttcttcaaaagttcgtttgagga taaggagtagaatctgagaagatagactagtaggtaaccttaggggcggatgtagaaatcaacgtatgggttcagct ttgttgcagaccctgtatatgcattaaaaaaatcactaaataagtaaataattgattttgaacccagtaaatcaaaa tgagttgtagtagaatcctgaactcgaaccgataaagttggatccactaccgggtaaactctaccttgagaagtgtt tatatatgtccctaattatttcttttctgtttcctttctatttaatttttaagttccttttttagatggttttatt ttttgacaagtggtaagttgttagtattccaaattaaatgccattgccataactatatacatttataaagattgatt gaccctagtttctcattcctaagatccaaataaggcaataaacaatatgtcttagtacttgaacctgcttctggtgg tcaacacttgatcgcgtagttagttatagatgactgtaaaaaccttaatcattttaatggttttgtcaaagaacaaa tatcggacatattatagcgaatggactattgtacttttcttctgattggtcattttattgtgatccgtaagttggct gagactgatgtcatatctttgcttacagaggtaatctgaatgataaatcaaaacccataatttttttcaatggcaagg ctagaccatgttaagaacattacgggactagttgagtgctatgctaaaaatgccacattgagggaattggctaacct tgttgttgtagctggatacaacgatgtaaagaaatccagtgatagagaagaaatagcagaaattgagaagatgcatg ctcttattaaggagcataaattggatgggcaattcagatggatagcagcccaaacaaaccgggcacgtaatggtgag ctctatcgctatatagctgacaagagaggtatatttgttcaggtacgctgtttgtattgtatttgtccacattcctt tttttgcaccgaaagaaaggttgttattgtgacaaatatgtttgttttagcctgcattttatgaagcatttggactc acggtggttgaagctatgacttgtggtcttccaacatttgcaacttgccatggtggtccgaacgagatcattgaaca cggtgtatctgggttccatattgatccttatcatcccgataaagctgctgaactcatggcagaattctttcaacgct -continued gcaaacaagatcctactcactgggaaaaaatatctgcatctggtctccgaaggattcttgagaggtttgtagttgtg tacatatatagaagattaaagattgttcccttgatattatttgaatgaaaaataacagtaacatctctttttgaaca tcgctcaagttcttgtgttaaataattgttaggtatacgtggaaaatttactccgagaggctgatgactttgtctgg tgtatatggtttctggaagcttgtttcaaaacttgagaggcgcgaaactagacgataccttgagatgttctacattc tcaaattccgcgagttggtgagtgcctttttgctcattttcagttacaatcaactatatatgtggtttaaatacgta ttaagcataaacatgtccgtgattgcggctgtcgaaaatgctatggacatatcctgagctaaggagttttcaagaga attgatttggcttactctgtttacaggcaaaatctgttcctctggcaattgatgacaagtga SEQ ID NO: 12: Polypeptide sequence of NtSUS3-T
MFTWLKLNIKNKGRKNTVGQYESHTAFTLPGLYRVVHGIDVFDPKFNIVSPGADMTIYFPYSDKEKRLTSLHGSIEK

LLFDPAQNEEHIGNLNDKSKPIIFSMARLDHVKNITGLVECYAKNATLRELANLVVVAGYNDVKKSSDREEIAEIEK

MHALIKEHKLDGQFRWIAAQTNRARNGELYRYIADKRGIFVQPAFYEAFGLTVVEAMTCGLPTFATCHGGPNEIIEH

GVSGFHIDPYHPDKAAELMAEFFQRCKQDPTHWEKISASGLRRILERYTWKIYSERLMTLSGVYGFWKLVSKLERRE

TRRYLEMFYILKFRELAKSVPLAIDDK

SEQ ID NO: 13: Polynucleotide sequence of NtSUS4-S
atggcggaacgtgtgctgactcgtgttcatagccttcgtgaacgtcttgatgctactttggctgctcatcgcaatga gattttgctgtttctttcaaggtatagtcttagcagattgttctttgatttagttgttattgccagttctaatgtat gggcttatatataaacaaagtgttgaagtatgcaaccatataaactgacagcttaaaatgcttgagagaacacactt ttatttatttaattatgccttcagcacaagaagtggaacttgacgcaatggaaccataggtcacgggttcaagtctt ggaacagcctgcaatctaaggctgcgtgtagtagaccctagtggtccggcccttccacatatctcgcttagtgtacc gggcccattgagtacgggttcggccgaacccagtcgctttggtccaatccatatatttgtcttaaaaatatattgaa tatatacaaattgttaatttagtttaaatatgtgtatcatgggttattcatgctggttttggctgttgcaggattga aagccatggaaaagggatactgaaacctcaccagttgctggctgaatttgattcaattcacaaagaagacaaaaaca aactgaatgatcatgcttttgaagaagtcctgaaatccactcaggtatttgtggttttagtgttaggtgatggatag catttattgttttactaagatcacatatgtgtcagtttgtggctagtatttaaaatctggtgtattttgtcatacta ggaagcaattgttttgtccccttgggttgcgcttgccattcgtctgaggcctggtgtgtgggaatacgttcgtgtga atgtcaacgctcttgttgttgaggagcttaccgtgcctgagtatttgcaattcaaggaagaacttgttaatggaacg taagttttaggttcgaatttgttgatttgttagataacatgttctgaactttttgattaaagttgtgtttttgactg atgcagctcgcacgataactttgttcttgagttggattttgagcccttcactgcatcatttccaaaaccaaccctca ccaaatcaattggaaatggagttgaattccttaaccgacacctctctgccaaaatgttccatgacaaggaaagcatg acccctcttctcgagtttcttcgagttcaccactacaagggcaaggtaaacttgtttttcctgtttgtctatgaatt tagtttagttgttttgctccgcgaaaatttcagtggaaactgatttatgcaaccactgagtgattaatatgttcaaa cttaccgacttctggttttctgtgtagacaatgatgctgaatgacagaattcaggacttaaatactctccaaaatgt cctaaggaaagctgaggaatacctcactaccctttcccctgaaacttcatactcggcatttgagcacaagttccaag aaattggcttggagaggggttggggtgacactgcggagcgtgttctagagatgatctgcatgctcctggatctcctc gaggctcctgactcgtgcacgcttgagaagttccttggtagaattccaatggtttttaatgtggtcatactttcacc ccatggttatttcgcccaggaaaatgtcttgggttaccccgacactggtggccaggtgcactgcttatctgtgttcg gtcttattatctctttaaaccctactgccacaagtgctgagatgaacctcctttaatttgcaggttgtctatatttt ggatcaagttcctgctttggagcgtgagatgctcaagcgcataaaggagcaaggacttgacatcaaaccgcgtattc ttattgttcgtattcccagtaattgtgtttaaacttatgattatgcaggattttatctgttctaatacagcactctt gcttaaattctcaggttactcggctgctgcctgatgcggttggtaccacttgtggtcagaggcttgagaaagtgttt ggaacagagcactcacacattcttagggtcccctttaggaccgagaagggcattgttcgcaaatggatctctcgctt tgaagtctggccatacatggagacattcactgaggtgaagcaagctttctctattcatttttcaatcttccaattgg -continued ttttggcagcaattttctgcttgctttgacttccgctaaaacttcggattttattgcattaggatgtggcgaaagaa attgctgcagaattgcaggctaagccagatcttatcattggcaattatagtgagggcaaccttgctgcctccttgtt ggctcacaaattaggtgtaacacaggtcggcaatgtttgtgacatgtaatttcatctttgcatttcctttcgtttgc aactaaaagatttaagagttctctctctcttttttttttccgtctactttgccttatgcagtgcacgatagctcatg ctttggagaaaacaaaatatcctgattctgatatctacttgaagaaatttgatgaaaaataccatttctcagcccag tttactgccgatcttattgcaatgaatcacaccgatttcatcatcaccagcactttccaggagatagcgggaaggta tttttacatcagtttcccactctgattaaattacaatgtatttccctatatgattaaatactgtgtttgatcctaaa tcatttctaaattttccagcaaggacactgttggacagtacgagagccacatggcgttcacaatgcctggactgtat agagttgttcacggcattgatgtgtttgaccccaaatttaacattgtgtcaccaggagctgatatgaatctctattt cccatactacgagaaggaaaagagattgacagcatatcaccctgaaattgaggagctgctgtttagtgatgttgaga atgacgaacacatgtatgttactaaactagcaatcctgctgcaaaattatggctaattatgtaaacaagtttgtact gaatagatttgttattcgatcaggtgtgtgctgaagaacaggaataagcctatcatattcactatggctagattgga tcgagtgaagaacttaactggacttgtcgagctgtacgccaagaacccacggctaagggagttggttaaccttgtcg tggttggaggagaccgaaggaaagaatccaaagacttggaagaacaggcagagatgaagaagatgtacgaacttata aagactcacaatttgaacggccaattccgatggatttcttcccagatgaaccgcgtgaggaatggcgaactctacag gtacattgccgatactaggggagctttcgtgcagcctgcattttacgaggcttttggtttgactgttgttgaggcca tgacctgtggtttgcctacatttgcaactaatcacggtggtccagctgagatcatcgttcacgggaaatctggtttc cacattgatccataccacggggatcaggcagctgaacttctcgctgatttctttgagaaatgtaagaaagaaccttc gcactgggaagccatttccgagggcggccttaagcgtatacaggagaagtaagcaaactgctactcttttcatttttt gcaaaacctactatgatcattattaagctcatttttgcaaaacctacttgctgttgttattgtttgttgcttccttt tcactgttctttgagctgaaggtctatcagaaacagtctctctaccttcacaaggtaggggtaagatctgcgtgcac gttaccctcctcaaactctacttaattgtgagattacactaggtttgttgttgttgattctttgctaattaattaaa aggtacacatggcaaatatactcggatcggttgttgacactggctgctgtatatggattctggaagcatgtttccaa gcttgatcgtcttgaaattcgccgttatcttgaaatgttctatgctctcaaattccgcaagctggtgagtttcattg ctttctgcactcctgcaattgtatag SEQ ID NO: 14: Polypeptide sequence of NtSUS4-S
MAERVLTRVHSLRERLDATLAAHRNEILLELSRIESHGKGILKPHQLLAEFDSIHKEDKNKLNDHAFEEVLKSTQEA

IVLSPWVALAIRLRPGVWEYVRVNVNALVVEELTVPEYLQFKEELVNGTSHDNEVLELDFEPFTASFPKPTLTKSIG

NGVEFLNRHLSAKMFHDKESMTPLLEFLRVHHYKGKTMMLNDRIQDLNTLQNVLRKAEEYLTTLSPETSYSAFEHKF

QEIGLERGWGDTAERVLEMICMLLDLLEAPDSCTLEKFLGRIPMVFNVVILSPHGYFAQENVLGYPDTGGQVVYILD

QVPALEREMLKRIKEQGLDIKPRILIVTRLLPDAVGTTCGQRLEKVFGTEHSHILRVPFRTEKGIVRKWISRFEVWP

YMETFTEDVAKEIAAELQAKPDLIIGNYSEGNLAASLLAHKLGVTQCTIAHALEKTKYPDSDIYLKKEDEKYHFSAQ

FTADLIAMNHTDFIITSTFQEIAGSKDTVGQYESHMAFTMPGLYRVVHGIDVFDPKFNIVSPGADMNLYFPYYEKEK

RLTAYHPEIEELLFSDVENDEHMCVLKNRNKPIIFTMARLDRVKNLTGLVELYAKNPRLRELVNLVVVGGDRRKESK

DLEEQAEMKKMYELIKTHNLNGQFRWISSQMNRVRNGELYRYIADTRGAFVQPAFYEAFGLTVVEAMTCGLPTFATN

HGGPAEIIVHGKSGFHIDPYHGDQAAELLADFFEKCKKEPSHWEAISEGGLKRIQEKYTWQIYSDRLLTLAAVYGFW

KHVSKLDRLEIRRYLEMFYALKFRKLVSFIAFCTPAIV

SEQ ID NO: 15: Polynucleotide sequence of NtSUS4-T
atggccgaacgtgtgctaactcgtgttcacagccttcgcgaacgtcttgatgctactttggctgctcatcgcaatga gattttgctgtttctttcaaggtatagtcttagcagattgttctttgatttagttggtgttatttgccagttctaat gtatggactaatatatgaacaaagtgcgaccatttcaactgacaacttaaaatgtttgagagaatacacgtttattt -continued acttaattatggcttgagcataggaagtgtatcttggcgtaactcgtaaagttgacctcatgtgacaaggaggtcac ggtttcgagccgtggaaacagcctcttgcagaaatgcaggtaaggctgcgtgcaatagatcgcccttccacggaccc gcgcatagcgggaacttagtgcaccggttgggctgtcctttttttatgtcttcagcacaaaaatttagtttaaacatg tgtatcatggattattcatgctggttttgccggttgcaggattgaaagccacggaaaagggatattgaaacctcacc agttgctggctgagtttgaatcaattcacaaagaagacaaaaacaaactgaatgatcatgcttttgaagaagtcctg aaatctactcaggtaatttgtggttttagtgttaggtgatggatagcatttattgtcttactaagatcatatatgtg tcagtttgtggctagtatttgaaaagtctggtgtggtttgtcatactaggaagcaattgtcttgtccccttgggttg cgcttgccattcgtctgcggcctggtgtgtgggaatatgttcgtgtgaatgtcaatgcacttattgtcgaggagctg actgtgcctgaatatttgcaattcaaggaagaacttgttaatggaacgtaagttttaggttcgaaatgatgatttgt taaataatatgttctgaactttttgattaatgttgtgttttcccctgatgcagctcgaacgataactttgttcttga gctggattttgagcccttcactgcatcatttcccaaaccaaccctcaccaaatcaattggaaatggagttgaattcc tcaaccgacacctctctgccaaaatgttccatgacaaggaaagcatgacccctcttctcgagtttcttcgagttcat cactacaagggcaaggtaaacttgtttttcctgtttgtctatgaatttagtttctgaaagttgctttgcttcgtgaa tttttagtggcaactgatttatgattttctgtgcagacaatgatgctgaatgacagagttcaggacttaaacactc tccaaaatgtcctaaggaaggctgaggaatatctcactaccctttcccctgaaacttcatactcggtatttgagcac aagttccaagaaattggcctagagaggggctggggtgacaatgctgagcgtgttctagagatgatctgcatgctcct ggatctcctcgaggctccagactcatgcactcttgagaagttccttggtagaattcctatggtttttaatgtggtca ttctttcacctcacggatatttcgcccaggaaaatgtcttgggttaccccgatactggtggccaggtgcactgctta tttgtaacaccttacgcttttccctctgaaacttatttgcggcaagttctaaggtcctccttccttaatttgcaggt tgtctatattttggatcaagttccggccttggagcgtgagatgctcaagcgcataaaggagcaaggacttgatatca aaccgcgtattcttattgttcgtatctccaataattgcgtttaaacttatgattgtgcaggatttgatctgttcaaa tctaatgactgattttcttttttttttttttttccctcaggttactcggctgctgcctgatgcggttggtaccactt gtggtcagcggcttgagaaagtgtttggaacagagcattcacatattcttagggtcccctttaggaccgagaagggc atcgttcgcaaatggatctctcgctttgaagtctggccttacatggagacattcactgaggtgaagcaagctttctc tattcatttttcaatcttccaatctgttttggcagcaatttttcacttactaacactttggctttcgctaaaacttc ggattttattacattaggatgtggcaaaagaaattgctgcagaactgcaggcaaagccagatcttataatcggcaac tacagcgagggcaaccttgctgcctccttgttggctcacaagttaggtgtaactcaggtctgtaatgtttgtcacct gttatttcaactttgcatttcctttcatttgcaactagaagttaagagttctctctcttttatcttttccgtctatt ttgccttctgcagtgcaccatagctcatgcgttggagaaaacaaaatatcctgattctgatatctacttgaagaaat ttgatgaaaaataccatttctcagcccagtttactgccgatcttattgcaatgaatcacaccgatttcataatcacc agcactttccaggagatagcgggaaggtattacatcacaatggatttccgatatgattaaattagttaatttaatcc tacttcattgtgtttgatcctaaaacttttctaaatttcccagcaaggacactgttggacagtacgagagccacatg gctttcacgatgcctggattgtatagagttgttcacggcattgatgtgttcgatcccaaattcaacattgtgtcacc aggagctgatatgaatctctatttcccctacttcgagaaggaaaagcgattgacagcatatcaccctgaaattgagg agctgctgtttagcgatgttgagaatgacgaacacatgtatgttactaaactagcaatcctgctgcaaaattgtggc taattatgtaaaaaagtttttactgaatagatttgtgcttctatcaggtgtgtgctgaaggacaggaataagccaat tatattcaccatggctagattggatcgagtgaagaacttaactggacttgtggagttgtacgccaagaacccacggc taagggagttggttaaccttgtcgtggttggtggagaccgaaggaaggaatccaaagatttggaagaacaggcagag atgaagaagatgtatgaacttataaagacgcacaatttaaacggccaattccgatggatttcttcccagatgaaccg cgtgaggaatggcgaactctacaggtacattgccgatactaggggagcttttgtgcagcctgcattttacgaggctt ttggtttgactgttgttgaggccatgacctgtggtttgcctacgtttgcaactaatcacggtggtccagctgagatc -continued atcgttcacgggaagtctggttttcacattgatccataccacggcgagcaggcagctgaacttctagctgatttctt tgagagatgtaagaaagaaccttcacactgggaagccatttccgagggcggccttaagcgtatacaggagaagtaag caagctgctactcttttcatttttgcaaaacctaccatgatcattattaagctcatttttgcaaaacctacttgtta ttctttgttgcttccttttccctgtttttttgagccgaggttttatcgaaaacatgctttctaccttcacaaggtagg ggtaaggtctgcgtttgttattattgttgttgttgattctctgcgaattaattaaaaggtacacatggcaaatctac tcggatcggttgttgacactggctgctgtttatggattctggaagcatgtttccaaacttgatcgtcttgaaattcg tcgttatcttgaaatgttctatgctctaaaattccgcaaactggtgagtttcactgctttctgcactcttccaattg ttagttgagtgcactcatttaaactgtagctaaagctgttgtaaatcttcagttaagcagctgctaatgaagtttttt atcttttgtttttggttcaggctgaagctgtcccgttggctgttgagtaa SEQ ID NO: 16: Polypeptide sequence of NtSUS4-T
MAERVLTRVHSLRERLDATLAAHRNEILLFLSRIESHGKGILKPHQLLAEFESIHKEDKNKLNDHAFEEVLKSTQEA

IVLSPWVALAIRLRPGVWEYVRVNVNALIVEELTVPEYLQFKEELVNGTSNDNEVLELDEEPFTASFPKPTLTKSIG

NGVEFLNRHLSAKMFHDKESMTPLLEFLRVHHYKGKTMMLNDRVQDLNTLQNVLRKAEEYLTTLSPETSYSVFEHKF

QEIGLERGWGDNAERVLEMICMLLDLLEAPDSCTLEKFLGRIPMVFNVVILSPHGYFAQENVLGYPDTGGQVVYILD

QVPALEREMLKRIKEQGLDIKPRILIVTRLLPDAVGTTCGQRLEKVFGTEHSHILRVPFRTEKGIVRKWISRFEVWP

YMETFTEDVAKEIAAELQAKPDLIIGNYSEGNLAASLLAHKLGVTQCTIAHALEKTKYPDSDIYLKKEDEKYHFSAQ

FTADLIAMNHTDFIITSTFQEIAGSKDTVGQYESHMAFTMPGLYRVVHGIDVFDPKFNIVSPGADMNLYFPYFEKEK

RLTAYHPEIEELLFSDVENDEHMCVLKDRNKPIIFTMARLDRVKNLTGLVELYAKNPRLRELVNLVVVGGDRRKESK

DLEEQAEMKKMYELIKTHNLNGQFRWISSQMNRVRNGELYRYIADTRGAFVQPAFYEAFGLTVVEAMTCGLPTFATN

HGGPAEIIVHGKSGFHIDPYHGEQAAELLADFFERCKKEPSHWEAISEGGLKRIQEKYTWQIYSDRLLTLAAVYGFW

KHVSKLDRLEIRRYLEMFYALKFRKLAEAVPLAVE

SEQ ID NO: 17: Polynucleotide sequence of NtSUS5-S
atggcctcaacagttgctgatagcatgcctgatgctttgaaacaaagccggtatcatatgaagagatgcttcgctag gtgaacacccttcttttatgtttttttcccctctacgtgtttatgtcaaatttccatgcataatgctaactacttttc ttctttttgacttcaaaattggatgtgaaaggttcattgcaatgggaaggaggctaatgaagttgaaacatttaaca gaagaaatagaagaaactattgaagacaaggcagaaagaaccaggattttggagggttcacttggaaaaattatgag ttccacacaggtcagcaccatttaaccaacttagttgaacaggaaaaaaagaaaaagcaaaagagttattgcaaggc gtaacgattttctttgaaattttcaggaggcagctgttgttccaccttatgttgcttttgcagtaaggcacaatcct ggcttctgggattatgtcaaagttaacgctgaaactctctctgtggaagctatttcagccagggaatatctcaaatt caaagagatgatctttgacgaagactggtaagtggaaaattgtatcattttaaagagaaacaattttgtaacataca agaatagttttgatggttgaatgtgcaagcagggcaaaggatgataatgcactggaagtagattttggtgcttttga ctactctaatcctcggttagccctttcctcttctgtcggaaatgggctcaactttatctcaaaagttctgtcttcaa agtttggtggaaagccagaggacgcccagcctttgcttgattacttactagctcttaatcatcaaggagaggtatga aaatggactacctttgtttcttaaaggtattatataatgatgcgcgttataaagttcctttttaaattgaaactttg cagaatctaatgatcaatgagaatctgaatggtgttgctaagcttcaagcagcattgatagtagctgaagtttttgt atcttcctttcccaaagacacaccttataaagactttgagcataagtaagcttctcatatgcttccattgtcatatg cagtataccaatgacatgctaccgaaaagttgtttatgtttgtgacttgattatgaaaactctaggctcaaagaatg gggctttgataaagggtggggtcacaatgcaggaagagtaagagagacaatgagactgctttccgagataatccaag caccagatcccataaatatggagtcctttttcagcaagcttcctactacattcaacattgttatcttctccattcat ggttactttggccaagcagatgtccttggtctgcccgatactggaggccaggtctacatatacagcaatttatctcc ttttgcctcatattgcttattagcgacacttgcatcattgaaatcagacttttacttcacaggttgtttatattctg -continued gatcaagtaagggctttagaggaggaaatgttacaaagaatcaagcagcaagggctaaacgtgaagcccaagattct tgtggtgagttttgcaaaaatatgcttagacaggttttgagattgatcggagaagggattaagatgatcaagatctt tgtttcctgctttcatgatgtaaacaggtatctcgtctcataccagatgctcgagggacaacatgcaatcaggagat ggaacctattcttaactcatcccattctcacatcctgagaattccattcaggactgagaaaggagttcttcgccaat gggtttctcggtttgatatctatccttacttggagaactatgccaaggcaagtcttctaacaaaattaccacctatt catacactttatttactttcttgaactaatcgtttggtttgtgacgtatatcattaggatgcttctgctaagatact tgagctcatggaaggtaaaccagacctcataattgggaactacactgatggaaatttagtggcatctctattggcca acaaacttggagttactcaggttccgtagctgatcatatgatcatattttctacattgtttcttgataattaaatgg aaatcttattggatgataacattttagggaaccattgctcatgcattagagaaaactaagtatgaagattctgatgt gaagtggaagcagtttgatcccaagtaccacttttcttgccaatttactgccgatttattggcaatgaatgctgctg attttatcattaccagcacatatcaagaaatcgctggaaggttagcactgactctctcagtatatttggcaacttaa tgaatttactgcagtggccaacactaaaagctatcattcgtccttcagcgaaactaggcctggacaatatgaaagtc acacagcatttaccatgccggggctttatagagctgtttcaggcatcaatgtatttgatccaaagttcaacattgct gctcctggggctgaacagtctacctatttccctttcactgagaaacagaaacgattcagcacatttcgtcctgctat taacgaattactttacagtaatgaggaaaacaatgagcacatgtaagtctaattgcccattttcctaatctaaccat tgcttaaatcgttctgtttttaccggatgtgtggtacttatcagtaacatttttttttggatcagtggatttcttgc agaccggaaaaaaccaattatattttcaatggcgagatttgatacagtgaagaacctgtcaggcttgactgagtggt atgggaagaataagaagttgcggaacttggtaaaccttgttattgttggggggattcttcgatccatcaaaatcaaaa gaccgggaggaagcagctgaaatcaagaagatgcatgaattgattgagaaataccagctcaagggacaaatgagatg gatagcagctcaaactgataaatatcgaaatagtgagctataccgaactattgctgacactaagggagcttttgtcc aaccggctttatatgaagcttttggactaaccgttattgaagcaatggattgtggattgcctacgtttgcaactaat caaggtggacctgcagaaatcattgttgatggggtttcaggtttccatattgatccttacaatggggacgaatcaag caagaaaatagctgatttctttgagaagtgtaaggttgattctaaatattggaacaggatatctgagggaggtctca agcgcattgaagaatggtaacaaactagttccaagtttaaaaaatggaaaaaatgcttatcatgttatattttcgtg gttttaagttctgcttcgatgcagttatacgtggaagatttatgcaaacaaagtgttgaatatgggatcaatctatg gattttggagacaattcaatgtggggcaaaagcaggctaagcaaagatactttgagatgttttacaatcctctcttc aggaaattggtaggttgtatatgttgaatacaatttactaagatcctcaaaatgaccaagaaatatacattgactat gctacttttgtaatttcacaggccaaaagcgtgccgatcccacatgaagagccattgccacttgcaacatcagactc tactcaatcccaagaattaaaactaccactaccagttccagcagcagtagctaaagttctgccattaacaaggcatg cttttaacttaattacttctctacctagagtaactggtaaagtggatgtcaagtga SEQ ID NO: 18: Polypeptide sequence of NtSUS5-S

MASTVADSMPDALKQSRYHMKRCFARFIAMGRRLMKLKHLTEEIEETIEDKAERTRILEGSLGKIMSSTQEAAVVPP

YVAFAVRHNPGFWDYVKVNAETLSVEAISAREYLKFKEMIFDEDWAKDDNALEVDFGAFDYSNPRLALSSSVGNGLN

FISKVLSSKFGGKPEDAQPLLDYLLALNHQGENLMINENLNGVAKLQAALIVAEVFVSSFPKDTPYKDFEHKLKEWG

FDKGWGHNAGRVRETMRLLSEIIQAPDPINMESFFSKLPTTFNIVIFSIHGYFGQADVLGLPDTGGQVVYILDQVRA

LEEEMLQRIKQQGLNVKPKILVVSRLIPDARGTTCNQEMEPILNSSHSHILRIPFRTEKGVLRQWDASAKILELMEG

KPDLIIGNYTDGNLVASLLANKLGVTQGTIAHALEKTKYEDSDVKWKQFDPKYHFSCQFTADLLAMNAADFIITSTY

QEIAGSETRPGQYESHTAFTMPGLYRAVSGINVFDPKENIAAPGAEQSTYFPFTEKQKRFSTFRPAINELLYSNEEN

NEHIGFLADRKKPIIFSMARFDTVKNLSGLTEWYGKNKKLRNLVNLVIVGGFFDPSKSKDREEAAEIKKMHELIEKY

QLKGQMRWIAAQTDKYRNSELYRTIADTKGAFVQPALYEAFGLTVIEAMDCGLPTFATNQGGPAEIIVDGVSGFHID

-continued

PYNGDESSKKIADFFEKCKVDSKYWNRISEGGLKRIEECYTWKIYANKVLNMGSIYGEWRQFNVGQKQAKQRYFEMF

YNPLFRKLAKSVPIPHEEPLPLATSDSTQSQELKLPLPVPAAVAKVLPLTRHAFNLITSLPRVTGKVDVK

SEQ ID NO: 19: Polynucleotide sequence of NtSUS5-T
atggcctcaactgttgctggtagcatgcctgatgctttgaaacaaagccgatatcatatgaagagatgcttcgctag gtgaacacccttcttgttctttttgtttttttccctctaccatttatgtcaaatttcaatgcataatgctaactactt tttttctttttgacttcaaaattggacgtgaaaggttcattgcaatgggaaggaggttgatgaagctgaaacattta acagaagaaatagaaaaaactattgaagacaaggcagaaagaaccaagattttggagggttcacttggaaaaattat gagttccacacaggtcagcaccatttaaccaacttaattgaataggaagaaaaaaaaaagcaaaagagttattgcaa ggcgtaacgatttcctttgaaattttcaggaggcagctgttgtcccaccttatgttgcttttgcagtaaggcacaat cctggcttctgggattatgtcaaagttgacgctgaaactctctctgtggaagctatttcagccagggactatctcaa attcaaagagatgatctttgatgaagattggtaactggaagattgtatcattttaaagaaacaatttttttaatattc aagattagttttgatggttgaatgtgcaagcagggcaaaggatgaaaatgcactcgaagtagattttggtgcttttg actactctaatcatcggttagccctttcctcttctgtcggaaatgggctaaacttcatctcgaaagttttgtcttca aagtttggtggaaaggcagaagatgcccagcctttgcttgattacttactagctcttaatcatcaaggagaggtatg gaaatggactaccttcctttcttaaggaattatataatgatgtatgttataaagatcctttttaaacattgacactt tgcagaatctaatgatcaatgagaatctgaatggcgtctctaagcttcaagcagcattgatagtagctgaagttttt gtatcttcctttcccaaagacacaccttataaagactttgagcataagtaagcttttcaaacgcttctgttatcata tgcaatataccaagaatatgttgccttttgaaaagttgtttatgtttatgacttgataatgaaaatactaggctcaa agaatggggctttgagaaagggtggggtcacaatgcaggaagagtaagagagacaatgagactgctttccgagataa tccaagcgccagatcccataaatatggagtcctttttcagcaggcttcctactacattcaacattgttatcttctcc attcatggttactttggccaagcagatgtccttggtttgcccgatactggaggccaggtttacatacacagcaattt atctccttttgcctcatatttacttattagcgacacttgcattattgaaatcacatttgtatttaacaggttgttta tattctggatcaagtaagagccttagaggaggaaatgttacaaagaatcaagcagcaagggttaaatgtgaagccca agattcttgtggtgagttatgcaaaaatatgcgtagccaaggttttgaaattgttcagaggggattaagatgatcga gatatttgtttccttcttccattgatgtgtacaggtcactcgtctcattccagatgctcgagggactacatgcaatc aggagatggaacctatacttaactcgtcccattctcacatcctgagaattccattcaggacagagaaaggagttctt cgccaatgggtttctcggtttgatatctatccttacttggagaactatgccaaggcaagtctcctaccaaaattacc acctattcatacactttattcagtttttttgagctaatcattctcatttgtcacgtatgtgattaggatgcttctgct aagatacttgagctcatggaaggtaaaccagacctcattattgggaactacactgatggaaatttagtggcatctct attggccaacaaacttggagttactcaggttctacagctgatcatttatctgatcagattttctacattgttttctt gataattaaacggaaatcttatgagattgtaacattttagggaaccattgctcatgcattagagaaaaccaagtatg aagattctgatgtcaagtggaagcagtttgattccaagtaccacttttcttgccaattcactgccgatttattggca atgaatgctgctgattttatcattaccagcacatatcaagaaatcgcaggaaggttagcactgactctctcagtata tttggcaacttaatgaatgtactgcttgtggccaacactaaaagctattactcgtccttcagcgaaactaggcctgg acaatatgaaagtcacacagcatttaccatgccggggctttatagagctgtttcaggcatcaatgtatttgatccaa agttcaacattgctgctcctggggctgaacagtctgcctatttccccttcactgagaaacagaaacgattcagcgcg tttcgtcctgctattgaggaactactttacagtaatgagcaaaacaacgagcacatgtaagtctaattgccccattt tcctaatctaaccattgcttaaatgttctgtttttacttgatatgtggtacttatcagtgatatttttttattggaac agtggatttcttgcagaccgtaaaaaaccaattatattttcaatggcaagatttgatacggtgaagaacttgtcagg cttgactgagtggtatgggaagaataagaagttgcggaacttggttaacctcgttatcgttgggggattcttcgatc catcaaaatcaaaagaccgggaggaagcagctgaaatcaagaagatgcatgaattgattgagaaatacaagctcaag -continued ggacaaatgagatggatagcagctcaaactgataaatatcaaaacagtgagctatatcgaactattgctgacactaa aggagctttcgtccaaccggctttatatgaagcttttggactaactgttattgaagcaatgaattgtggactgccta catttgctactaatcaaggcggacctgcagaaatcattgttgatggggtttcaggcttccatattgatccttacaat ggggatgaatcgagcaagaaaatagctgatttctttgagaagtgtaaggttgattctaaatattggaacaagatatg tggaggaggtctcaagcgcattgaagaatggtaa SEQ ID NO: 20: Polypeptide sequence of NtSUS5-T
MASTVAGSMPDALKQSRYHMKRCFARFIAMGRRLMKLKHLTEEIEKTIEDKAERTKILEGSLGKIMSSTQEAAVVPP

YVAFAVRHNPGFWDYVKVDAETLSVEAISARDYLKFKEMIFDEDWAKDENALEVDFGAFDYSNHRLALSSSVGNGLN

FISKVLSSKFGGKAEDAQPLLDYLLALNHQGENLMINENLNGVSKLQAALIVAEVFVSSFPKDTPYKDFEHKLKEWG

FEKGWGHNAGRVRETMRLLSEIIQAPDPINMESFFSRLPTTFNIVIFSIHGYFGQADVLGLPDTGGQVVYILDQVRA

LEEEMLQRIKQQGLNVKPKILVVTRLIPDARGTTCNQEMEPILNSSHSHILRIPFRTEKGVLRQWDASAKILELMEG

KPDLIIGNYTDGNLVASLLANKLGVTQGTIAHALEKTKYEDSDVKWKQEDSKYHFSCQFTADLLAMNAADFIITSTY

QEIAGSETRPGQYESHTAFTMPGLYRAVSGINVFDPKENIAAPGAEQSAYFPFTEKQKRFSAFRPAIEELLYSNEQN

NEHIGFLADRKKPIIFSMARFDTVKNLSGLTEWYGKNKKLRNLVNLVIVGGFFDPSKSKDREEAAEIKKMHELIEKY

KLKGQMRWIAAQTDKYQNSELYRTIADTKGAFVQPALYEAFGLTVIEAMNCGLPTFATNQGGPAEIIVDGVSGFHID

PYNGDESSKKIADFFEKCKVDSKYWNKICGGGLKRIEEW

SEQ ID NO: 21: Polynucleotide sequence of NtSUS6-S
atggctactgcaccagccctaaatagatcagagtccatagctgatagcatgccagaggccttaaggcaaagccggta ccacatgaagaaatgttttgccaagtacatagagcaaggaaagaggatgatgaaacttcataacttgatggatgagt tggagaaagtaattgatgatcctgctgaaaggaaccatgttttggaaggcttacttggctacatattatgcactaca atggtatagctagattcatatgtacttatgatgcccttatattgtttcctgatgtattactcttaaaaccttctttg atcaaatttacaggaggctgcagttgttcctccctacattgcctttgccacgagacagaatcctggattctgggaat atgtgaaagtgaatgctaatgatctttctgttgagggtattacagctacagaatacttgaaattcaaggaaatgata gttgatgaatgctggtatagtatacgttgcagcttatcatacctttttgtggttttataacttcaatcagaaaactca tcagagttacctttgtgtgaacatgaaatgcagggcaaaagatgaatatgcactggaaattgattttggagcagtag acttctcaacgcctcgactgaccctatcctcttcaattggcaatggtctcagttatgtttccaagtttctaacttca aagctaaatgctacctccgcgagtgcacagtgtctggttgactacttgctcactttgaatcatcaaggagatgtacg tcaacaaaaatcaaactccataagtaaacttgtcaactctaagaagaaaaaataggaaaagaagattcacgtaacaa attttctttatgttcaactgcagaaactgatgatcaatgagacactcagcactgtctcaaagcttcaggctgcactg gttgtagcagaagcatctatttcctctttaccaacagatacaccatatgagagctttgagctaaggtgatttgtttt ttcctctacttccctccacttgtgccatgctacgtagtactaagtaacttcaattcttgtaaagattcaaacagtgg ggttttgagaaaggatggggtgatacagctgaaagggtcagcgacaccatgagaacactgtctgaggtgcttcaggc accagatccattgaacattcagaagttctttggaagggttccaactgttttcaatattgtattgttctctgtccatg gatactttggccaagcagatgttcttggcttgccagacactggtggtcaggtaagcatttaatagcttttacattta acttctatgcattgacaataaaataatttttaacagtttgaccacttctgctcttgttcaacaggtagtttatgttt tggatcaagttgtagcttttgaagaagaaatgctacaaagaattaaacagcaggggctcaatattaagcctcaaatt cttgtggtgagttcctagacaatcgacgtgactatgcaattatgtagaggctgtttagaaaagttaatatcatatgt tgattgcacagttaacccgactgattccggatgcaaaaggaacaaagtgcaaccaggaactagaaccaatcaagaat acaaaacattcacacatcctcagagttccatttaggacagaaaaaggagtgcttaatcaatgggtttcacgatttga tatctatccatatctggagagatatactcaggtatgtatttttatatcaaccttgctcatcaaagatgtgttgtttc ctcaattccatttttccccttggcaaaaggatgctgctgacaaaatcgtcgagctaatggaaggcaaacctgatcta -continued atcattggtaactacactgatgggaatctagtggcttcactaatggctagaaaacttgggataactctggtaacttt tcttaatcatatttgatgttgcttcttctccaagttagttcttaatctccactgacctagaccatctttgcaacagg gaactattgctcatgctttggagaagacaaaatatgaagactctgacataaaattgaaggaactcgatccgaagtac cacttctcttgccaattcacagctgatttgattgcaatgaattcagcagatttcattatcactagcacataccaaga aatagctggaaggtaagaattagagctaataagtaatgcattcatatgtatttcagcatcgctctttcaccatcatc gaatacacaccactactcagtaaatgtatttgctcaaaagtttgcaacttaatggatctcattcttgaatgcttcaa catatgcagcaaagataaaccaggacagtatgagagccatagtgcatttacccttccagggctttacagagttgctt caggtatcaatgtctttgatccaaaatttaatattgctgcacctggggcagaccagtcggtgtatttcccttacaca gaaaagcagaagcgtttgactgctttccgccctgccattgaggaactgctttttagtaaagtggacaatgacgagca cgtgtaagtctaagtgttaaacttcagcttagtgcctagaacatcccactgctctatgtattgatgtttcacttgtt tcaaacagtggatatttagaagacagaaagaaacctatcctgtttaccatggcaaggctggacacagtgaagaacac atctggactaacagaatggtatggcaagaacaagaggctcagaagcttagttaaccttgttgtggttggtggttcct ttgatcctacaaaatccaaggatagggaagaagcagctgaaataaaaaagatgcacatgctgatagagaaataccag cttaagggtcagattagatggatagcagctcagactgacagatacagaaatagtgaactctaccgcacaatagcaga ttccaaaggagcttttgtgcagcctgcattgtatgaagcatttggtctaacagtcattgaggcaatgaactgtggat taccaacctttgctaccaaccaaggtggccctgctgagattattgttgatggggtctcaggctttcatattgatcca aataatggggatgaatcaagcaacaaaattgccaactttttccaaaaatgcagggaggatcctgagtattggaacag gatttcagtccagggtctaaaccgtatatatgaatggtaactcacagataagccattcaaattgcaaagaggcacat atcttgcagaaaatttcttaatccttaaatcctaatttttttgcagttacacatggaagatctatgcaaacaaggtat tgaatatggggtccatctatactttttggaggacattgtacagagatcagaaacaagcaaagcaaagatacatcgag actttctacaatcttgagtttaggaacttggtatagtgctgcatgacattgacagtataccacaaacatctttatga gatgaattacttttaataaaattgtttttaacctttgcttccttaatggcacttattgcaggtaaaaaatgtgccta tcagaaaggacgaaacaccacaaggaccaaaggagagggagaaagttaagccacagatatcacaaaggcatgctcta aagcttttgcctacagtttttcaagagaccctagtatattctagtactaaattagaattatacagcatgcagctttt gctgttcacctttctaaatcaccagttgtgtcaatcaagttgacaaaatcaataaattgggatttttcccctttcctat gcttgattgttattactcctactttgtttatggtagtcttccttcattgttttctcctgtacttcttttactacaac tgtactgacatactaattatttctgtgtaccaggcgctcacaatcaaggttgcagaagtaagattagataaaattgc tactgcatga SEQ ID NO: 22: Polypeptide sequence of NtSUS6-S
MATAPALNRSESIADSMPEALRQSRYHMKKCFAKYIEQGKRMMKLHNLMDELEKVIDDPAERNHVLEGLLGYILCTT

MEAAVVPPYIAFATRQNPGFWEYVKVNANDLSVEGITATEYLKFKEMIVDECWAKDEYALEIDEGAVDFSTPRLTLS

SSIGNGLSYVSKFLTSKLNATSASAQCLVDYLLTLNHQGDKLMINETLSTVSKLQAALVVAEASISSLPTDTPYESF

ELRFKQWGFEKGWGDTAERVSDTMRTLSEVLQAPDPLNIQKFFGRVPTVFNIVLFSVHGYFGQADVLGLPDTGGQVV

YVLDQVVAFEEEMLQRIKQQGLNIKPQILVLTRLIPDAKGTKCNQELEPIKNTKHSHILRVPFRTEKGVLNQWVSRF

DIYPYLERYTQDAADKIVELMEGKPDLIIGNYTDGNLVASLMARKLGITLGTIAHALEKTKYEDSDIKLKELDPKYH

FSCQFTADLIAMNSADFIITSTYQEIAGSKDKPGQYESHSAFTLPGLYRVASGINVFDPKENIAAPGADQSVYFPYT

EKQKRLTAFRPAIEELLFSKVDNDEHVGYLEDRKKPILFTMARLDTVKNTSGLTEWYGKNKRLRSLVNLVVVGGSFD

PTKSKDREEAAEIKKMHMLIEKYQLKGQIRWIAAQTDRYRNSELYRTIADSKGAFVQPALYEAFGLTVIEAMNCGLP

TFATNQGGPAEIIVDGVSGFHIDPNNGDESSNKIANFFQKCREDPEYWNRISVQGLNRIYECYTWKIYANKVLNMGS

IYTFWRTLYRDQKQAKQRYIETFYNLEFRNLVKNVPIRKDETPQGPKEREKVKPQISQRHALKLLPTVFQETLALTI

KVAEVRLDKIATA

-continued

SEQ ID NO: 23: Polynucleotide sequence of NtSUS6-T atggctactgcaccagccctgaaaagatcagagtccatagctgatagcatgccagaggccttaaggcaaagccggta ccacatgaagaaatgttttgccaagtacatagagcaaggcaagaggatgatgaaacttcataacttgatggatgaat tggagaaagtaattgatgatcctgctgaaaggaaccatgttttggaaggcttacttggctacatattatgtactaca atggtatagctagattcatatgtacttatgatgtccttatattgtttccggaggcattattcttaaatccttctttg atcaaatttgtaggaggctgcagttgttcctccctatattgccttcgccacgagacagaatcctggattctgggaat atgtgaaagtcaatgctaatgatctttctgttgagggtattacagctacagattacttgaaattcaaggaaatgata gttgatgaaagctggtatagaatactttgcagcttatcatacctttgtggttttataatttcaatcagaaaactca tcagagttacctttgtgtgaacatgacatgcagggcaaaagatgaatatgcactggaaattgattttggagcagtag acttctcaacgcctcgactgaccctatcctcttcaattggaaatggtctcagttatgtttccaagtttctaacttca aagctaaatgctacctcagcgagtgcacagtgtctggttgactacttgctcactttgaatcaccaaggagatgtacg tcaacaaaaatcaaactccataagtaaacttgtcaactctaagaagtaaaaataggaaaagaagattcatgtaacaa attttctttatgttcaactgtagaaactgatgatcaatgagacactcggcactgtctcaaagcttcaggctgcactg gttgtagcagaagcatctatttcctccttaccaacagatacaccataccagagctttgagctaaggtgatttgtttt ttcctctacttccttccacttttggtgtgctacatagtactaagtaacttcaattcttgtaaagattcaaacagtgg ggttttgagaaaggatggggtgatacagctgaaagggtccgcgacaccatgagaacactttctgaggtacttcaggc gccagatccattgaacattgagaagttctttgggagggttccaactgttttcaatattgtattgttctctgttcatg gatactttggccaagcaaatgttcttggcttgccagacacaggtggtcaggtaagcatctaatagcttttacattta acttctatgcattgacaataaaataacttctacactaccaaataatttttgaaagtttgaccacttcggctcttgtt caacaggtggtttatgttttggatcaagttgtagcttttgaagaagaaatgctccaaagaattaaacagcaggggct caatattaagcctcaaattcttgtggtgagctcctagacaatgacgtgactatgcaattaagtagaggctgtttaga aaagttaatatcatatgttgattgcacagttaacccgactgattccggacgccaaaggaacaaagtgcaaccaggaa ctagaaccaatcaagaatacaaaacattcacacatcctcagagttccatttaggacagaaaaaggagtgcttaatca atgggtttcacgatttgatatctatccatatctggagagatatactcaggtgtgtatttttatatcaaccctgctca tcaaagatgtgttgtttcctcaattccatttttcgccttgacaaaaggacgctgctgacaaaatcatcgagctaatg gaaggcaaacctgatctaatcattggtaactacactgatgggaatctagtggcttctctaatggctagaaagcttgg gataactctggtaacttttcttatcatatttgatgttgtttcttctccaagttggttcttaatgtcaactaacccag accatctttgtaacagggaactattgctcatgctctggagaagacaaaatatgaagactctgacatcaaattgaagg aactcgatccgaagtaccacttttcttgccaattcacagctgatttgattgcaatgaattcagcagatttcattatc acaagcacatatcaagaaatagccggaaggtaagaattggaactacggaagcagagagctaataagtagtgcactca tatatttcagcatcgctctttcgcataatcgaatacacaccactactcagtaaatgtacttgctcaaaagtttacaa gtttatggatcttattcttgaatgcttcaacatatgcagcaaagataggccaggacagtatgagagccatagtgcat ttacccttccagggctttacagagttgcttcaggcatcaatgtctttgatcctaaatttaatattgctgcacctggg gcagaccaatcggtgtatttcccttacacagaaaagcagacgcgtttgactgctttccgccctgccattgaggaact gctttttagtaaagtggacaatgacgagcacatgtaagtcttagtgttaaacttcagctttcagcttagtgcctaga acattccactggctctatgtattaatgtttcacttgtttcaaacacagtggatatttagaagacagaaagaaaccta tcctgtttaccatggcaaggctggacacagtgaagaacacatctggactaacagaatggtatggcaagaacaagagg ctcagaagcttagttaaccttgttgtggttggtggttcctttgatcctacaaaatccaaggatagagaagaagcagc tgaaataaaaaagatgcacatgctgatagagaaataccagcttaagggtcagatcagatggatagcagctcagactg acagatatagaaacagtgaactctaccgcacaatagcagattccaaaggagcttttgtgcagcctgcattatatgaa gcatttggtctaacagtcattgaggcaatgaactgtggattaccaacctttgctaccaaccaaggtggccctgctga -continued gattattgttgatggggtctcaggctttcatattgatccaaataatggggatgaatcaagcaacaaagttgccaact ttttccaaaaatgcagggaggatcctgagtattggaacaggatttcagtccagggtctaaaccgtatatatgaatgg taactcacagataagccattcaaattgcaaagaggcacatatcttgctgaaaatttcttaatcctttaatcctaaaa ttttgcagttacacatggaagatctatgcaaacaaggtattgaatatggggtccatctatactttttggaggacatt gtacagagatcagaaacaagcaaagcaaagatacatcgagactttctacaatcttgagtttaggaacttggtatagt gctgcatgacattgacagtataccacaaacatctttatgagatgaattacttttaataaaattgtttttaacctttg cctccttaatgacacttattgcaggtaaaaaatgtgcctatcagacaggacgaaacaccacaaggaccaaaggagag gagggagaaagttaagccacagatatcacaaaggcatgctctaaagcttttgcctatagtttttcaggagaccctag tatattctagtactaaattagaattatacagcatgcagcttgcttctgctgttcacctttctaaatcaccagttatg tcaatcaagttgacaaaatcaataaattcggcttttccctttcctatgcttgattgttattactcctacttcgttta tggtagtcttccttcattgttttctcctgtacttcttttactacaactgtactga SEQ ID NO: 24: Polypeptide sequence of NtSUS6-T
MATAPALKRSESIADSMPEALRQSRYHMKKCFAKYIEQGKRMMKLHNLMDELEKVIDDPAERNHVLEGLLGYILCTT

MEAAVVPPYIAFATRQNPGFWEYVKVNANDLSVEGITATDYLKFKEMIVDESWAKDEYALEIDEGAVDFSTPRLTLS

SSIGNGLSYVSKFLTSKLNATSASAQCLVDYLLTLNHQGDKLMINETLGTVSKLQAALVVAEASISSLPTDTPYQSF

ELRFKQWGFEKGWGDTAERVRDTMRTLSEVLQAPDPLNIEKFFGRVPTVFNIVLFSVHGYFGQANVLGLPDTGGQVV

YVLDQVVAFEEEMLQRIKQQGLNIKPQILVLTRLIPDAKGTKCNQELEPIKNTKHSHILRVPFRTEKGVLNQWVSRF

DIYPYLERYTQDAADKIIELMEGKPDLIIGNYTDGNLVASLMARKLGITLGTIAHALEKTKYEDSDIKLKELDPKYH

FSCQFTADLIAMNSADFIITSTYQEIAGSKDRPGQYESHSAFTLPGLYRVASGINVFDPKFNIAAPGADQSVYFPYT

EKQTRLTAFRPAIEELLFSKVDNDEHIGYLEDRKKPILFTMARLDTVKNTSGLTEWYGKNKRLRSLVNLVVVGGSFD

PTKSKDREEAAEIKKMHMLIEKYQLKGQIRWIAAQTDRYRNSELYRTIADSKGAFVQPALYEAFGLTVIEAMNCGLP

TFATNQGGPAEIIVDGVSGFHIDPNNGDESSNKVANFFQKCREDPEYWNRISVQGLNRIYECYTWKIYANKVLNMGS

IYTFWRTLYRDQKQAKQRYIETFYNLEFRNLVKNVPIRQDETPQGPKERREKVKPQISQRHALKLLPIVFQETLVYS

STKLELYSMQLASAVHLSKSPVMSIKLTKSINSAFPFPMLDCYYSYFVYGSLPSLFSPVLLLLQLY

---

The invention claimed is:

1. A cured *Nicotiana tabacum* leaf comprising:

(i) a polynucleotide comprising a sequence having at least 95% sequence identity to SEQ ID NO: 9 or SEQ ID NO: 11; or a polynucleotide comprising a sequence having at least 80% sequence identity to SEQ ID NO: 5 or SEQ ID NO: 13;

(ii) a polypeptide encoded by the polynucleotide set forth in (i);

(iii) a polypeptide comprising a sequence having at least 95% sequence identity to SEQ ID NO: 6; or at least 93% sequence identity to SEQ ID NO: 10 or SEQ ID NO: 12; or at least 95% sequence identity to SEQ ID NO: 14; or (iv) a construct, vector or expression vector comprising the isolated polynucleotide set forth in (i), wherein said cured *Nicotiana tabacum* leaf comprises at least one modification which modulates the expression or activity of the polynucleotide or the polypeptide as compared to a control cured *Nicotiana tabacum* leaf in which the expression or activity of the polynucleotide or polypeptide has not been modified.

2. The cured leaf according to claim 1, wherein the at least one modification is a modification of the cured leaf's genome, or a modification of the construct, vector or expression vector, or a transgenic modification.

3. The cured leaf according to claim 1, wherein the modification increases or decreases the expression or activity of the polynucleotide or the polypeptide as compared to the control cured leaf.

4. The cured leaf according to claim 1, wherein the modulated expression or activity of the polynucleotide or the polypeptide modulates the level of reducing sugars in the cured leaf as compared to the level of reducing sugar in the control cured leaf.

5. The cured leaf according to claim 1, wherein the cured leaf is flue-cured, sun-cured or air-cured plant material.

6. A tobacco product comprising the cured lead of claim 1.

7. A method for producing the cured *Nicotiana tabacum* leaf of claim 1, comprising the steps of:

(a) providing a *Nicotiana tabacum* plant cell comprising a polynucleotide comprising a sequence having at least 95% sequence identity to SEQ ID NO: 9 or SEQ ID NO: 11; or having at least 80% sequence identity to SEQ ID NO: 5 or SEQ ID NO: 13;

(b) modifying the plant cell to modulate the expression of said polynucleotide as compared to a control plant cell; and (c) propagating the plant cell into a *Nicotiana tabacum* plant;

(d) harvesting a leaf therefrom; and (e) curing the leaf.

8. The method according to claim 7, wherein step (c) comprises cultivating the plant from a cutting or seedling comprising the plant cell; and/or wherein the step of modifying the plant cell comprises modifying the genome of the cell by genome editing or genome engineering.

9. The method according to claim 7, wherein the step of modifying the plant cell comprises transfecting the cell with a construct comprising a polynucleotide comprising a sequence having at least 95% sequence identity to or SEQ ID NO: 9 or SEQ ID NO: 11; or having at least 80% sequence identity to SEQ ID NO: 5 or SEQ ID NO: 13 operably linked to a constitutive promoter; and/or wherein the step of modifying the plant cell comprises introducing an interference polynucleotide comprising a sequence that is at least 80% complementary to an RNA transcribed from the polynucleotide of claim 1(i) into the cell.

10. The method according to claim 7, wherein the curing method is selected from the group consisting of air curing, fire curing, smoke curing, and flue curing.

11. The cured leaf according to claim 2, wherein the modification of the plant cell's genome, or the modification of the construct, vector, or expression vector is a mutation or edit.

12. The cured leaf according to claim 3, wherein the cured leaf comprises an interference polynucleotide comprising a sequence that is at least 80% complementary to at least 19 nucleotides of an RNA transcribed from the polynucleotide of claim 1(i).

13. The cured leaf according to claim 4, wherein the reducing sugar is glucose or fructose.

14. The method according to claim 8, wherein the genome editing or genome engineering is selected from CRISPR/Cas technology, zinc finger nuclease-mediated mutagenesis, chemical or radiation mutagenesis, homologous recombination, oligonucleotide-directed mutagenesis and meganuclease-mediated mutagenesis.

15. The method according to claim 9, wherein the cured leaf is transfected with a construct expressing an interference polynucleotide comprising a sequence that is at least 80% complementary to at least 19 nucleotides of an RNA transcribed from the polynucleotide of claim 1(i).

* * * * *